US007754738B2

(12) United States Patent
Lahm et al.

(10) Patent No.: US 7,754,738 B2
(45) Date of Patent: Jul. 13, 2010

(54) PYRAZOLE AND PYRROLE CARBOXAMIDE INSECTICIDES

(75) Inventors: George Philip Lahm, Wilmington, DE (US); Robert James Pasteris, Wilmington, DE (US); Thomas Martin Stevenson, Newark, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/514,183

(22) PCT Filed: Jun. 10, 2003

(86) PCT No.: PCT/US03/18609

§ 371 (c)(1), (2), (4) Date: Nov. 10, 2004

(87) PCT Pub. No.: WO03/106427

PCT Pub. Date: Dec. 24, 2003

(65) Prior Publication Data

US 2006/0167060 A1 Jul. 27, 2006

Related U.S. Application Data

(60) Provisional application No. 60/388,244, filed on Jun. 13, 2002.

(51) Int. Cl.
*A01N 43/40* (2006.01)
*A61K 31/44* (2006.01)

(52) U.S. Cl. ....................... 514/332; 514/333; 514/341; 514/406

(58) Field of Classification Search ................. 514/341, 514/406, 332, 333
See application file for complete search history.

(56) References Cited

U.S. PATENT DOCUMENTS 5,998,424 A 12/1999 Galemmo, Jr. et al.
6,020,357 A 2/2000 Pinto et al.
6,403,620 B1 6/2002 Galemmo, Jr. et al.
6,548,512 B1 4/2003 Pinto et al.
6,602,895 B2 8/2003 Galemmo, Jr. et al.
6,747,047 B2 6/2004 Lahm et al.
6,965,032 B2 11/2005 Freudenberger
6,995,178 B2 2/2006 Lahm et al.
7,038,057 B2 5/2006 Annis et al.
7,087,598 B2 8/2006 Clark
7,148,217 B2 12/2006 Selby
7,157,475 B2 1/2007 Clark
7,179,824 B2 2/2007 Zimmerman
7,199,138 B2 4/2007 Finkelstein et al.
7,232,836 B2 6/2007 Lahm et al.
7,241,767 B2 7/2007 Clark et al.
7,288,554 B2 * 10/2007 Finkelstein et al. ......... 514/341
2004/0102324 A1 5/2004 Annis et al.
2004/0110777 A1 6/2004 Annis et al.
2004/0209923 A1 10/2004 Berger et al.
2004/0242645 A1 * 12/2004 Clark et al. ................. 514/340
2005/0075372 A1 4/2005 Lahm et al.
2006/0205748 A1 * 9/2006 Annis et al. ................. 514/275

FOREIGN PATENT DOCUMENTS

EP 0 946 508 A1 10/1999
EP 0 991 625 B1 6/2005
JP 2129171 5/1990
WO WO98/28269 7/1998
WO WO98/57937 12/1998
WO WO0170671 9/2001
WO WO03016300 2/2003
WO WO03016304 2/2003
WO WO03026415 4/2003
WO WO03027099 4/2003

OTHER PUBLICATIONS

Kordik et al, Pyrazolecarboxamide human neuropeptide Y5 receptor ligands with in vivo antifeedant activity, Bioorganic & Medicinal Chemistry Letters, 2001, 11(17), 2287-2290.*

XP002275434 Order Nos. 5K-0011, 5K-014, 2H-016, 5K-020, 5K026 and "Interchim Intermediates" Jul. 9, 2002, Interchim, 231 Avenue.

* cited by examiner

*Primary Examiner*—Alton N Pryor

(57) ABSTRACT

This invention provides compounds of Formula (I), N-oxides and salts thereof wherein: A is O or S; B is a phenyl ring or a pyridine ring, each ring optionally substituted with 1 to 5 R; J is a pyrazole or a pyrrole heterocyclic ring system as defined herein; and; $R^1$ is H; or $C_1$-$C_6$ alkyl, $C_2$-$C_6$ alkenyl, $C_2$-$C_6$ alkynyl or $C_3$-$C_6$ cycloalkyl each optionally substituted with one or more substituents selected from the group consisting of halogen, CN, $NO_2$, hydroxy, $C_1$-$C_4$ alkoxy, $C_1$-$C_4$ alkylthio, $C_1$-$C_4$ alkylsulfinyl, $C_1$-$C_4$ alkylsulfonyl, $C_2$-$C_4$ alkoxycarbonyl, $C_1$-$C_4$ alkylamino, $C_2$-$C_8$ dialkylamino and $C_3$-$C_6$ cycloalkylamino. Also disclosed are methods for controlling at least one invertebrate pest comprising contacting the invertebrate pest or its environment with a biologically effective amount of at least one compound of Formula I, an N-oxide or a salt thereof (e.g., as a composition described herein). This invention also pertains to a composition comprising at least one compound of Formula I, an N-oxide or a salt thereof; and at least one additional component selected from the group consisting of a surfactant, a solid diluent and a liquid diluent.

(I)

A=C(J)–N(B)(R¹)

8 Claims, No Drawings

PYRAZOLE AND PYRROLE CARBOXAMIDE INSECTICIDES

BACKGROUND OF THE INVENTION

This invention relates to certain heterocyclic amides, their N-oxides, salts and compositions suitable for agronomic and nonagronomic uses, including those uses listed below, and a method of their use for controlling invertebrate pests in both agronomic and nonagronomic environments.

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, and public and animal health is also important. Many products are commercially available for these purposes, but the need continues for new compounds that are more effective, less costly, less toxic, environmentally safer or have different modes of action.

JP02129171 discloses pyrazolecarboxanilide derivatives of Formula i as insecticides i

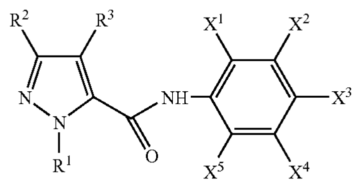

wherein, $R^1$ through $R^3$ and $X^1$ through $R^5$ are as defined therein.

SUMMARY OF THE INVENTION

This invention pertains to compounds of Formula I, and N-oxides or salts thereof

I

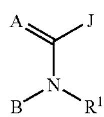

wherein

A is O or S;

B is a phenyl ring or a pyridine ring, each ring substituted with 1 to 5 $R^2$;

J is a pyrazole or a pyrrole heterocyclic ring system selected from the group consisting of J-1, J-2, J-3, J-4, J-5 and J-6;

J-1

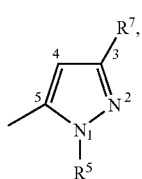

-continued

J-2

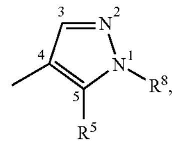

J-3

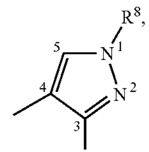

J-4

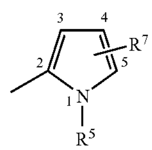

J-5

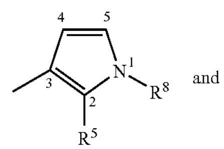

J-6

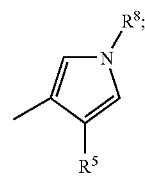

$R^1$ is H; or $C_1$-$C_6$ alkyl, $C_2$-$C_6$ alkenyl, $C_2$-$C_6$ alkynyl or $C_3$-$C_6$ cycloalkyl each optionally substituted with one or more substituents selected from the group consisting of halogen, CN, $NO_2$, hydroxy, $C_1$-$C_4$ alkoxy, $C_1$-$C_4$ alkylthio, $C_1$-$C_4$ alkylsulfinyl, $C_1$-$C_4$ alkylsulfonyl, $C_2$-$C_4$ alkoxycarbonyl, $C_1$-$C_4$ alkylamino, $C_2$-$C_8$ dialkylamino and $C_3$-$C_6$ cycloalkylamino; or $R^1$ is $C_2$-$C_6$ alkylcarbonyl, $C_2$-$C_6$ alkoxycarbonyl, $C_2$-$C_6$ alkylaminocarbonyl, or $C_3$-$C_8$ dialkylaminocarbonyl;

each $R^2$ is independently selected from the group consisting of H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, $C_2$-$C_4$ cyanoalkyl, halogen, CN, $NO_2$, piperidine, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, and $C_3$-$C_6$ cycloalkylamino; or each $R^2$ is independently selected from the group consisting of a phenyl, benzyl or phenoxy ring, each ring optionally substituted with one or more substituents selected from the group consisting of $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_4$-$C_7$ (alkyl)cycloalkylamino, $C_2$-$C_6$ alkoxycarbonyl, $C_2$-$C_6$ alkylaminocarbonyl, and $C_3$-$C_8$ dialkylaminocarbonyl;

$R^5$ is

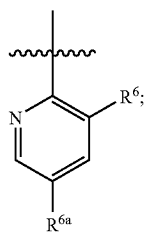

each $R^6$, $R^{6a}$ and $R^7$ is independently selected from the group consisting of H, $C_1$-$C_6$ alkyl, $C_3$-$C_6$ cycloalkyl, $C_1$-$C_6$ haloalkyl, halogen, CN, $C_1$-$C_4$ alkoxy, $C_1$-$C_4$ alkylthio, $C_1$-$C_4$ haloalkoxy and $C_1$-$C_4$ haloalkylthio; and $R^8$ is H, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, $C_3$-$C_6$ haloalkynyl, or $C_1$-$C_4$ haloalkoxy.

This invention also pertains to a method for controlling at least one invertebrate pest comprising contacting the invertebrate pest or its environment with a biologically effective amount of at least one compound of Formula I, an N-oxide or a salt thereof (e.g., as a composition described herein). This invention also relates to such a method wherein the invertebrate pest or its environment is contacted with a biologically effective amount of at least one compound of Formula I, an N-oxide or a salt thereof, or with a biologically effective amount of a composition comprising at least one compound of Formula I, an N-oxide or a salt thereof; and a biologically effective amount of at least one other biologically active compound or agent for controlling invertebrate pests.

This invention also pertains to a composition comprising at least one compound of Formula I, an N-oxide or a salt thereof; and at least one additional component selected from the group consisting of a surfactant, a solid diluent and a liquid diluent. This invention also pertains to a composition comprising at least one compound of Formula I, an N-oxide or a salt thereof; and at least one other biologically active compound or agent.

DETAILS OF THE INVENTION

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio and butylthio isomers. "Alkylsulfinyl" includes both enantiomers of an alkylsulfinyl group. Examples of "alkylsulfinyl" include $CH_3S(O)$, $CH_3CH_2S(O)$, $CH_3CH_2CH_2S(O)$, $(CH_3)_2CHS(O)$ and the different butylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl isomers. "Cyanoalkyl" denotes an alkyl group substituted with one cyano group. Examples of "cyanoalkyl" include $NCCH_2$, $NCCH_2CH_2$ and $CH_3CH(CN)CH_2$. "Alkylamio", "dialkylamino", and the like, are defined analogously to the above examples. "Cycloalkyl" includes, for example, cyclopropyl, cyclobutyl, cyclopentyl, and cyclohexyl. The term "cycloalkylamino" includes the same groups linked through a nitrogen atom such as cyclopentylamino and cyclohexylamino.

The term "hetero" in connection with rings or ring systems refers to a ring or ring system in which at least one ring atom is not carbon and which can contain 1 to 4 heteroatoms independently selected from the group consisting of nitrogen, oxygen and sulfur, provided that each ring contains no more than 4 nitrogens, no more than 2 oxygens and no more than 2 sulfurs. The terms "heteroaromatic ring or ring system" and "aromatic fused heterobicyclic ring system" includes fully aromatic heterocycles and heterocycles in which at least one ring of a polycyclic ring system is aromatic (where aromatic indicates that the Hückel rule is satisfied). The heterocyclic ring or ring system can be attached through any available carbon or nitrogen by replacement of a hydrogen on said carbon or nitrogen.

The term "halogen", either alone or in compound words such as "haloalkyl", includes fluorine, chlorine, bromine or iodine. Further, when used in compound words such as "haloalkyl" or "halocycloalkyl", said alkyl or cycloalkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", "haloalkylthio", and the like, are defined analogously to the term "haloalkyl". Examples of "haloalkenyl" include $(Cl)_2C{=}CHCH_2$ and $CF_3CH_2CH{=}CHCH_2$. Examples of "haloalkynyl" include $HC{\equiv}CCHCl$, $CF_3C{\equiv}C$, $CCl_3C{\equiv}C$ and $FCH_2C{\equiv}CCH_2$. Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylsulfinyl" include $CF_3S(O)$, $CCl_3S(O)$, $CF_3CH_2S(O)$ and $CF_3CF_2S(O)$. Examples of "haloalkylsulfonyl" include $CF_3S(O)_2$, $CCl_3S(O)_2$, $CF_3CH_2S(O)_2$ and $CF_3CF_2S(O)_2$.

Examples of "alkylcarbonyl" include $C(O)CH_3$, $C(O)CH_2CH_2CH_3$ and $C(O)CH(CH_3)_2$. Examples of "alkoxycarbonyl" include $CH_3C({=}O)$, $CH_3CH_2C({=}O)$, $CH_3CH_2CH_2C({=}O)$, $(CH_3)_2CHOC({=}O)$ and the different butoxy- or pentoxycarbonyl isomers. Examples of "alkylaminocarbonyl" include $CH_3NHC({=}O)$, $CH_3CH_2NHC({=}O)$, $CH_3CH_2CH_2NHC({=}O)$, $(CH_3)_2CHNHC({=}O)$ and the different butylamino- or pentylaminocarbonyl isomers. Examples of "dialkylaminocarbonyl" include $(CH_3)_2NC({=}O)$, $(CH_3CH_2)_2NC({=}O)$, $CH_3CH_2(CH_3)NC({=}O)$, $CH_3CH_2CH_2(CH_3)NC({=}O)$ and $(CH_3)_2CHN(CH3)C({=}O)$.

The total number of carbon atoms in a substituent group is indicated by the "$C_i$-$C_j$" prefix where i and j are numbers from 1 to 8. For example, $C_1$-$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

In the above recitations, when a compound of Formula I is comprised of one or more heterocyclic rings, all substituents are attached to these rings through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript indicates a range, e.g. $(R)_{i-j}$, then the number of substituents may be selected from the integers between i and j inclusive.

The term "optionally substituted with one to three substituents" and the like indicates that one to three of the available positions on the group may be substituted. When a group contains a substituent which can be hydrogen, for example $R^1$ or $R^5$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I, N-oxides and salts thereof. The compounds of the invention can be present as a mixture of stereoisomers, individual stereoisomers, or as an optically active form.

One skilled in the art will appreciate that not all nitrogen containing heterocycles can form N-oxides since the nitrogen requires an available lone pair for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry,* vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group such as a carboxylic acid or phenol. In the compositions and methods of this invention, the salts of the compounds of the invention are preferably suitable for the agronomic and/or non-agronomic uses described herein.

As noted above, B is a phenyl ring or a pyridine ring, each ring substituted with 1 to 5 $R^2$. Examples of said B rings wherein said rings are substituted with 1 to 5 $R^2$ include the ring systems illustrated as B-1 to B-4 in Exhibit 1 below, wherein n is an integer from 1 to 5 and $R^2$ is as defined above. Note that some B groups can only be substituted with less than 5 $R^2$ groups (e.g. B-2 through B-4 can only be substituted with 4 $R^2$).

Exhibit 1

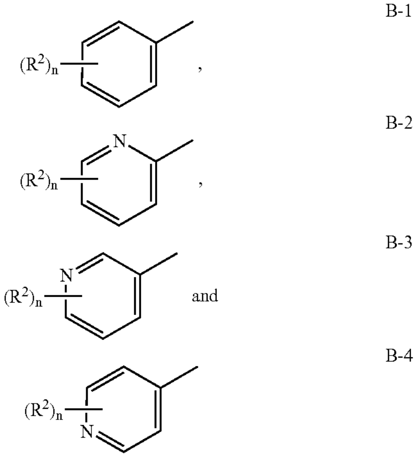

A preferred B ring is optionally substituted phenyl.

Of note are compounds of Formula I wherein

A is O or S;

B is a phenyl ring or a pyridine ring, each ring substituted with 1 to 5 $R^2$;

J is a pyrazole or a pyrrole heterocyclic ring system selected from the group consisting of J-1, J-2, J-3, J-4, J-5 and J-6;

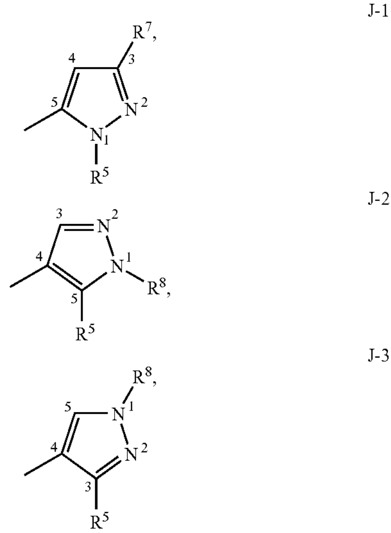

-continued

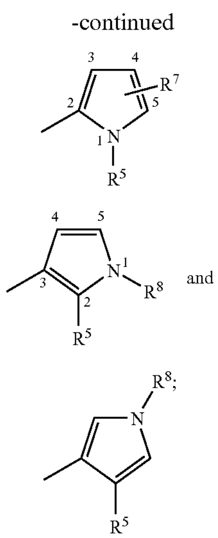

$R^1$ is H; or $C_1$-$C_6$ alkyl, $C_2$-$C_6$ alkenyl, $C_2$-$C_6$ alkynyl or $C_3$-$C_6$ cycloalkyl each optionally substituted with one or more substituents selected from the group consisting of halogen, CN, $NO_2$, hydroxy, $C_1$-$C_4$ alkoxy, $C_1$-$C_4$ alkylthio, $C_1$-$C_4$ alkylsulfinyl, $C_1$-$C_4$ alkylsulfonyl, $C_2$-$C_4$ alkoxycarbonyl, $C_1$-$C_4$ alkylamino, $C_2$-$C_8$ dialkylamino and $C_3$-$C_6$ cycloalkylamino; or $R^1$ is $C_2$-$C_6$ alkylcarbonyl, $C_2$-$C_6$ alkoxycarbonyl, $C_2$-$C_6$ alkylaminocarbonyl, or $C_3$-$C_8$ dialkylaminocarbonyl;

each $R^2$ is independently selected from the group consisting of H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, $C_2$-$C_4$ cyanoalkyl, halogen, CN, $NO_2$, piperidine, $C_1$-$C_4$ alkoxy, $C_1$-$C_4$ haloalkoxy, $C_2$-$C_4$ alkoxycarbonyl, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, and $C_3$-$C_6$ cycloalkylamino; or each $R^2$ is independently selected from the group consisting of a phenyl, benzyl or phenoxy ring, each ring optionally substituted with one or more substituents selected from the group consisting of $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_4$-$C_7$ (alkyl)cycloalkylamino, $C_2$-$C_6$ alkoxycarbonyl, $C_2$-$C_6$ alkylaminocarbonyl, and $C_3$-$C_8$ dialkylaminocarbonyl;

$R^5$ is

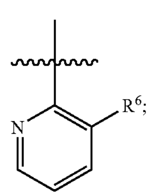

each $R^6$ and $R^7$ is independently selected from the group consisting of H, $C_1$-$C_6$ alkyl, $C_3$-$C_6$ cycloalkyl, $C_1$-$C_6$ haloalkyl, halogen, CN, $C_1$-$C_4$ alkoxy, $C_1$-$C_4$ alkylthio, $C_1$-$C_4$ haloalkoxy and $C_1$-$C_4$ haloalkylthio; and $R^8$ is H, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, $C_3$-$C_6$ haloalkynyl, or $C_1$-$C_4$ haloalkoxy.

Preferred compounds for reasons of better activity and/or ease of synthesis are:

Preferred 1. Compounds of Formula I above, and N-oxides and salts thereof, wherein J is J-1, J-2, J-3, or J-6.

Preferred 2. Compounds Preferred 1 wherein

A is O;

$R^1$ is H;

from 1 to 3 $R^2$ groups are other than H and are independently selected from the group consisting of $C_1$-$C_6$ alkyl, $C_1$-$C_6$ haloalkyl, $C_2$-$C_4$ cyanoalkyl, halogen, CN, $NO_2$, piperidine, $C_1$-$C_4$ alkoxy, $C_1$-$C_4$ haloalkoxy, $C_2$-$C_4$ alkoxycarbonyl, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl and $C_1$-$C_4$ haloalkylsulfonyl; and at least one $R^2$ as defined immediately above is ortho to the $NR^1C(=A)J$ moiety.

Preferred 3. Compounds of Preferred 2 wherein two $R^2$ are ortho to the $NR^1C(=A)J$ moiety.

Preferred 4. Compounds of Preferred 2 wherein $R^6$ is H, $C_1$-$C_4$ alkyl, $C_1$-$C_4$ haloalkyl, halogen or CN; and $R^7$ is H, $CH_3$, $CF_3$, $CH_2CF_3$, $CHF_2$, $OCH_2CF_3$, $OCHF_2$ or halogen.

Preferred 5. Compounds of Preferred 4 wherein

J is J-1;

$R^6$ is Cl or Br; and $R^7$ is halogen, $OCH_2CF_3$, $OCHF_2$ or $CF_3$.

Preferred 6. Compounds of Preferred 4 wherein

J is J-2;

$R^6$ is Cl or Br; and $R^8$ is $CH_2CF_3$ or $CHF_2$.

Preferred 7. Compounds of Preferred 4 wherein

J is J-3;

$R^6$ is Cl or Br; and $R^8$ is $CH_2CF_3$ or $CHF_2$.

Preferred 8. Compounds of Preferred 4 wherein

J is J-5;

$R^6$ is Cl or Br; and $R^8$ is $CH_2CF_3$ or $CHF_2$.

Preferred 9. Compounds of Preferred 4 wherein

J is J-6;

$R^6$ is Cl or Br; and $R^8$ is $CH_2CF_3$ or $CHF_2$.

This invention also pertains to a composition comprising at least one compound of Formula I, an N-oxide or a salt thereof; and at least one additional component selected from the group consisting of a surfactant, a solid diluent, and a liquid diluent. This invention also pertains to a composition comprising at least one compound of Formula I, an N-oxide or a salt thereof; and at least one other biologically active compound or agent. The preferred compositions of the present invention are those which comprise the above preferred compounds.

This invention also pertains to a method for controlling at least one invertebrate pest comprising contacting the invertebrate pest or its environment with a biologically effective amount of at least one compound of Formula I, an N-oxide or a salt thereof (e.g., as a composition described herein). This invention also relates to such a method wherein the invertebrate pest or its environment is contacted with a biologically effective amount of at least one compound of Formula I, an N-oxide or a salt thereof, or with a biologically effective amount of a composition comprising at least one compound of Formula I, an N-oxide or a salt thereof; and a biologically effective amount of at least one other biologically active compound or agent for controlling invertebrate pests. The preferred methods of use are those involving the above preferred compounds and compositions.

The compounds of Formula I can be prepared by one or more of the following methods and variations as described in Schemes 1-10. The definitions of A, B, J, $R^1$, $R^2$, $R^6$, $R^7$ and $R^8$ in the compounds of Formulae I and 2-32 below are as defined above in the Summary of the Invention unless otherwise indicated. Compounds of Formulae Ia-c are subsets of the compounds of Formula I.

A typical procedure is detailed in Scheme 1 and involves coupling of an aniline or aminopyridine of Formula 2 with an acid chloride of Formula 3 in the presence of a base to provide the compound of Formula Ia. Typical bases include amines such as triethylamine, diisopropylethylamine and pyridine; other bases include hydroxides such as sodium and potassium hydroxide and carbonates such as sodium carbonate and potassium carbonate. In certain instances it is useful to use polymer-supported acid scavengers such as polymer-bound equivalent of diisopropylethylamine and dimethylaminopyridine, such as PS—$CH_2N(iPr)_2$, wherein PS is the polystyrene backbone. In a subsequent step, amides of Formula Ia can be converted to thioamides of Formula Ib using a variety of standard thio transfer reagents including phosphorus pentasulfide and Lawesson's reagent (i.e. 2,4-bis(4-methoxyphenyl)-1,3-dithia-2,4-diphosphetane-2,4-disulfide).

Scheme 1

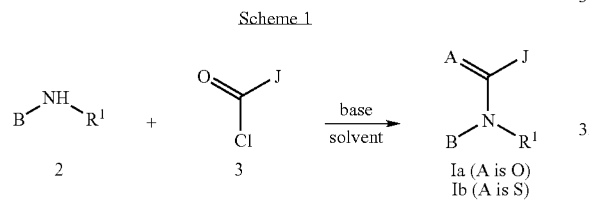

As shown in Scheme 2, an alternate procedure for the preparation of compounds of Formula Ia involves coupling of an aniline or aminopyridine of Formula 2 with an acid of Formula 4 in the presence of a dehydrating agent such as dicyclohexylcarbodiimide (DCC). Polymer supported reagents are again useful here, such as polymer-bound equivalent of cyclohexylcarbodiimide (PS—$CH_2N$═C═N-cyclohexyl). Synthetic procedures of Schemes 1 and 2 are only representative examples of useful methods for the preparation of Formula I compounds, as the synthetic literature is extensive for this type of reaction.

Scheme 2

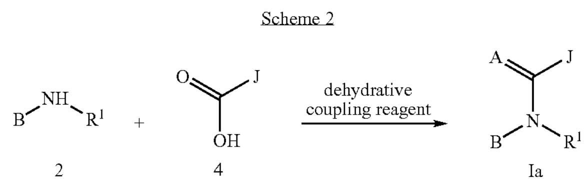

One skilled in the art will also realize that acid chlorides of Formula 3 may be prepared from acids of Formula 4 by numerous well-known methods, for example but not limited to, reaction of the acid with chlorinating reagents such as oxalyl chloride and thionyl chloride. Anilines and aminopyridines of Formula 2 are commercially available or are readily prepared by numerous well known methods.

Heterocyclic acids 4, where J is equal to an optionally substituted pyrazole or an optionally substituted pyrrole include those of Formula J-1 through J-6. More preferred analogs include the pyrazole and pyrrole acids that are substituted with $R^5$ as an optionally substituted phenyl or pyridyl. Procedures for the synthesis of representative examples of each are detailed in Schemes 3-9.

The synthesis of representative pyrazole carboxylic acids of Formula 5, which are related to Formula J-1 wherein $R^5$ is 2-pyridyl and attached to the nitrogen, is depicted in Scheme 3. Reaction of a pyrazole 6 with 2,3-dihalopyridines of Formula 7 affords good yields of the 1-pyridylpyrazole 8 with good specificity for the desired regiochemistry. Metallation of a compound of Formula 8 with lithium diisopropylamide (LDA) followed by quenching of the lithium salt with carbon dioxide affords the pyrazole acids of Formula 5. Additional details for these procedures are also described in Examples 1 and 2.

Scheme 3

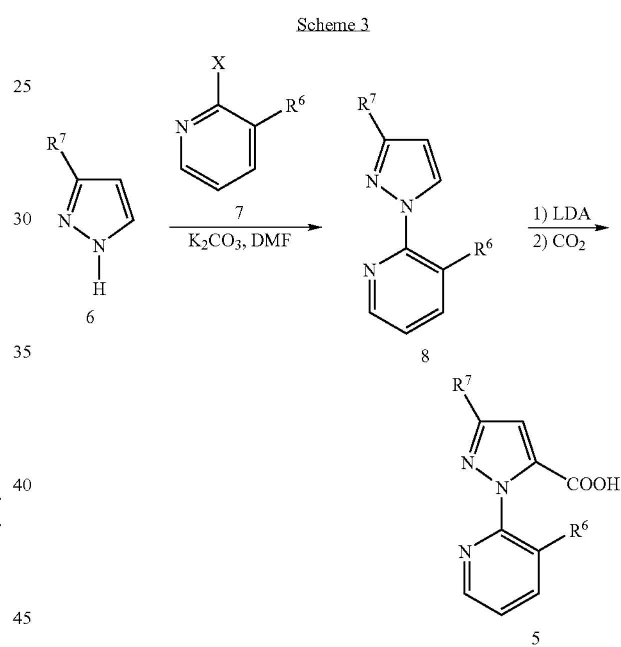

The starting pyrazoles 6 wherein $R^7$ is $CF_3$, Cl or Br are known compounds. Pyrazole 6 wherein $R^7$ is $CF_3$ can be prepared by literature procedures (*J. Fluorine Chem.* 1991, 53(1), 61-70). Pyrazoles 6 wherein $R^7$ is Cl or Br can also be prepared by literature procedures (H. Reimlinger and A. Van Overstraeten, *Chem. Ber.* 1966, 99(10), 3350-7). A useful alternative method for the preparation of 6 wherein $R^7$ is Cl or Br is depicted in Scheme 4.

Scheme 4

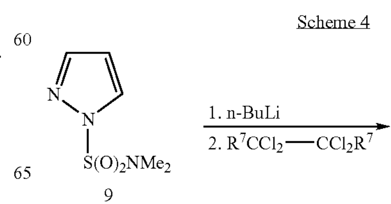

-continued

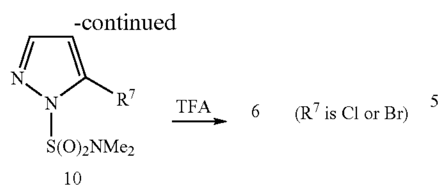

Metallation of the sulfamoyl pyrazole 9 with n-butyllithium followed by direct halogenation of the anion with either hexachloroethane (for $R^7$ being Cl) or 1,2-dibromotetrachloroethane (for $R^7$ being Br) affords the halogenated derivatives 10. Removal of the sulfamoyl group with trifluoroacetic acid (TFA) at room temperature proceeds cleanly and in good yield to afford the pyrazoles 6 wherein $R^7$ is Cl or Br respectively. Further experimental details for this method are described in Example 2.

The synthesis of representative pyrazole acids of Formula 14, which are related to Formula J-2 wherein $R^5$ is 2-pyridyl and attached to the 5 position of the pyrazole ring, is depicted in Scheme 5. Reaction of the dimethylaminoylidene ketoester of Formula 12 with substituted hydrazines affords the pyridylpyrazoles 13. Preferred $R^8$ substituents include alkyl and haloalkyl, with trifluoroethyl especially preferred. The esters 13 are converted to the acids of Formula 14 by standard hydrolysis.

Scheme 5

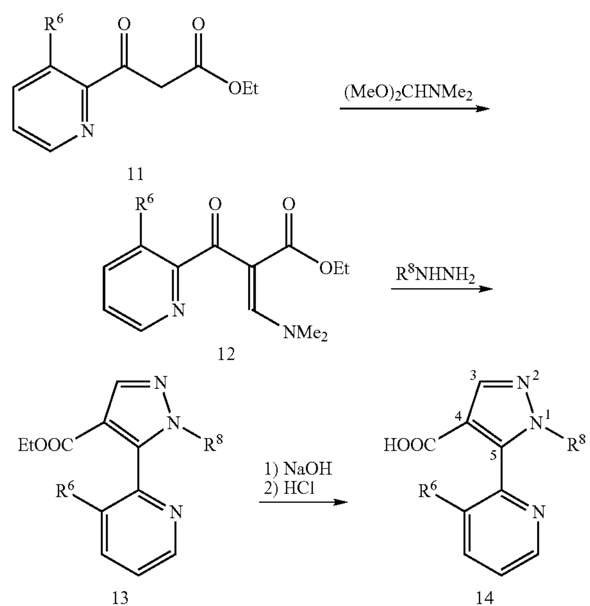

The synthesis of representative pyrazole acids of Formula 17, which are related to Formula J-3 wherein $R^5$ is 2-pyridyl and attached to the 3 position of the pyrazole ring as well as an alternative synthesis of Formula 14, is depicted in Scheme 6. Reaction of the dimethylaminoylidene ketoester of Formula 12 with hydrazine affords the pyrazole 15. Reaction of the pyrazole 15 with alkylating agents $R^8$-LG (wherein LG is a leaving group such as halogen (e.g., Br, I), $OS(O)_2CH_3$ (methanesulfonate), $OS(O)_2CF_3$, $OS(O)_2Ph\text{-}p\text{-}CH_3$ (p-toluenesulfonate), and the like) affords a mixture of pyridylpyrazoles 13 and 16. This mixture of pyrazole isomers is readily separated by chromatographic methods and converted to the corresponding acids. Preferred $R^8$ substituents include alkyl and haloalkyl groups.

Scheme 6

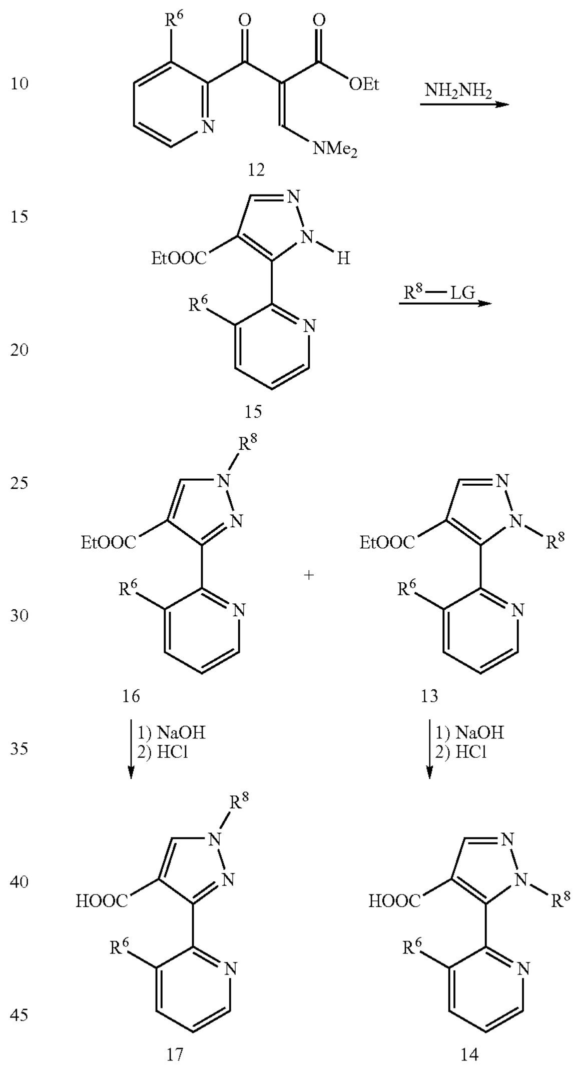

The synthesis of pyrrole acids of Formula 22, which are related to Formula J-4 wherein $R^5$ is 2-pyridyl and attached to the nitrogen of the pyrrole ring, is depicted in Scheme 7. 3-Chloro-2-aminopyridine 19 is a known compound (see *J. Heterocycl. Chem.* 1987, 24(5), 1313-16). A convenient preparation of 19 from 2-aminopyridine 18 involves protection, ortho-metallation, chlorination and subsequent deprotection. Treatment of a compound of Formula 19 with 2,5-dimethoxytetrahydrofuran affords pyrrole 20. Formylation of pyrrole 20 to the aldehyde of Formula 21 can be accomplished by using standard Vilsmeier-Haack formylation conditions. Halogenation of a compound of Formula 21 with N-halosuccinimides (NXS) occurs preferentially at the 4 position of the pyrrole ring. Oxidation of the halogenated aldehyde affords the pyridylpyrrole acids of Formula 22. The oxidation can be accomplished by using a variety of standard oxidation conditions.

Scheme 7

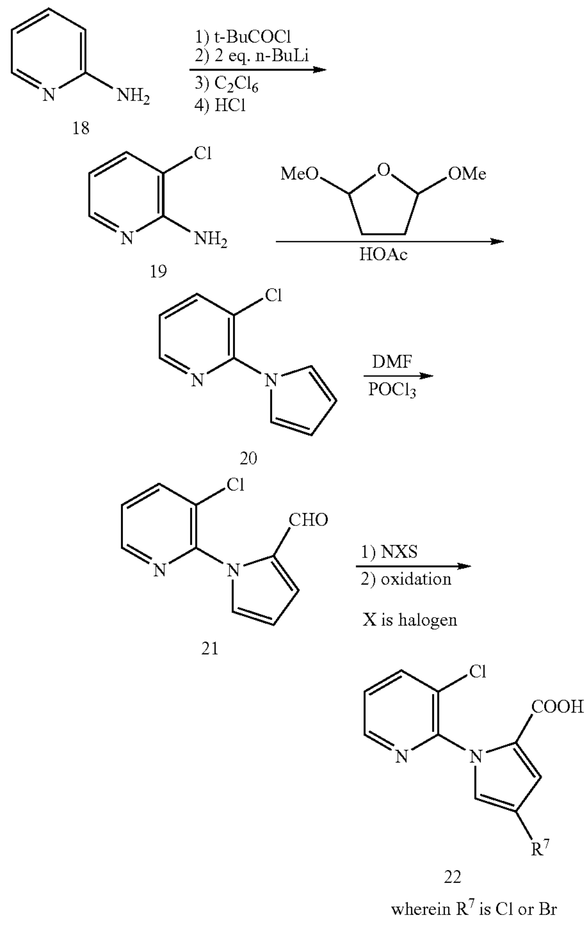

The synthesis of pyrrole acids of Formula 28, which are related to Formula J-5 wherein $R^5$ is phenyl or 2-pyridyl and attached to the 2 position of the pyrrole ring, is depicted in Scheme 8. Cycloaddition of an allene of Formula 25 with an aryl sulfonamide of Formula 24 (see Pavri, N. P.; Trudell, M. L. *J. Org. Chem.* 1997, 62, 2649-2651) affords the pyroline of Formula 26. Treatment of a pyrroline of Formula 26 with tetrabutylammonium fluoride (TBAF) gives a pyrrole of Formula 27. Reaction of a pyrrole 27 with alkylating agents $R^8$-LG (wherein LG is a leaving group as defined above) followed by hydrolysis affords a pyrrole acid of Formula 28.

Scheme 8

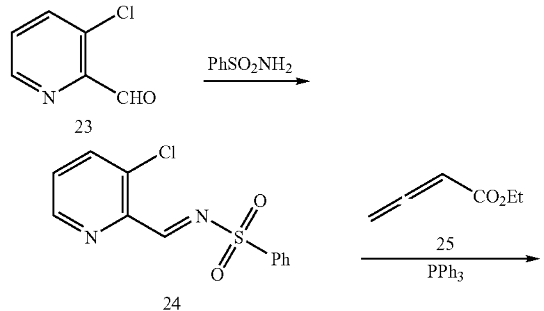

-continued

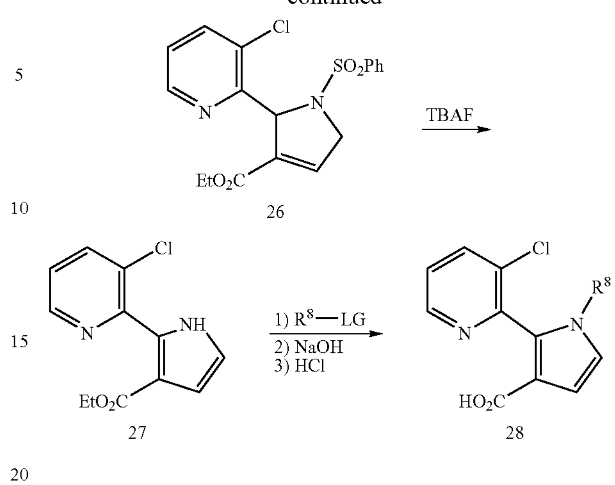

The synthesis of pyrrole acids of Formula 32, which are related to Formula J-6 wherein $R^5$ is 2-chlorophenyl or 2-pyridyl, is depicted in Scheme 9. Reaction of a cinnamic ester of Formula 29 with tosylmethyl isocyanide 30 (TosMIC) provides a pyrrole of Formula 31. For a leading reference to this method see, Xu, Z et al *J. Org. Chem.* 1998, 63, 5031-5041. Reaction of a compound of Formula 31 with an alkylating agent of Formula $R^8$-LG (wherein LG is a leaving group as defined above) followed by hydrolysis of the ester affords a pyrrole acid of Formula 32.

Scheme 9

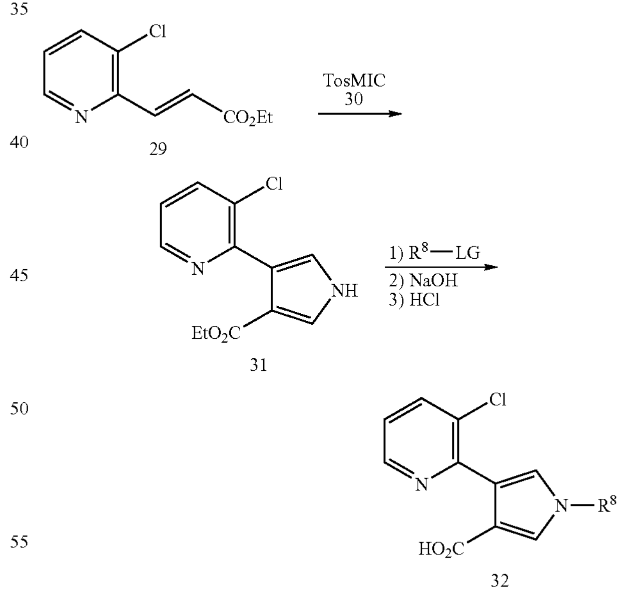

The synthesis of pyrazole amide analogs of Formula Ic is depicted in Scheme 10. This procedure takes advantage of the lithiated derivative of Formula 8. Treatment of a compound of Formula 8 with lithium diisopropylamide (LDA) followed by quenching of the lithium salt with aryl isocyanate affords compounds of Formula Ic, a subset of the compounds of Formula I. Additional details for this procedure are described in Example 1.

Scheme 10

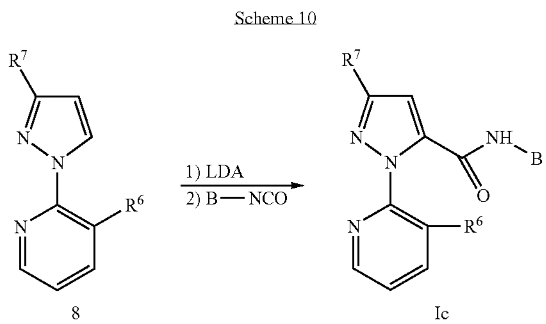

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s is singlet, d is doublet, t is triplet, q is quartet, m is multiplet, dd is doublet of doublets, dt is doublet of triplets, brs is broad singlet.

Example 1

Preparation of N-(2-chloro-6-methylphenyl)-1-(3-chloro-2-pyridinyl)-3-(trifluoromethyl)-1H-pyrazole-5-carboxamide Step A: Preparation of 3-chloro-2-[3-(trifluoromethyl)-1H-pyrazol-1-yl]pyridine To a mixture of 2,3-dichloropyridine (99.0 g, 0.67 mol) and 3-(trifluoromethyl)-pyrazole (83 g, 0.61 mol) in dry N,N-dimethylformamide (300 mL) was added potassium carbonate (166.0 g, 1.2 mol) and the reaction was then heated to 10-125° C. over 48 hours. The reaction was cooled to 100° C. and filtered through Celite® diatomaceous filter aid to remove solids. N,N-Dimethylformamide and excess dichloropyridine were removed by distillation at atmospheric pressure. Distillation of the product at reduced pressure (b.p. 139-141° C., 7 mm) afforded the title compound as a clear yellow oil (113.4 g).

$^1$H NMR ($CDCl_3$) δ 6.78 (s, 1H), 7.36 (t, 1H), 7.93 (d, 1H), 8.15 (s, 1H), 8.45 (d, 1H).

Step B: Preparation of 1-(3-chloro-2-pyridinyl)-3-(trifluoromethyl)-1H-pyrazole-5-carboxylic acid To a solution of 3-chloro-2-[3-(trifluoromethyl)-1H-pyrazol-1-yl]pyridine (i.e. the pyrazole product from Step A) (105.0 g, 425 mmol) in dry tetrahydrofuran (700 mL) at −75° C. was added via cannula a −30° C. solution of lithium diisopropylamide (425 mmol) in dry tetrahydrofuran (300 mL). The deep red solution was stirred for 15 minutes, after which time carbon dioxide was bubbled through at 63° C. until the solution became pale yellow and the exothermicity ceased. The reaction was stirred for an additional 20 minutes and then quenched with water (20 mL). The solvent was removed under reduced pressure, and the reaction mixture was partitioned between ether and 0.5 N aqueous sodium hydroxide solution. The aqueous extracts were washed with ether (3×), filtered through Celite® diatomaceous filter aid to remove residual solids, and then acidified to a pH of approximately 4, at which point an orange oil formed. The aqueous mixture was stirred vigorously and additional acid was added to lower the pH to 2.5-3. The orange oil congealed into a granular solid, which was filtered, washed successively with water and 1 N hydrochloric acid, and dried under vacuum at 50° C. to afford the title product as an off-white solid (130 g). (Product from another run following similar procedure melted at 175-176° C.)

$^1$H NMR (DMSO-$d_6$) δ 7.61 (s, 1H), 7.76 (dd, 1H), 8.31 (d, 1H), 8.60 (d, 1H).

Step C: Preparation of Preparation of N-(2-chloro-6-methylphenyl-1-(3-chloro-2-pyridinyl)-3-(trifluoromethyl)-1H-pyrazole-5-carboxamide A solution of 3-chloro-2-[3-(trifluoromethyl)-1H-pyrazol-1-yl]pyridine (i.e. the pyrazole product from Step A) (2.72 g, 11.14 mmol) in tetrahydrofuran (50 ml) was cooled to −70° C. Lithium diisopropylamine (2M in THF/Heptane, 5.5 mL, 11.0 mmol) was added over 2 minutes and the mixture was stirred for 15 minutes. 2-Chloro-6-methylphenyl isocyanate (1.90 g, 11.33 mmol) was added via syringe. The mixture was allowed to warm to 20° C. and quenched with a saturated aqueous solution of ammonium chloride (50 mL). The reaction mass was extracted with ethyl acetate (100 mL), dried over magnesium sulfate and concentrated. Chromatography on silica gel with a gradient of 3:1 hexanes/ethyl acetate to 1:1 hexanes/ethyl acetate afforded the title compound, a compound of the present invention as a solid (3.0 g) melting at 212-213° C.

$^1$H NMR ($CDCl_3$) δ 2.24 (3H), 7.1 (1H), 7.2 (1H), 7.25 (1H), 7.4 (1H), 7.6 (1H), 7.9 (1H), 8.5 (1H).

Example 2

Preparation of N-(2-bromo-4,6-difluorophenyl)-1-(3-chloro-2-pyridinyl)-3-bromo-1H-pyrazole-5-carboxamide Step A: Preparation of 3-bromo-N,N-dimethyl-1H-pyrazole-1-sulfonamide To a solution of N-dimethylsulfamoylpyrazole (44.0 g, 0.251 mol) in dry tetrahydrofuran (500 mL) at −78° C. was added dropwise a solution of n-butyllithium (2.5 M in hexane, 105.5 mL, 0.264 mol) while maintaining the temperature below 60° C. A thick solid formed during the addition. Upon completion of the addition the reaction mixture was maintained for an additional 15 minutes, after which time a solution of 1,2-dibromotetrachloroethane (90 g, 0.276 mol) in tetrahydrofuran (150 mL) was added dropwise while maintaining the temperature below −70° C. The reaction mixture turned a clear orange; stirring was continued for an additional 15 minutes. The −78° C. bath was removed and the reaction was quenched with water (600 mL). The reaction mixture was extracted with methylene chloride (4×), and the organic extracts were dried over magnesium sulfate and concentrated. The crude product was further purified by chromatography on silica gel using methylene chloride-hexane (50:50) as eluent to afford the title product as a clear colorless oil (57.04 g).

$^1$H NMR ($CDCl_3$) δ 3.07 (d, 6H), 6.44 (m, 1H), 7.62 (m, 1H).

Step B: Preparation of 3-bromopyrazole

To trifluoroacetic acid (70 mL) was slowly added 3-bromo-N,N-dimethyl-1H-pyrazole-1-sulfonamide (i.e. the bromopyrazole product of Step A) (57.04 g). The reaction mixture was stirred at room temperature for 30 minutes and then concentrated at reduced pressure. The residue was taken up in hexane, insoluble solids were filtered off, and the hexane was evaporated to afford the crude product as an oil. The crude product was further purified by chromatography on silica gel using ethyl acetate/dichloromethane (10:90) as eluent to afford an oil. The oil was taken up in dichloromethane, neutralized with aqueous sodium bicarbonate solution, extracted with methylene chloride (3×), dried over magnesium sulfate and concentrated to afford the title product as a white solid (25.9 g), m.p. 61-4° C.

$^1$H NMR ($CDCl_3$) δ 6.37 (d, 1H), 7.59 (d, 1H), 12.4 (br s, 1H).

Step C: Preparation of 2-(3-bromo-1H-pyrazol-1-yl)-3-chloropyridine

To a mixture of 2,3-dichloropyridine (27.4 g, 185 mmol) and 3-bromopyrazole (i.e. the product of Step B) (25.4 g, 176 mmol) in dry N,N-dimethylformamide (88 mL) was added potassium carbonate (48.6 g, 352 mmol), and the reaction mixture was heated to 125° C. for 18 hours. The reaction mixture was cooled to room temperature and poured into ice water (800 mL). A precipitate formed. The precipitated solids were stirred for 1.5 hours, filtered and washed with water (2×100 mL). The solid filter cake was taken up in methylene chloride and washed sequentially with water, 1N hydrochloric acid, saturated aqueous sodium bicarbonate solution, and brine. The organic extracts were then dried over magnesium sulfate and concentrated to afford 39.9 g of a pink solid. The crude solid was suspended in hexane and stirred vigorously for 1 hour. The solids were filtered, washed with hexane and dried to afford the title product as an off-white powder (30.4 g) determined to be >94% pure by NMR. This material was used without further purification in Step D.

$^1$H NMR ($CDCl_3$) δ 6.52 (s, 1H), 7.30 (dd, 1H), 7.92 (d, 1H), 8.05 (s, 1H), 8.43 (d, 1H).

Step D: Preparation of 3-bromo-1-(3-chloro-2-pyridinyl)-1H-pyrazole-5-carboxylic acid To a solution of 2-(3-bromo-1H-pyrazol-1-yl)-3-chloropyridine (i.e. the product of Step C) (30.4 g, 118 mmol) in dry tetrahydrofuran (250 mL) at −76° C. was added dropwise a solution of lithium diisopropylamide (118 mmol) in tetrahydrofuran at such a rate as to maintain the temperature below −71° C. The reaction mixture was stirred for 15 minutes at −76° C., and carbon dioxide was then bubbled through for 10 minutes, causing warming to −57° C. The reaction mixture was warmed to −20° C. and quenched with water. The reaction mixture was concentrated and then taken up in water (1 L) and ether (500 mL), and then aqueous sodium hydroxide solution (1 N, 20 mL) was added. The aqueous extracts were washed with ether and acidified with hydrochloric acid. The precipitated solids were filtered, washed with water and dried to afford the title product as a tan solid (27.7 g). (Product from another run following similar procedure melted at 200-201° C.)

$^1$H NMR (DMSO-$d_6$) δ 7.25 (s, 1H), 7.68 (dd, 1H), 8.24 (d, 1H), 8.56 (d, 1H).

Step E: Preparation of N-(2-bromo-4,6-difluorophenyl)-1-(3-chloro-2-pyridinyl)-3-bromo-1H-pyrazole-5-carboxamide Oxalyl chloride (0.043 mL, 0.5 mmol) was added to a mixture of 3-bromo-1-(3-chloro-2-pyridinyl)-1H-pyrazole-5-carboxylic acid (i.e. the product of Step D) (200 mg, 0.66 mmol) and two drops of N,N-dimethylformamide (DMF) in 30 mL of methylene chloride at room temperature and the reaction was stirred for 10 minutes. After this time a catalytic amount of 4-(dimethylamino)pyridine was added, followed by dropwise addition of a mixture of triethylamine (184 mL, 1.4 mmol) and 2-bromo-4,6-difluoroaniline in 10 mL of methylene chloride. The reaction was stirred overnight and then concentrated to near dryness. Chromatography on silica gel with hexane/ethyl acetate gradient as eluent (9:1 to 1:1) afforded an oil. The oil was then cooled in dry ice and triturated with ether/hexane to provide the title compound (0.22 g), a compound of the present invention, as a solid melting at 138-139° C.

$^1$H NMR ($CDCl_3$) δ 6.90 (m, 1H), 6.98 (s, 1H), 7.18 (m, 1H), 7.40 (dd, 1H), 7.55 (br s, 1H), 7.90 (d, 1H), 8.47 (d, 1H).

Example 3

Preparation of 1-(3-chloro-2-pyridinyl)-N-(2,4-dichlorophenyl)-3-(trifluoromethyl)-1H-pyrazole-5-carboxamide To a solution of 1-(3-chloro-2-pyridinyl)-3-(trifluoromethyl)-1H-pyrazole-5-carboxylic acid (i.e. the product from Step B in Example 1) (6.0 g, 20.76 mmol) in 60 mL of methylene chloride was added oxalyl chloride (5.7 g, 44.88 mmol) followed by two drops of DMF. The mixture was stirred for two hours after which time the reaction was concentrated on a rotary evaporator at reduced pressure, taken up in chloroform, and concentrated a second time to remove residual oxalyl chloride. The resultant acid chloride was used directly in the next step.

To a solution of 2,4-dichloroaniline (382 mg, 2.35 mmol) in 3 mL of dry tetrahydrofuran was added a solution of the acid chloride (307 mg, 1.0 mmol) in 3 mL of chloroform, and the mixture was stirred at room temperature for four hours. After this time the reaction was partitioned between chloroform and saturated aqueous sodium bicarbonate. The chloroform extracts were dried over magnesium sulfate, filtered and concentrated under reduced pressure. Chromatography on silica gel with hexane/ethyl acetate as eluent (8:1) afforded 67 mg of the title compound, a compound of the present invention, as a colorless oil.

$^1$H NMR ($CDCl_3$) δ 7.16 (s, 1H), 7.2 (m, 1H), 7.42 (s, 1H), 7.48 (dd, 1H), 7.94 (dd, 1H), 8.17 (dd, 1H), 8.38 (br s, 1H), 8.52 (dd, 1H).

Example 4

Preparation of the Amide Library of Index Table B

To a solution of 1-(3-chloro-2-pyridinyl)-3-(trifluoromethyl)-1H-pyrazole-5-carboxylic acid (i.e. the product from Step B in Example 1) (1.467 g, 6.3 mmol) in 25 mL of methylene chloride was added oxalyl chloride (2.6 mL, 37.8 mmol). After the initial gas evolution ceased, the solution was heated to reflux for 2.5 h. The mixture was then cooled to room temperature and concentrated. The resultant yellow oil residue was triturated with methylene chloride (3×25 mL) to remove traces of oxalyl chloride. A 0.1 M stock solution of this acid chloride was prepared by diluting the residue to a volume of 63 mL with methylene chloride. The stock solution was used immediately in the next step. A 0.1 M stock solution in methylene chloride of each of the anilines used in the library was prepared. A 0.83 M stock solution of triethylamine in methylene chloride containing 0.5 mg/mL of 4-(dimethylamino)pyridine was prepared. In the drybox, the aniline stock solutions (250 μL) were distributed to individual wells of a 96 well block via pipette. To each well was added the acid chloride stock solution (300 μL) followed by the triethylamine stock solution1 (50 μL). The block was then sealed, removed from the drybox and placed in a modified Flexchem® oven (Robbins Scientific Co. Sunnyvale, Calif., USA) to agitate at room temperature overnight under nitrogen atmosphere. The top of the block was then removed and trisamine resin (75 mg) was added to each well. The block was resealed and agitated overnight. The contents of the block were filtered into a 96 well microtiter plate and washed with 200 μL of methylene chloride. The combined filtrates were added to a Whatman® MBPP filter plate that had previously been prepared by charging each well with 200 mg of Hydromatrix (plus-calcined diatomaceous earth)(Varian, Inc. Walnut Creek, Calif., USA) and then hydrating with 200 μL of 0.1 M sodium hydroxide. The plate was gravity filtered into a pre-tared micronics plate and the Hydromatrix was washed with 300 μL of methylene chloride into the same plate. A sample was removed for LCMS (Liquid Chromatography Mass Spectrometry) analysis and the solvent was then removed under reduced pressure. The prepared library is reported in Index Table B. Product analysis was done by using LCMS on a Micromass LCT™ TOF (time of flight) mass spectrometer (Macromass Inc. Manchester, UK) operating in electrospray ionization mode and collecting data from 100-1200 Daltons for 9 minutes. The LC system was a Waters Alliance 2790 with a 2.1×30 mm Zorbax SB-C18 Rapid Resolution column (Waters Co. Milford, Mass., USA). A six minute linear gradient of 10% acetonitrile in water with 0.1% formic acid to 100% acetonitrile with 0.1% formic acid followed by a three minute hold was used to elute the compounds. Each injection was 3 μL of an approximately 0.5 mg/mL solution. The observed M+H (protonated molecular ion) is reported in Index Table B.

By the procedures described herein together with methods known in the art, the following compounds of Tables 1 to 7 can be prepared. The following abbreviations are used in the Tables: t is tertiary, s is secondary, n is normal, i is iso, c is cyclo, Me is methyl, Et is ethyl, Pr is propyl, i-Pr is isopropyl, t-Bu is tertiary butyl, Ph is phenyl, OMe is methoxy, OEt is ethoxy, SMe is methylthio, SEt is ethylthio, CN is cyano, $NO_2$ is nitro, TMS is trimethylsilyl, S(O)Me is methylsulfinyl, and $S(O)_2Me$ is methylsulfonyl.

TABLE 1

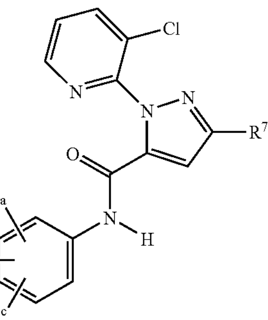

| $R^{2a}$ | $R^{2b}$ | $R^{2c}$ | $R^7$ | $R^{2a}$ | $R^{2b}$ | $R^{2c}$ | $R^7$ |
|---|---|---|---|---|---|---|---|
| H | H | H | Cl | H | H | H | Br |
| 2-F | H | H | Cl | 2-F | H | H | Br |
| 2-Cl | H | H | Cl | 2-Cl | H | H | Br |
| 2-Br | H | H | Cl | 2-Br | H | H | Br |
| 2-I | H | H | Cl | 2-I | H | H | Br |
| 2-Me | H | H | Cl | 2-Me | H | H | Br |
| 2-Et | H | H | Cl | 2-Et | H | H | Br |
| 2-$CF_3$ | H | H | Cl | 2-$CF_3$ | H | H | Br |
| 2-$OCF_2H$ | H | H | Cl | 2-$OCF_2H$ | H | H | Br |
| 2-F | 4-F | H | Cl | 2-F | 4-F | H | Br |
| 2-Cl | 4-F | H | Cl | 2-Cl | 4-F | H | Br |
| 2-Br | 4-F | H | Cl | 2-Br 4-F | H | Br | |
| 2-I | 4-F | H | Cl | 2-I | 4-F | H | Br |
| 2-Me | 4-F | H | Cl | 2-Me 4-F | H | Br | |
| 2-Et | 4-F | H | Cl | 2-Et 4-F | H | Br | |
| 2-$CF_3$ | 4-F | H | Cl | 2-$CF_3$ | 4-F | H | Br |
| 2-$OCF_2H$ | 4-F | H | Cl | 2-$OCF_2H$ | 4-F | H | Br |
| 2-F | 4-Cl | H | Cl | 2-F | 4-Cl | H | Br |
| 2-Cl | 4-Cl | H | Cl | 2-Cl | 4-Cl | H | Br |
| 2-Br | 4-Cl | H | Cl | 2-Br | 4-Cl | H | Br |

TABLE 1-continued

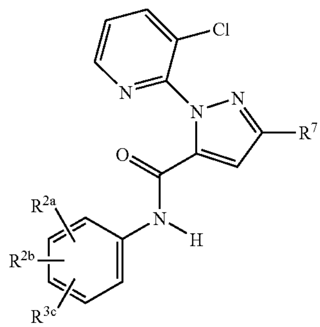

| $R^{2a}$ | $R^{2b}$ | $R^{2c}$ | $R^7$ | $R^{2a}$ | $R^{2b}$ | $R^{2c}$ | $R^7$ |
|---|---|---|---|---|---|---|---|
| 2-I | 4-Cl | H | Cl | 2-I | 4-Cl | H | Br |
| 2-Me | 4-Cl | H | Cl | 2-Me | 4-Cl | H | Br |
| 2-Et | 4-Cl | H | Cl | 2-Et | 4-Cl | H | Br |
| 2-$CF_3$ | 4-Cl | H | Cl | 2-$CF_3$ | 4-Cl | H | Br |
| 2-$OCF_2H$ | 4-Cl | H | Cl | 2-$OCF_2H$ | 4-Cl | H | Br |
| 2-F | 4-Br | H | Cl | 2-F | 4-Br | H | Br |
| 2-Cl | 4-Br | H | Cl | 2-Cl | 4-Br | H | Br |
| 2-Br | 4-Br | H | Cl | 2-Br | 4-Br | H | Br |
| 2-I | 4-Br | H | Cl | 2-I | 4-Br | H | Br |
| 2-Me | 4-Br | H | Cl | 2-Me | 4-Br | H | Br |
| 2-Et | 4-Br | H | Cl | 2-Et | 4-Br | H | Br |
| 2-$CF_3$ | 4-Br | H | Cl | 2-$CF_3$ | 4-Br | H | Br |
| 2-$OCF_2H$ | 4-Br | H | Cl | 2-$OCF_2H$ | 4-Br | H | Br |
| 2-F | 4-I | H | Cl | 2-F | 4-I | H | Br |
| 2-Cl | 4-I | H | Cl | 2-Cl | 4-I | H | Br |
| 2-Br | 4-I | H | Cl | 2-Br | 4-I | H | Br |
| 2-I | 4-I | H | Cl | 2-I | 4-I | H | Br |
| 2-Me | 4-I | H | Cl | 2-Me | 4-I | H | Br |
| 2-Et | 4-I | H | Cl | 2-Et | 4-I | H | Br |
| 2-$CF_3$ | 4-I | H | Cl | 2-$CF_3$ | 4-I | H | Br |
| 2-F | 4-$CF_3$ | H | Cl | 2-F | 4-$CF_3$ | H | Br |
| 2-Cl | 4-$CF_3$ | H | Cl | 2-Cl | 4-$CF_3$ | H | Br |
| 2-Br | 4-$CF_3$ | H | Cl | 2-Br | 4-$CF_3$ | H | Br |
| 2-I | 4-$CF_3$ | H | Cl | 2-I | 4-$CF_3$ | H | Br |
| 2-Me | 4-$CF_3$ | H | Cl | 2-Me | 4-$CF_3$ | H | Br |
| 2-Et | 4-$CF_3$ | H | Cl | 2-Et | 4-$CF_3$ | H | Br |
| 2-$CF_3$ | 4-$CF_3$ | H | Cl | 2-$CF_3$ | 4-$CF_3$ | H | Br |
| 2-F | 4-CN | H | Cl | 2-F | 4-CN | H | Br |
| 2-Cl | 4-CN | H | Cl | 2-Cl | 4-CN | H | Br |
| 2-Br | 4-CN | H | Cl | 2-Br | 4-CN | H | Br |
| 2-I | 4-CN | H | Cl | 2-I | 4-CN | H | Br |
| 2-Me | 4-CN | H | Cl | 2-Me | 4-CN | H | Br |
| 2-Et | 4-CN | H | Cl | 2-Et | 4-CN | H | Br |
| 2-$CF_3$ | 4-CN | H | Cl | 2-$CF_3$ | 4-CN | H | Br |
| 2-F | H | 6-Cl | Cl | 2-F | H | 6-Cl | Br |
| 2-Cl | H | 6-Cl | Cl | 2-Cl | H | 6-Cl | Br |
| 2-Br | H | 6-Cl | Cl | 2-Br | H | 6-Cl | Br |
| 2-I | H | 6-Cl | Cl | 2-I | H | 6-Cl | Br |
| 2-Me | H | 6-Cl | Cl | 2-Me | H | 6-Cl | Br |
| 2-Et | H | 6-Cl | Cl | 2-Et | H | 6-Cl | Br |
| 2-$CF_3$ | H | 6-Cl | Cl | 2-$CF_3$ | H | 6-Cl | Br |
| 2-$OCF_2H$ | H | 6-Cl | Cl | 2-$OCF_2H$ | H | 6-Cl | Br |
| 2-F | H | 6-Br | Cl | 2-F | H | 6-Br | Br |
| 2-Cl | H | 6-Br | Cl | 2-Cl | H | 6-Br | Br |
| 2-Br | H | 6-Br | Cl | 2-Br | H | 6-Br | Br |
| 2-I | H | 6-Br | Cl | 2-I | H | 6-Br | Br |
| 2-Me | H | 6-Br | Cl | 2-Me | H | 6-Br | Br |
| 2-Et | H | 6-Br | Cl | 2-Et | H | 6-Br | Br |
| 2-$CF_3$ | H | 6-Br | Cl | 2-$CF_3$ | H | 6-Br | Br |
| 2-$OCF_2H$ | H | 6-Br | Cl | 2-$OCF_2H$ | H | 6-Br | Br |
| 2-F | H | 6-F | Cl | 2-F | H | 6-F | Br |
| 2-Cl | H | 6-F | Cl | 2-Cl | H | 6-F | Br |
| 2-Br | H | 6-F | Cl | 2-Br | H | 6-F | Br |
| 2-I | H | 6-F | Cl | 2-I | H | 6-F | Br |
| 2-Me | H | 6-F | Cl | 2-Me | H | 6-F | Br |
| 2-Et | H | 6-F | Cl | 2-Et | H | 6-F | Br |
| 2-$CF_3$ | H | 6-F | Cl | 2-$CF_3$ | H | 6-F | Br |
| 2-$OCF_2H$ | H | 6-F | Cl | 2-$OCF_2H$ | H | 6-F | Br |
| 2-F | 4-F | 6-Cl | Cl | 2-F | 4-F | 6-Cl | Br |
| 2-Cl | 4-F | 6-Cl | Cl | 2-Cl | 4-F | 6-Cl | Br |
| 2-Br | 4-F | 6-Cl | Cl | 2-Br | 4-F | 6-Cl | Br |

TABLE 1-continued

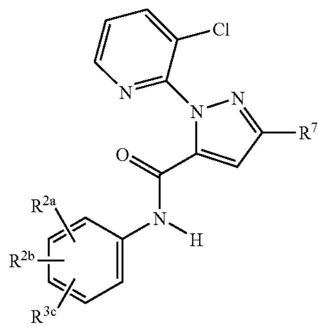

| $R^{2a}$ | $R^{2b}$ | $R^{2c}$ | $R^7$ | $R^{2a}$ | $R^{2b}$ | $R^{2c}$ | $R^7$ |
|---|---|---|---|---|---|---|---|
| 2-I | 4-F | 6-Cl | Cl | 2-I | 4-F | 6-Cl | Br |
| 2-Me | 4-F | 6-Cl | Cl | 2-Me | 4-F | 6-Cl | Br |
| 2-Et | 4-F | 6-Cl | Cl | 2-Et | 4-F | 6-Cl | Br |
| 2-CF3 4-F | 6-Cl | Cl | 2-$CF_3$ | 4-F | 6-Cl | Br | |
| 2-$OCF_2H$ | 4-F | 6-Cl | Cl | 2-$OCF_2H$ | 4-F | 6-Cl | Br |
| 2-F | 4-F | 6-Br | Cl | 2-F | 4-F | 6-Br | Br |
| 2-Cl | 4-F | 6-Br | Cl | 2-Cl | 4-F | 6-Br | Br |
| 2-Br | 4-F | 6-Br | Cl | 2-Br | 4-F | 6-Br | Br |
| 2-I | 4-F | 6-Br | Cl | 2-I | 4-F | 6-Br | Br |
| 2-Me | 4-F | 6-Br | Cl | 2-Me | 4-F | 6-Br | Br |
| 2-Et | 4-F | 6-Br | Cl | 2-Et | 4-F | 6-Br | Br |
| 2-CF3 4-F | 6-Br | Cl | 2-$CF_3$ | 4-F | 6-Br | Br | |
| 2-$OCF_2H$ | 4-F | 6-Br | Cl | 2-$OCF_2H$ | 4-F | 6-Br | Br |
| 2-F | 4-F | 6-F | Cl | 2-F | 4-F | 6-F | Br |
| 2-Cl | 4-F | 6-F | Cl | 2-Cl | 4-F | 6-F | Br |
| 2-Br | 4-F | 6-F | Cl | 2-Br | 4-F | 6-F | Br |
| 2-I | 4-F | 6-F | Cl | 2-I | 4-F | 6-F | Br |
| 2-Me | 4-F | 6-F | Cl | 2-Me | 4-F | 6-F | Br |
| 2-Et | 4-F | 6-F | Cl | 2-Et | 4-F | 6-F | Br |
| 2-$CF_3$ | 4-F | 6-F | Cl | 2-$CF_3$ | 4-F | 6-F | Br |
| 2-$OCF_2H$ | 4-F | 6-F | Cl | 2-$OCF_2H$ | 4-F | 6-F | Br |
| 2-F | 4-Cl | 6-Cl | Cl | 2-F | 4-Cl | 6-Cl | Br |
| 2-Cl | 4-Cl | 6-Cl | Cl | 2-Cl | 4-Cl | 6-Cl | Br |
| 2-Br | 4-Cl | 6-Cl | Cl | 2-Br | 4-Cl | 6-Cl | Br |
| 2-I | 4-Cl | 6-Cl | Cl | 2-I | 4-Cl | 6-Cl | Br |
| 2-Me | 4-Cl | 6-Cl | Cl | 2-Me | 4-Cl | 6-Cl | Br |
| 2-Et | 4-Cl | 6-Cl | Cl | 2-Et | 4-Cl | 6-Cl | Br |
| 2-$CF_3$ | 4-Cl | 6-Cl | Cl | 2-$CF_3$ | 4-Cl | 6-Cl | Br |
| 2-$OCF_2H$ | 4-Cl | 6-Cl | Cl | 2-$OCF_2H$ | 4-Cl | 6-Cl | Br |
| 2-F | 4-Cl | 6-Br | Cl | 2-F | 4-Cl | 6-Br | Br |
| 2-Cl | 4-Cl | 6-Br | Cl | 2-Cl | 4-Cl | 6-Br | Br |
| 2-Br | 4-Cl | 6-Br | Cl | 2-Br | 4-Cl | 6-Br | Br |
| 2-I | 4-Cl | 6-Br | Cl | 2-I | 4-Cl | 6-Br | Br |
| 2-Me | 4-Cl | 6-Br | Cl | 2-Me | 4-Cl | 6-Br | Br |
| 2-Et | 4-Cl | 6-Br | Cl | 2-Et | 4-Cl | 6-Br | Br |
| 2-$CF_3$ | 4-Cl | 6-Br | Cl | 2-$CF_3$ | 4-Cl | 6-Br | Br |
| 2-$OCF_2H$ | 4-Cl | 6-Br | Cl | 2-$OCF_2H$ | 4-Cl | 6-Br | Br |
| 2-F | 4-Cl | 6-F | Cl | 2-F | 4-Cl | 6-F | Br |
| 2-Cl | 4-Cl | 6-F | Cl | 2-Cl | 4-Cl | 6-F | Br |
| 2-Br | 4-Cl | 6-F | Cl | 2-Br | 4-Cl | 6-F | Br |
| 2-I | 4-Cl | 6-F | Cl | 2-I | 4-Cl | 6-F | Br |
| 2-Me | 4-Cl | 6-F | Cl | 2-Me | 4-Cl | 6-F | Br |
| 2-Et | 4-Cl | 6-F | Cl | 2-Et | 4-Cl | 6-F | Br |
| 2-$CF_3$ | 4-Cl | 6-F | Cl | 2-$CF_3$ | 4-Cl | 6-F | Br |
| 2-$OCF_2H$ | 4-Cl | 6-F | Cl | 2-$OCF_2H$ | 4-Cl | 6-F | Br |
| 2-F | 4-Br | 6-Cl | Cl | 2-F | 4-Br | 6-Cl | Br |
| 2-Cl | 4-Br | 6-Cl | Cl | 2-Cl | 4-Br | 6-Cl | Br |
| 2-Br | 4-Br | 6-Cl | Cl | 2-Br | 4-Br | 6-Cl | Br |
| 2-I | 4-Br | 6-Cl | Cl | 2-I | 4-Br | 6-Cl | Br |
| 2-Me | 4-Br | 6-Cl | Cl | 2-Me | 4-Br | 6-Cl | Br |
| 2-Et | 4-Br | 6-Cl | Cl | 2-Et | 4-Br | 6-Cl | Br |
| 2-$CF_3$ | 4-Br | 6-Cl | Cl | 2-$CF_3$ | 4-Br | 6-Cl | Br |
| 2-$OCF_2H$ | 4-Br | 6-Cl | Cl | 2-$OCF_2H$ | 4-Br | 6-Cl | Br |
| 2-F | 4-Br | 6-Br | Cl | 2-F | 4-Br | 6-Br | Br |
| 2-Cl | 4-Br | 6-Br | Cl | 2-Cl | 4-Br | 6-Br | Br |
| 2-Br | 4-Br | 6-Br | Cl | 2-Br | 4-Br | 6-Br | Br |
| 2-I | 4-Br | 6-Br | Cl | 2-I | 4-Br | 6-Br | Br |
| 2-Me | 4-Br | 6-Br | Cl | 2-Me | 4-Br | 6-Br | Br |
| 2-Et | 4-Br | 6-Br | Cl | 2-Et | 4-Br | 6-Br | Br |
| 2-$CF_3$ | 4-Br | 6-Br | Cl | 2-$CF_3$ | 4-Br | 6-Br | Br |
| 2-$OCF_2H$ | 4-Br | 6-Br | Cl | 2-$OCF_2H$ | 4-Br | 6-Br | Br |

TABLE 1-continued

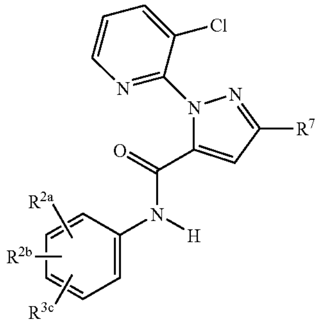

| $R^{2a}$ | $R^{2b}$ | $R^{2c}$ | $R^7$ | $R^{2a}$ | $R^{2b}$ | $R^{2c}$ | $R^7$ |
|---|---|---|---|---|---|---|---|
| 2-F | 4-Br | 6-F | Cl | 2-F | 4-Br | 6-F | Br |
| 2-Cl | 4-Br | 6-F | Cl | 2-Cl | 4-Br | 6-F | Br |
| 2-Br | 4-Br | 6-F | Cl | 2-Br | 4-Br | 6-F | Br |
| 2-I | 4-Br | 6-F | Cl | 2-I | 4-Br | 6-F | Br |
| 2-Me | 4-Br | 6-F | Cl | 2-Me | 4-Br | 6-F | Br |
| 2-Et | 4-Br | 6-F | Cl | 2-Et | 4-Br | 6-F | Br |
| 2-$CF_3$ | 4-Br | 6-F | Cl | 2-$CF_3$ | 4-Br | 6-F | Br |
| 2-$OCF_2H$ | 4-Br | 6-F | Cl | 2-$OCF_2H$ | 4-Br | 6-F | Br |
| 2-F | H | H | $CF_3$ | 2-F | H | H | $OCH_2CF_3$ |
| 2-Cl | H | H | $CF_3$ | 2-Cl | H | H | $OCH_2CF_3$ |
| 2-Br | H | H | $CF_3$ | 2-Br | H | H | $OCH_2CF_3$ |
| 2-I | H | H | $CF_3$ | 2-I | H | H | $OCH_2CF_3$ |
| 2-Me | H | H | $CF_3$ | 2-Me | H | H | $OCH_2CF_3$ |
| 2-Et | H | H | $CF_3$ | 2-Et | H | H | $QCH_2CF_3$ |
| 2-$CF_3$ | H | H | $CF_3$ | 2-$CF_3$ | H | H | $OCH_2CF_3$ |
| 2-$OCF_2H$ | H | H | $CF_3$ | 2-$OCF_2H$ | H | H | $OCH_2CF_3$ |
| 2-F | 4-F | H | $CF_3$ | 2-F | 4-F | H | $OCH_2CF_3$ |
| 2-Cl | 4-F | H | $CF_3$ | 2-Cl | 4-F | H | $OCH_2CF_3$ |
| 2-Br | 4-F | H | $CF_3$ | 2-Br | 4-F | H | $OCH_2CF_3$ |
| 2-I | 4-F | H | $CF_3$ | 2-I | 4-F | H | $OCH_2CF_3$ |
| 2-Me | 4-F | H | $CF_3$ | 2-Me | 4-F | H | $OCH_2CF_3$ |
| 2-Et | 4-F | H | $CF_3$ | 2-Et | 4-F | H | $OCH_2CF_3$ |
| 2-$CF_3$ | 4-F | H | $CF_3$ | 2-$CF_3$ | 4-F | H | $OCH_2CF_3$ |
| 2-$OCF_2H$ | 4-F | H | $CF_3$ | 2-$OCF_2H$ | 4-F | H | $OCH_2CF_3$ |
| 2-F | 4-Cl | H | $CF_3$ | 2-F | 4-Cl | H | $OCH_2CF_3$ |
| 2-Cl | 4-Cl | H | $CF_3$ | 2-Cl | 4-Cl | H | $OCH_2CF_3$ |
| 2-Br | 4-Cl | H | $CF_3$ | 2-Br | 4-Cl | H | $OCH_2CF_3$ |
| 2-I | 4-Cl | H | $CF_3$ | 2-I | 4-Cl | H | $OCH_2CF_3$ |
| 2-Me | 4-Cl | H | $CF_3$ | 2-Me | 4-Cl | H | $OCH_2CF_3$ |
| 2-Et | 4-Cl | H | $CF_3$ | 2-Et | 4-Cl | H | $OCH_2CF_3$ |
| 2-$CF_3$ | 4-Cl | H | $CF_3$ | 2-$CF_3$ | 4-Cl | H | $OCH_2CF_3$ |
| 2-$OCF_2H$ | 4-Cl | H | $CF_3$ | 2-$OCF_2H$ | 4-Cl | H | $OCH_2CF_3$ |
| 2-F | 4-Br | H | $CF_3$ | 2-F | 4-Br | H | $OCH_2CF_3$ |
| 2-Cl | 4-Br | H | $CF_3$ | 2-Cl | 4-Br | H | $OCH_2CF_3$ |
| 2-Br | 4-Br | H | $CF_3$ | 2-Br | 4-Br | H | $OCH_2CF_3$ |
| 2-I | 4-Br | H | $CF_3$ | 2-I | 4-Br | H | $OCH_2CF_3$ |
| 2-Me | 4-Br | H | $CF_3$ | 2-Me | 4-Br | H | $OCH_2CF_3$ |
| 2-Et | 4-Br | H | $CF_3$ | 2-Et | 4-Br | H | $OCH_2CF_3$ |
| 2-$CF_3$ | 4-Br | H | $CF_3$ | 2-$CF_3$ | 4-Br | H | $OCH_2CF_3$ |
| 2-$OCF_2H$ | 4-Br | H | $CF_3$ | 2-$OCF_2H$ | 4-Br | H | $OCH_2CF_3$ |
| 2-F | 4-I | H | $CF_3$ | 2-F | 4-I | H | $OCH_2CF_3$ |
| 2-Cl | 4-I | H | $CF_3$ | 2-Cl | 4-I | H | $OCH_2CF_3$ |
| 2-Br | 4-I | H | $CF_3$ | 2-Br | 4-I | H | $OCH_2CF_3$ |
| 2-I | 4-I | H | $CF_3$ | 2-I | 4-I | H | $OCH_2CF_3$ |
| 2-Me | 4-I | H | $CF_3$ | 2-Me | 4-I | H | $OCH_2CF_3$ |
| 2-Et | 4-I | H | $CF_3$ | 2-Et | 4-I | H | $OCH_2CF_3$ |
| 2-$CF_3$ | 4-I | H | $CF_3$ | 2-$CF_3$ | 4-I | H | $OCH_2CF_3$ |
| 2-F | 4-$CF_3$ | H | $CF_3$ | 2-F | 4-$CF_3$ | H | $OCH_2CF_3$ |
| 2-Cl | 4-$CF_3$ | H | $CF_3$ | 2-Cl | 4-$CF_3$ | H | $OCH_2CF_3$ |
| 2-Br | 4-$CF_3$ | H | $CF_3$ | 2-Br | 4-$CF_3$ | H | $OCH_2CF_3$ |
| 2-I | 4-$CF_3$ | H | $CF_3$ | 2-I | 4-$CF_3$ | H | $OCH_2CF_3$ |
| 2-Me | 4-$CF_3$ | H | $CF_3$ | 2-Me | 4-$CF_3$ | H | $OCH_2CF_3$ |
| 2-Et | 4-$CF_3$ | H | $CF_3$ | 2-Et | 4-$CF_3$ | H | $OCH_2CF_3$ |
| 2-$CF_3$ | 4-$CF_3$ | H | $CF_3$ | 2-$CF_3$ | 4-$CF_3$ | H | $OCH_2CF_3$ |
| 2-F | 4-CN | H | $CF_3$ | 2-F | 4-CN | H | $OCH_2CF_3$ |
| 2-Cl | 4-CN | H | $CF_3$ | 2-Cl | 4-CN | H | $OCH_2CF_3$ |
| 2-Br | 4-CN | H | $CF_3$ | 2-Br | 4-CN | H | $OCH_2CF_3$ |
| 2-I | 4-CN | H | $CF_3$ | 2-I | 4-CN | H | $OCH_2CF_3$ |
| 2-Me | 4-CN | H | $CF_3$ | 2-Me | 4-CN | H | $OCH_2CF_3$ |
| 2-Et | 4-CN | H | $CF_3$ | 2-Et | 4-CN | H | $OCH_2CF_3$ |
| 2-$CF_3$ | 4-CN | H | $CF_3$ | 2-$CF_3$ | 4-CN | H | $OCH_2CF_3$ |

TABLE 1-continued

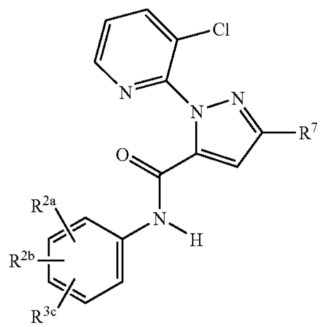

| $R^{2a}$ | $R^{2b}$ | $R^{2c}$ | $R^7$ | $R^{2a}$ | $R^{2b}$ | $R^{2c}$ | $R^7$ |
|---|---|---|---|---|---|---|---|
| 2-F | H | 6-Cl | $CF_3$ | 2-F | H | 6-Cl | $OCH_2CF_3$ |
| 2-Cl | H | 6-Cl | $CF_3$ | 2-Cl | H | 6-Cl | $OCH_2CF_3$ |
| 2-Br | H | 6-Cl | $CF_3$ | 2-Br | H | 6-Cl | $OCH_2CF_3$ |
| 2-I | H | 6-Cl | $CF_3$ | 2-I | H | 6-Cl | $OCH_2CF_3$ |
| 2-Me | H | 6-Cl | $CF_3$ | 2-Me | H | 6-Cl | $OCH_2CF_3$ |
| 2-Et | H | 6-Cl | $CF_3$ | 2-Et | H | 6-Cl | $OCH_2CF_3$ |
| 2-$CF_3$ | H | 6-Cl | $CF_3$ | 2-$CF_3$ | H | 6-Cl | $OCH_2CF_3$ |
| 2-$OCF_2H$ | H | 6-Cl | $CF_3$ | 2-$OCF_2H$ | H | 6-Cl | $OCH_2CF_3$ |
| 2-F | H | 6-Br | $CF_3$ | 2-F | H | 6-Br | $OCH_2CF_3$ |
| 2-Cl | H | 6-Br | $CF_3$ | 2-Cl | H | 6-Br | $OCH_2CF_3$ |
| 2-Br | H | 6-Br | $CF_3$ | 2-Br | H | 6-Br | $OCH_2CF_3$ |
| 2-I | H | 6-Br | $CF_3$ | 2-I | H | 6-Br | $OCH_2CF_3$ |
| 2-Me | H | 6-Br | $CF_3$ | 2-Me | H | 6-Br | $OCH_2CF_3$ |
| 2-Et | H | 6-Br | $CF_3$ | 2-Et | H | 6-Br | $OCH_2CF_3$ |
| 2-$CF_3$ | H | 6-Br | $CF_3$ | 2-$CF_3$ | H | 6-Br | $OCH_2CF_3$ |
| 2-$OCF_2H$ | H | 6-Br | $CF_3$ | 2-$OCF_2H$ | H | 6-Br | $OCH_2CF_3$ |
| 2-F | H | 6-F | $CF_3$ | 2-F | H | 6-F | $OCH_2CF_3$ |
| 2-Cl | H | 6-F | $CF_3$ | 2-Cl | H | 6-F | $OCH_2CF_3$ |
| 2-Br | H | 6-F | $CF_3$ | 2-Br | H | 6-F | $OCH_2CF_3$ |
| 2-I | H | 6-F | $CF_3$ | 2-I | H | 6-F | $OCH_2CF_3$ |
| 2-Me | H | 6-F | $CF_3$ | 2-Me | H | 6-F | $OCH_2CF_3$ |
| 2-Et | H | 6-F | $CF_3$ | 2-Et | H | 6-F | $OCH_2CF_3$ |
| 2-$CF_3$ | H | 6-F | $CF_3$ | 2-$CF_3$ | H | 6-F | $OCH_2CF_3$ |
| 2-$OCF_2H$ | H | 6-F | $CF_3$ | 2-$OCF_2H$ | H | 6-F | $OCH_2CF_3$ |
| 2-F | 4-F | 6-Cl | $CF_3$ | 2-F | 4-F | 6-Cl | $OCH_2CF_3$ |
| 2-Cl | 4-F | 6-Cl | $CF_3$ | 2-Cl | 4-F | 6-Cl | $OCH_2CF_3$ |
| 2-Br | 4-F | 6-Cl | $CF_3$ | 2-Br | 4-F | 6-Cl | $OCH_2CF_3$ |
| 2-I | 4-F | 6-Cl | $CF_3$ | 2-I | 4-F | 6-Cl | $OCH_2CF_3$ |
| 2-Me | 4-F | 6-Cl | $CF_3$ | 2-Me | 4-F | 6-Cl | $OCH_2CF_3$ |
| 2-Et | 4-F | 6-Cl | $CF_3$ | 2-Et | 4-F | 6-Cl | $OCH_2CF_3$ |
| 2-$CF_3$ | 4-F | 6-Cl | $CF_3$ | 2-$CF_3$ | 4-F | 6-Cl | $OCH_2CF_3$ |
| 2-$OCF_2H$ | 4-F | 6-Cl | $CF_3$ | 2-$OCF_2H$ | 4-F | 6-Cl | $OCH_2CF_3$ |
| 2-F | 4-F | 6-Br | $CF_3$ | 2-F | 4-F | 6-Br | $OCH_2CF_3$ |
| 2-Cl | 4-F | 6-Br | $CF_3$ | 2-Cl | 4-F | 6-Br | $OCH_2CF_3$ |
| 2-Br | 4-F | 6-Br | $CF_3$ | 2-Br | 4-F | 6-Br | $OCH_2CF_3$ |
| 2-I | 4-F | 6-Br | $CF_3$ | 2-I | 4-F | 6-Br | $OCH_2CF_3$ |
| 2-Me | 4-F | 6-Br | $CF_3$ | 2-Me | 4-F | 6-Br | $OCH_2CF_3$ |
| 2-Et | 4-F | 6-Br | $CF_3$ | 2-Et | 4-F | 6-Br | $OCH_2CF_3$ |
| 2-$CF_3$ | 4-F | 6-Br | $CF_3$ | 2-$CF_3$ | 4-F | 6-Br | $OCH_2CF_3$ |
| 2-$OCF_2H$ | 4-F | 6-Br | $CF_3$ | 2-$OCF_2H$ | 4-F | 6-Br | $OCH_2CF_3$ |
| 2-F | 4-F | 6-F | $CF_3$ | 2-F | 4-F | 6-F | $OCH_2CF_3$ |
| 2-Cl | 4-F | 6-F | $CF_3$ | 2-Cl | 4-F | 6-F | $OCH_2CF_3$ |
| 2-Br | 4-F | 6-F | $CF_3$ | 2-Br | 4-F | 6-F | $OCH_2CF_3$ |
| 2-I | 4-F | 6-F | $CF_3$ | 2-I | 4-F | 6-F | $OCH_2CF_3$ |
| 2-Me | 4-F | 6-F | $CF_3$ | 2-Me | 4-F | 6-F | $OCH_2CF_3$ |
| 2-Et | 4-F | 6-F | $CF_3$ | 2-Et | 4-F | 6-F | $OCH_2CF_3$ |
| 2-$CF_3$ | 4-F | 6-F | $CF_3$ | 2-$CF_3$ | 4-F | 6-F | $OCH_2CF_3$ |
| 2-$OCF_2H$ | 4-F | 6-F | $CF_3$ | 2-$OCF_2H$ | 4-F | 6-F | $OCH_2CF_3$ |
| 2-F | 4-Cl | 6-Cl | $CF_3$ | 2-F | 4-Cl | 6-Cl | $OCH_2CF_3$ |
| 2-Cl | 4-Cl | 6-Cl | $CF_3$ | 2-Cl | 4-Cl | 6-Cl | $OCH_2CF_3$ |
| 2-Br | 4-Cl | 6-Cl | $CF_3$ | 2-Br | 4-Cl | 6-Cl | $OCH_2CF_3$ |
| 2-I | 4-Cl | 6-Cl | $CF_3$ | 2-I | 4-Cl | 6-Cl | $OCH_2CF_3$ |
| 2-Me | 4-Cl | 6-Cl | $CF_3$ | 2-Me | 4-Cl | 6-Cl | $OCH_2CF_3$ |
| 2-Et | 4-Cl | 6-Cl | $CF_3$ | 2-Et | 4-Cl | 6-Cl | $OCH_2CF_3$ |
| 2-$CF_3$ | 4-Cl | 6-Cl | $CF_3$ | 2-$CF_3$ | 4-Cl | 6-Cl | $OCH_2CF_3$ |
| 2-$OCF_2H$ | 4-Cl | 6-Cl | $CF_3$ | 2-$OCF_2H$ | 4-Cl | 6-Cl | $OCH_2CF_3$ |
| 2-F | 4-Cl | 6-Br | $CF_3$ | 2-F | 4-Cl | 6-Br | $OCH_2CF_3$ |
| 2-Cl | 4-Cl | 6-Br | $CF_3$ | 2-Cl | 4-Cl | 6-Br | $OCH_2CF_3$ |
| 2-Br | 4-Cl | 6-Br | $CF_3$ | 2-Br | 4-Cl | 6-Br | $OCH_2CF_3$ |
| 2-I | 4-Cl | 6-Br | $CF_3$ | 2-I | 4-Cl | 6-Br | $OCH_2CF_3$ |
| 2-Me | 4-Cl | 6-Br | $CF_3$ | 2-Me | 4-Cl | 6-Br | $OCH_2CF_3$ |

TABLE 1-continued

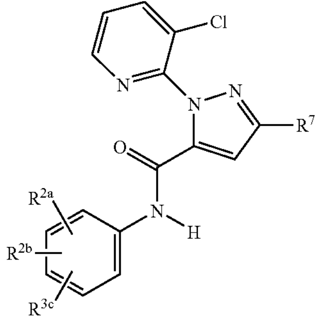

| $R^{2a}$ | $R^{2b}$ | $R^{2c}$ | $R^7$ | $R^{2a}$ | $R^{2b}$ | $R^{2c}$ | $R^7$ |
|---|---|---|---|---|---|---|---|
| 2-Et | 4-Cl | 6-Br | $CF_3$ | 2-Et | 4-Cl | 6-Br | $OCH_2CF_3$ |
| 2-$CF_3$ | 4-Cl | 6-Br | $CF_3$ | 2-$CF_3$ | 4-Cl | 6-Br | $OCH_2CF_3$ |
| 2-$OCF_2H$ | 4-Cl | 6-Br | $CF_3$ | 2-$OCF_2H$ | 4-Cl | 6-Br | $OCH_2CF_3$ |
| 2-F | 4-Cl | 6-F | $CF_3$ | 2-F | 4-Cl | 6-F | $OCH_2CF_3$ |
| 2-Cl | 4-Cl | 6-F | $CF_3$ | 2-Cl | 4-Cl | 6-F | $OCH_2CF_3$ |
| 2-Br | 4-Cl | 6-F | $CF_3$ | 2-Br | 4-Cl | 6-F | $OCH_2CF_3$ |
| 2-I | 4-Cl | 6-F | $CF_3$ | 2-I | 4-Cl | 6-F | $OCH_2CF_3$ |
| 2-Me | 4-Cl | 6-F | $CF_3$ | 2-Me | 4-Cl | 6-F | $OCH_2CF_3$ |
| 2-Et | 4-Cl | 6-F | $CF_3$ | 2-Et | 4-Cl | 6-F | $OCH_2CF_3$ |
| 2-$CF_3$ | 4-Cl | 6-F | $CF_3$ | 2-$CF_3$ | 4-Cl | 6-F | $OCH_2CF_3$ |
| 2-$OCF_2H$ | 4-Cl | 6-F | $CF_3$ | 2-$OCF_2H$ | 4-Cl | 6-F | $OCH_2CF_3$ |
| 2-F | 4-Br | 6-Cl | $CF_3$ | 2-F | 4-Br | 6-Cl | $OCH_2CF_3$ |
| 2-Cl | 4-Br | 6-Cl | $CF_3$ | 2-Cl | 4-Br | 6-Cl | $OCH_2CF_3$ |
| 2-Br | 4-Br | 6-Cl | $CF_3$ | 2-Br | 4-Br | 6-Cl | $OCH_2CF_3$ |
| 2-I | 4-Br | 6-Cl | $CF_3$ | 2-I | 4-Br | 6-Cl | $OCH_2CF_3$ |
| 2-Me | 4-Br | 6-Cl | $CF_3$ | 2-Me | 4-Br | 6-Cl | $OCH_2CF_3$ |
| 2-Et | 4-Br | 6-Cl | $CF_3$ | 2-Et | 4-Br | 6-Cl | $OCH_2CF_3$ |
| 2-$CF_3$ | 4-Br | 6-Cl | $CF_3$ | 2-$CF_3$ | 4-Br | 6-Cl | $OCH_2CF_3$ |
| 2-$OCF_2H$ | 4-Br | 6-Cl | $CF_3$ | 2-$OCF_2H$ | 4-Br | 6-Cl | $OCH_2CF_3$ |
| 2-F | 4-Br | 6-Br | $CF_3$ | 2-F | 4-Br | 6-Br | $OCH_2CF_3$ |
| 2-Cl | 4-Br | 6-Br | $CF_3$ | 2-Cl | 4-Br | 6-Br | $OCH_2CF_3$ |
| 2-Br | 4-Br | 6-Br | $CF_3$ | 2-Br | 4-Br | 6-Br | $OCH_2CF_3$ |
| 2-I | 4-Br | 6-Br | $CF_3$ | 2-I | 4-Br | 6-Br | $OCH_2CF_3$ |
| 2-Me | 4-Br | 6-Br | $CF_3$ | 2-Me | 4-Br | 6-Br | $OCH_2CF_3$ |
| 2-Et | 4-Br | 6-Br | $CF_3$ | 2-Et | 4-Br | 6-Br | $OCH_2CF_3$ |
| 2-$CF_3$ | 4-Br | 6-Br | $CF_3$ | 2-$CF_3$ | 4-Br | 6-Br | $OCH_2CF_3$ |
| 2-$OCF_2H$ | 4-Br | 6-Br | $CF_3$ | 2-$OCF_2H$ | 4-Br | 6-Br | $OCH_2CF_3$ |
| 2-F | 4-Br | 6-F | $CF_3$ | 2-F | 4-Br | 6-F | $OCH_2CF_3$ |
| 2-Cl | 4-Br | 6-F | $CF_3$ | 2-Cl | 4-Br | 6-F | $OCH_2CF_3$ |
| 2-Br | 4-Br | 6-F | $CF_3$ | 2-Br | 4-Br | 6-F | OCII2CF3 |
| 2-I | 4-Br | 6-F | $CF_3$ | 2-I | 4-Br | 6-F | $OCH_2CF_3$ |
| 2-Me | 4-Br | 6-F | $CF_3$ | 2-Me | 4-Br | 6-F | $OCH_2CF_3$ |
| 2-Et | 4-Br | 6-F | $CF_3$ | 2-Et | 4-Br | 6-F | $OCH_2CF_3$ |
| 2-$CF_3$ | 4-Br | 6-F | $CF_3$ | 2-$CF_3$ | 4-Br | 6-F | $OCH_2CF_3$ |
| 2-$OCF_2H$ | 4-Br | 6-F | $CF_3$ | 2-$OCF_2H$ | 4-Br | 6-F | $OCH_2CF_3$ |

TABLE 2

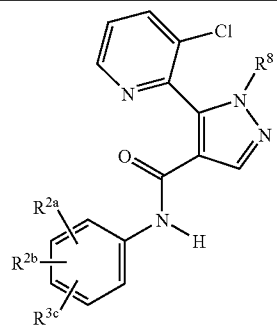

| $R^{2a}$ | $R^{2b}$ | $R^{2c}$ | $R^7$ | $R^{2a}$ | $R^{2b}$ | $R^{2c}$ | $R^7$ |
|---|---|---|---|---|---|---|---|
| H | H | H | Me | H | H | H | $OCH_2CF_3$ |
| 2-F | H | H | Me | 2-F | H | H | $OCH_2CF_3$ |

TABLE 2-continued

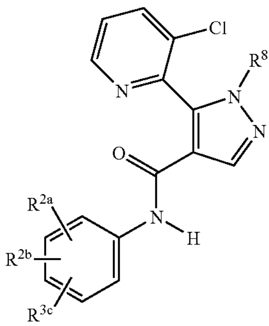

| $R^{2a}$ | $R^{2b}$ | $R^{2c}$ | $R^7$ | $R^{2a}$ | $R^{2b}$ | $R^{2c}$ | $R^7$ |
|---|---|---|---|---|---|---|---|
| 2-Cl | H | H | Me | 2-Cl | H | H | $OCH_2CF_3$ |
| 2-Br | H | H | Me | 2-Br | H | H | $OCH_2CF_3$ |
| 2-I | H | H | Me | 2-I | H | H | $OCH_2CF_3$ |
| 2-Me | H | H | Me | 2-Me | H | H | $OCH_2CF_3$ |
| 2-Et | H | H | Me | 2-Et | H | H | $OCH_2CF_3$ |
| 2-$CF_3$ | H | H | Me | 2-$CF_3$ | H | H | $OCH_2CF_3$ |
| 2-$OCF_2H$ | H | H | Me | 2-$OCF_2H$ | H | H | $OCH_2CF_3$ |
| 2-F | 4-F | H | Me | 2-F | 4-F | H | $OCH_2CF_3$ |
| 2-Cl | 4-F | H | Me | 2-Cl | 4-F | H | $OCH_2CF_3$ |
| 2-Br | 4-F | H | Me | 2-Br | 4-F | H | $OCH_2CF_3$ |
| 2-I | 4-F | H | Me | 2-I | 4-F | H | $OCH_2CF_3$ |
| 2-Me | 4-F | H | Me | 2-Me | 4-F | H | $OCH_2CF_3$ |
| 2-Et | 4-F | H | Me | 2-Et | 4-F | H | $OCH_2CF_3$ |
| 2-$CF_3$ | 4-F | H | Me | 2-$CF_3$ | 4-F | H | $OCH_2CF_3$ |
| 2-$OCF_2H$ | 4-F | H | Me | 2-$OCF_2H$ | 4-F | H | $OCH_2CF_3$ |
| 2-F | 4-Cl | H | Me | 2-F | 4-Cl | H | $OCH_2CF_3$ |
| 2-Cl | 4-Cl | H | Me | 2-Cl | 4-Cl | H | $OCH_2CF_3$ |
| 2-Br | 4-Cl | H | Me | 2-Br | 4-Cl | H | $OCH_2CF_3$ |
| 2-I | 4-Cl | H | Me | 2-I | 4-Cl | H | $OCH_2CF_3$ |
| 2-Me | 4-Cl | H | Me | 2-Me | 4-Cl | H | $OCH_2CF_3$ |
| 2-Et | 4-Cl | H | Me | 2-Et | 4-Cl | H | $OCH_2CF_3$ |
| 2-$CF_3$ | 4-Cl | H | Me | 2-$CF_3$ | 4-Cl | H | $OCH_2CF_3$ |
| 2-$OCF_2H$ | 4-Cl | H | Me | 2-$OCF_2H$ | 4-Cl | H | $OCH_2CF_3$ |
| 2-F | 4-Br | H | Me | 2-F | 4-Br | H | $OCH_2CF_3$ |
| 2-Cl | 4-Br | H | Me | 2-Cl | 4-Br | H | $OCH_2CF_3$ |
| 2-Br | 4-Br | H | Me | 2-Br | 4-Br | H | $OCH_2CF_3$ |
| 2-I | 4-Br | H | Me | 2-I | 4-Br | H | $OCH_2CF_3$ |
| 2-Me | 4-Br | H | Me | 2-Me | 4-Br | H | $OCH_2CF_3$ |
| 2-Et | 4-Br | H | Me | 2-Et | 4-Br | H | $OCH_2CF_3$ |
| 2-$CF_3$ | 4-Br | H | Me | 2-$CF_3$ | 4-Br | H | $OCH_2CF_3$ |
| 2-$OCF_2H$ | 4-Br | H | Me | 2-$OCF_2H$ | 4-Br | H | $OCH_2CF_3$ |
| 2-F | 4-I | H | Me | 2-F | 4-I | H | $OCH_2CF_3$ |
| 2-Cl | 4-I | H | Me | 2-Cl | 4-I | H | $OCH_2CF_3$ |
| 2-Br | 4-I | H | Me | 2-Br | 4-I | H | $OCH_2CF_3$ |
| 2-I | 4-I | H | Me | 2-I | 4-I | H | $OCH_2CF_3$ |
| 2-Me | 4-I | H | Me | 2-Me | 4-I | H | $OCH_2CF_3$ |
| 2-Et | 4-I | H | Me | 2-Et | 4-I | H | $OCH_2CF_3$ |
| 2-$CF_3$ | 4-I | H | Me | 2-$CF_3$ | 4-I | H | $OCH_2CF_3$ |
| 2-F | 4-$CF_3$ | H | Me | 2-F | 4-$CF_3$ | H | $OCH_2CF_3$ |
| 2-Cl | 4-$CF_3$ | H | Me | 2-Cl | 4-$CF_3$ | H | $OCH_2CF_3$ |
| 2-Br | 4-$CF_3$ | H | Me | 2-Br | 4-$CF_3$ | H | $OCH_2CF_3$ |
| 2-I | 4-$CF_3$ | H | Me | 2-I | 4-$CF_3$ | H | $OCH_2CF_3$ |
| 2-Me | 4-$CF_3$ | H | Me | 2-Me | 4-$CF_3$ | H | $OCH_2CF_3$ |
| 2-Et | 4-$CF_3$ | H | Me | 2-Et | 4-$CF_3$ | H | $OCH_2CF_3$ |
| 2-$CF_3$ | 4-$CF_3$ | H | Me | 2-$CF_3$ | 4-$CF_3$ | H | $OCH_2CF_3$ |
| 2-F | 4-CN | H | Me | 2-F | 4-CN | H | $OCH_2CF_3$ |
| 2-Cl | 4-CN | H | Me | 2-Cl | 4-CN | H | $OCH_2CF_3$ |
| 2-Br | 4-CN | H | Me | 2-Br | 4-CN | H | $OCH_2CF_3$ |
| 2-I | 4-CN | H | Me | 2-I | 4-CN | H | $OCH_2CF_3$ |
| 2-Me | 4-CN | H | Me | 2-Me | 4-CN | H | $OCH_2CF_3$ |
| 2-Et | 4-CN | H | Me | 2-Et | 4-CN | H | $OCH_2CF_3$ |
| 2-$CF_3$ | 4-CN | H | Me | 2-$CF_3$ | 4-CN | H | $OCH_2CF_3$ |
| 2-F | H | 6-Cl | Me | 2-F | H | 6-Cl | $OCH_2CF_3$ |
| 2-Cl | H | 6-Cl | Me | 2-Cl | H | 6-Cl | $OCH_2CF_3$ |
| 2-Br | H | 6-Cl | Me | 2-Br | H | 6-Cl | $OCH_2CF_3$ |
| 2-I | H | 6-Cl | Me | 2-I | H | 6-Cl | $OCH_2CF_3$ |
| 2-Me | H | 6-Cl | Me | 2-Me | H | 6-Cl | $OCH_2CF_3$ |

TABLE 2-continued

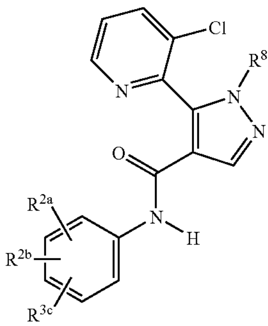

| $R^{2a}$ | $R^{2b}$ | $R^{2c}$ | $R^7$ | $R^{2a}$ | $R^{2b}$ | $R^{2c}$ | $R^7$ |
|---|---|---|---|---|---|---|---|
| 2-Et | H | 6-Cl | Me | 2-Et | H | 6-Cl | $OCH_2CF_3$ |
| 2-$CF_3$ | H | 6-Cl | Me | 2-$CF_3$ | H | 6-Cl | $OCH_2CF_3$ |
| 2-$OCF_2H$ | H | 6-Cl | Me | 2-$OCF_2H$ | H | 6-Cl | $OCH_2CF_3$ |
| 2-F | H | 6-Br | Me | 2-F | H | 6-Br | $OCH_2CF_3$ |
| 2-Cl | H | 6-Br | Me | 2-Cl | H | 6-Br | $OCH_2CF_3$ |
| 2-Br | H | 6-Br | Me | 2-Br | H | 6-Br | $OCH_2CF_3$ |
| 2-I | H | 6-Br | Me | 2-I | H | 6-Br | $OCH_2CF_3$ |
| 2-Me | H | 6-Br | Me | 2-Me | H | 6-Br | $OCH_2CF_3$ |
| 2-Et | H | 6-Br | Me | 2-Et | H | 6-Br | $OCH_2CF_3$ |
| 2-$CF_3$ | H | 6-Br | Me | 2-$CF_3$ | H | 6-Br | $OCH_2CF_3$ |
| 2-$OCF_2H$ | H | 6-Br | Me | 2-$OCF_2H$ | H | 6-Br | $OCH_2CF_3$ |
| 2-F | H | 6-F | Me | 2-F | H | 6-F | $OCH_2CF_3$ |
| 2-Cl | H | 6-F | Me | 2-Cl | H | 6-F | $OCH_2CF_3$ |
| 2-Br | H | 6-F | Me | 2-Br | H | 6-F | $OCH_2CF_3$ |
| 2-I | H | 6-F | Me | 2-I | H | 6-F | $OCH_2CF_3$ |
| 2-Me | H | 6-F | Me | 2-Me | H | 6-F | $OCH_2CF_3$ |
| 2-Et | H | 6-F | Me | 2-Et | H | 6-F | $OCH_2CF_3$ |
| 2-$CF_3$ | II | 6-F | Me | 2-$CF_3$ | H | 6-F | $OCH_2CF_3$ |
| 2-$OCF_2H$ | H | 6-F | Me | 2-$OCF_2H$ | H | 6-F | $OCH_2CF_3$ |
| 2-F | 4-F | 6-Cl | Me | 2-F | 4-F | 6-Cl | $OCH_2CF_3$ |
| 2-Cl | 4-F | 6-Cl | Me | 2-Cl | 4-F | 6-Cl | $OCH_2CF_3$ |
| 2-Br | 4-F | 6-Cl | Me | 2-Br | 4-F | 6-Cl | $OCH_2CF_3$ |
| 2-I | 4-F | 6-Cl | Me | 2-I | 4-F | 6-Cl | $OCH_2CF_3$ |
| 2-Me | 4-F | 6-Cl | Me | 2-Me | 4-F | 6-Cl | $OCH_2CF_3$ |
| 2-Et | 4-F | 6-Cl | Me | 2-Et | 4-F | 6-Cl | $OCH_2CF_3$ |
| 2-$CF_3$ | 4-F | 6-Cl | Me | 2-$CF_3$ | 4-F | 6-Cl | $OCH_2CF_3$ |
| 2-$OCF_2H$ | 4-F | 6-Cl | Me | 2-$OCF_2H$ | 4-F | 6-Cl | $OCH_2CF_3$ |
| 2-F | 4-F | 6-Br | Me | 2-F | 4-F | 6-Br | $OCH_2CF_3$ |
| 2-Cl | 4-F | 6-Br | Me | 2-Cl | 4-F | 6-Br | $OCH_2CF_3$ |
| 2-Br | 4-F | 6-Br | Me | 2-Br | 4-F | 6-Br | $OCH_2CF_3$ |
| 2-I | 4-F | 6-Br | Me | 2-I | 4-F | 6-Br | $OCH_2CF_3$ |
| 2-Me | 4-F | 6-Br | Me | 2-Me | 4-F | 6-Br | $OCH_2CF_3$ |
| 2-Et | 4-F | 6-Br | Me | 2-Et | 4-F | 6-Br | $OCH_2CF_3$ |
| 2-$CF_3$ | 4-F | 6-Br | Me | 2-$CF_3$ | 4-F | 6-Br | $OCH_2CF_3$ |
| 2-$OCF_2H$ | 4-F | 6-Br | Me | 2-$OCF_2H$ | 4-F | 6-Br | $OCH_2CF_3$ |
| 2-F | 4-F | 6-F | Me | 2-F | 4-F | 6-F | $OCH_2CF_3$ |
| 2-Cl | 4-F | 6-F | Me | 2-Cl | 4-F | 6-F | $OCH_2CF_3$ |
| 2-Br | 4-F | 6-F | Me | 2-Br | 4-F | 6-F | $OCH_2CF_3$ |
| 2-I | 4-F | 6-F | Me | 2-I | 4-F | 6-F | $OCH_2CF_3$ |
| 2-Me | 4-F | 6-F | Me | 2-Me | 4-F | 6-F | $OCH_2CF_3$ |
| 2-Et | 4-F | 6-F | Me | 2-Et | 4-F | 6-F | $OCH_2CF_3$ |
| 2-$CF_3$ | 4-F | 6-F | Me | 2-$CF_3$ | 4-F | 6-F | $OCH_2CF_3$ |
| 2-$OCF_2H$ | 4-F | 6-F | Me | 2-$OCF_2H$ | 4-F | 6-F | $OCH_2CF_3$ |
| 2-F | 4-Cl | 6-Cl | Me | 2-F | 4-Cl | 6-Cl | $OCH_2CF_3$ |
| 2-Cl | 4-Cl | 6-Cl | Me | 2-Cl | 4-Cl | 6-Cl | $OCH_2CF_3$ |
| 2-Br | 4-Cl | 6-Cl | Me | 2-Br | 4-Cl | 6-Cl | $OCH_2CF_3$ |
| 2-I | 4-Cl | 6-Cl | Me | 2-I | 4-Cl | 6-Cl | $OCH_2CF_3$ |
| 2-Me | 4-Cl | 6-Cl | Me | 2-Me | 4-Cl | 6-Cl | $OCH_2CF_3$ |
| 2-Et | 4-Cl | 6-Cl | Me | 2-Et | 4-Cl | 6-Cl | $OCH_2CF_3$ |
| 2-$CF_3$ | 4-Cl | 6-Cl | Me | 2-$CF_3$ | 4-Cl | 6-Cl | $OCH_2CF_3$ |
| 2-$OCF_2H$ | 4-Cl | 6-Cl | Me | 2-$OCF_2H$ | 4-Cl | 6-Cl | $OCH_2CF_3$ |
| 2-F | 4-Cl | 6-Br | Me | 2-F | 4-Cl | 6-Br | $OCH_2CF_3$ |
| 2-Cl | 4-Cl | 6-Br | Me | 2-Cl | 4-Cl | 6-Br | $OCH_2CF_3$ |
| 2-Br | 4-Cl | 6-Br | Me | 2-Br | 4-Cl | 6-Br | $OCH_2CF_3$ |
| 2-I | 4-Cl | 6-Br | Me | 2-I | 4-Cl | 6-Br | $OCH_2CF_3$ |
| 2-Me | 4-Cl | 6-Br | Me | 2-Me | 4-Cl | 6-Br | $OCH_2CF_3$ |

TABLE 2-continued

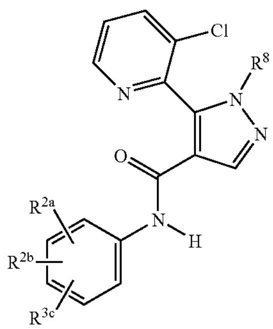

| $R^{2a}$ | $R^{2b}$ | $R^{2c}$ | $R^7$ | $R^{2a}$ | $R^{2b}$ | $R^{2c}$ | $R^7$ |
|---|---|---|---|---|---|---|---|
| 2-Et | 4-Cl | 6-Br | Me | 2-Et | 4-Cl | 6-Br | $OCH_2CF_3$ |
| 2-$CF_3$ | 4-Cl | 6-Br | Me | 2-$CF_3$ | 4-Cl | 6-Br | $OCH_2CF_3$ |
| 2-$OCF_2H$ | 4-Cl | 6-Br | Me | 2-$OCF_2H$ | 4-Cl | 6-Br | $OCH_2CF_3$ |
| 2-F | 4-Cl | 6-F | Me | 2-F | 4-Cl | 6-F | $OCH_2CF_3$ |
| 2-Cl | 4-Cl | 6-F | Me | 2-Cl | 4-Cl | 6-F | $OCH_2CF_3$ |
| 2-Br | 4-Cl | 6-F | Me | 2-Br | 4-Cl | 6-F | $OCH_2CF_3$ |
| 2-I | 4-Cl | 6-F | Me | 2-I | 4-Cl | 6-F | $OCH_2CF_3$ |
| 2-Me | 4-Cl | 6-F | Me | 2-Me | 4-Cl | 6-F | $OCH_2CF_3$ |
| 2-Et | 4-Cl | 6-F | Me | 2-Et | 4-Cl | 6-F | $OCH_2CF_3$ |
| 2-$CF_3$ | 4-Cl | 6-F | Me | 2-$CF_3$ | 4-Cl | 6-F | $OCH_2CF_3$ |
| 2-$OCF_2H$ | 4-Cl | 6-F | Me | 2-$OCF_2H$ | 4-Cl | 6-F | $OCH_2CF_3$ |
| 2-F | 4-Br | 6-Cl | Me | 2-F | 4-Br | 6-Cl | $OCH_2CF_3$ |
| 2-Cl | 4-Br | 6-Cl | Me | 2-Cl | 4-Br | 6-Cl | $OCH_2CF_3$ |
| 2-Br | 4-Br | 6-Cl | Me | 2-Br | 4-Br | 6-Cl | $OCH_2CF_3$ |
| 2-I | 4-Br | 6-Cl | Me | 2-I | 4-Br | 6-Cl | $OCH_2CF_3$ |
| 2-Me | 4-Br | 6-Cl | Me | 2-Me | 4-Br | 6-Cl | $OCH_2CF_3$ |
| 2-Et | 4-Br | 6-Cl | Me | 2-Et | 4-Br | 6-Cl | $OCH_2CF_3$ |
| 2-$CF_3$ | 4-Br | 6-Cl | Me | 2-$CF_3$ | 4-Br | 6-Cl | $OCH_2CF_3$ |
| 2-$OCF_2H$ | 4-Br | 6-Cl | Me | 2-$OCF_2H$ | 4-Br | 6-Cl | $OCH_2CF_3$ |
| 2-F | 4-Br | 6-Br | Me | 2-F | 4-Br | 6-Br | $OCH_2CF_3$ |
| 2-Cl | 4-Br | 6-Br | Me | 2-Cl | 4-Br | 6-Br | $OCH_2CF_3$ |
| 2-Br | 4-Br | 6-Br | Me | 2-Br | 4-Br | 6-Br | $OCH_2CF_3$ |
| 2-I | 4-Br | 6-Br | Me | 2-I | 4-Br | 6-Br | $OCH_2CF_3$ |
| 2-Me | 4-Br | 6-Br | Me | 2-Me | 4-Br | 6-Br | $OCH_2CF_3$ |
| 2-Et | 4-Br | 6-Br | Me | 2-Et | 4-Br | 6-Br | $OCH_2CF_3$ |
| 2-$CF_3$ | 4-Br | 6-Br | Me | 2-$CF_3$ | 4-Br | 6-Br | $OCH_2CF_3$ |
| 2-$OCF_2H$ | 4-Br | 6-Br | Me | 2-$OCF_2H$ | 4-Br | 6-Br | $OCH_2CF_3$ |
| 2-F | 4-Br | 6-F | Me | 2-F | 4-Br | 6-F | $OCH_2CF_3$ |
| 2-Cl | 4-Br | 6-F | Me | 2-Cl | 4-Br | 6-F | $OCH_2CF_3$ |
| 2-Br | 4-Br | 6-F | Me | 2-Br | 4-Br | 6-F | $OCH_2CF_3$ |
| 2-I | 4-Br | 6-F | Me | 2-I | 4-Br | 6-F | $OCH_2CF_3$ |
| 2-Me | 4-Br | 6-F | Me | 2-Me | 4-Br | 6-F | $OCH_2CF_3$ |
| 2-Et | 4-Br | 6-F | Me | 2-Et | 4-Br | 6-F | $OCH_2CF_3$ |
| 2-$CF_3$ | 4-Br | 6-F | Me | 2-$CF_3$ | 4-Br | 6-F | $OCH_2CF_3$ |
| 2-$OCF_2H$ | 4-Br | 6-F | Me | 2-$OCF_2H$ | 4-Br | 6-F | $OCH_2CF_3$ |
| 2-F | H | H | $CHF_2$ | 2-$CF_3$ | H | 6-F | $CHF_2$ |
| 2-Cl | H | H | $CHF_2$ | 2-$OCF_2H$ | H | 6-F | $CHF_2$ |
| 2-Br | H | H | $CHF_2$ | 2-F | 4-F | 6-Cl | $CHF_2$ |
| 2-I | H | H | $CHF_2$ | 2-Cl | 4-F | 6-Cl | $CHF_2$ |
| 2-Me | H | H | $CHF_2$ | 2-Br | 4-F | 6-Cl | $CHF_2$ |
| 2-Et | H | H | $CHF_2$ | 2-I | 4-F | 6-Cl | ClIP2 |
| 2-$CF_3$ | H | H | $CHF_2$ | 2-Me | 4-F | 6-Cl | $CHF_2$ |
| 2-$OCF_2H$ | H | H | $CHF_2$ | 2-Et | 4-F | 6-Cl | $CHF_2$ |
| 2-F | 4-F | H | $CHF_2$ | 2-$CF_3$ | 4-F | 6-Cl | $CHF_2$ |
| 2-Cl | 4-F | H | $CHF_2$ | 2-$OCF_2H$ | 4-F | 6-Cl | $CHF_2$ |
| 2-Br | 4-F | H | $CHF_2$ | 2-F | 4-F | 6-Br | $CHF_2$ |
| 2-I | 4-F | H | $CHF_2$ | 2-Cl | 4-F | 6-Br | $CHF_2$ |
| 2-Me | 4-F | H | $CHF_2$ | 2-Br | 4-F | 6-Br | $CHF_2$ |
| 2-Et | 4-F | H | $CHF_2$ | 2-I | 4-F | 6-Br | $CHF_2$ |
| 2-$CF_3$ | 4-F | H | $CHF_2$ | 2-Me | 4-F | 6-Br | $CHF_2$ |
| 2-$OCF_2H$ | 4-F | H | $CHF_2$ | 2-Et | 4-F | 6-Br | $CHF_2$ |
| 2-F | 4-Cl | H | $CHF_2$ | 2-$CF_3$ | 4-F | 6-Br | $CHF_2$ |
| 2-Cl | 4-Cl | H | $CHF_2$ | 2-$OCF_2H$ | 4-F | 6-Br | $CHF_2$ |
| 2-Br | 4-Cl | H | $CHF_2$ | 2-F | 4-F | 6-F | $CHF_2$ |
| 2-I | 4-Cl | H | $CHF_2$ | 2-Cl | 4-F | 6-F | $CHF_2$ |
| 2-Me | 4-Cl | H | $CHF_2$ | 2-Br | 4-F | 6-F | $CHF_2$ |

TABLE 2-continued

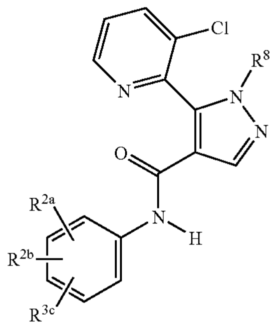

| $R^{2a}$ | $R^{2b}$ | $R^{2c}$ | $R^7$ | $R^{2a}$ | $R^{2b}$ | $R^{2c}$ | $R^7$ |
|---|---|---|---|---|---|---|---|
| 2-Et | 4-Cl | H | $CHF_2$ | 2-I | 4-F | 6-F | $CHF_2$ |
| 2-$CF_3$ | 4-Cl | H | $CHF_2$ | 2-Me | 4-F | 6-F | $CHF_2$ |
| 2-$OCF_2H$ | 4-Cl | H | $CHF_2$ | 2-Et | 4-F | 6-F | $CHF_2$ |
| 2-F | 4-Br | H | $CHF_2$ | 2-$CF_3$ | 4-F | 6-F | $CHF_2$ |
| 2-Cl | 4-Br | H | $CHF_2$ | 2-$OCF_2H$ | 4-F | 6-F | $CHF_2$ |
| 2-Br | 4-Br | H | $CHF_2$ | 2-F | 4-Cl | 6-Cl | $CHF_2$ |
| 2-I | 4-Br | H | $CHF_2$ | 2-Cl | 4-Cl | 6-Cl | $CHF_2$ |
| 2-Me | 4-Br | H | $CHF_2$ | 2-Br | 4-Cl | 6-Cl | $CHF_2$ |
| 2-Et | 4-Br | H | $CHF_2$ | 2-I | 4-Cl | 6-Cl | $CHF_2$ |
| 2-$CF_3$ | 4-Br | H | $CHF_2$ | 2-Me | 4-Cl | 6-Cl | $CHF_2$ |
| 2-$OCF_2H$ | 4-Br | H | $CHF_2$ | 2-Et | 4-Cl | 6-Cl | $CHF_2$ |
| 2-F | 4-I | H | $CHF_2$ | 2-$CF_3$ | 4-Cl | 6-Cl | $CHF_2$ |
| 2-Cl | 4-I | H | $CHF_2$ | 2-$OCF_2H$ | 4-Cl | 6-Cl | $CHF_2$ |
| 2-Br | 4-I | H | $CHF_2$ | 2-F | 4-Cl | 6-Br | $CHF_2$ |
| 2-I | 4-I | H | $CHF_2$ | 2-Cl | 4-Cl | 6-Br | $CHF_2$ |
| 2-Me | 4-I | H | $CHF_2$ | 2-Br | 4-Cl | 6-Br | $CHF_2$ |
| 2-Et | 4-I | H | $CHF_2$ | 2-I | 4-Cl | 6-Br | $CHF_2$ |
| 2-$CF_3$ | 4-I | H | $CHF_2$ | 2-Me | 4-Cl | 6-Br | $CHF_2$ |
| 2-F | 4-$CF_3$ | H | $CHF_2$ | 2-Et | 4-Cl | 6-Br | $CHF_2$ |
| 2-Cl | 4-$CF_3$ | H | $CHF_2$ | 2-$CF_3$ | 4-Cl | 6-Br | $CHF_2$ |
| 2-Br | 4-$CF_3$ | H | $CHF_2$ | 2-$OCF_2H$ | 4-Cl | 6-Br | $CHF_2$ |
| 2-I | 4-$CF_3$ | H | $CHF_2$ | 2-F | 4-Cl | 6-F | $CHF_2$ |
| 2-Me | 4-$CF_3$ | H | $CHF_2$ | 2-Cl | 4-Cl | 6-F | $CHF_2$ |
| 2-Et | 4-$CF_3$ | H | $CHF_2$ | 2-Br | 4-Cl | 6-F | $CHF_2$ |
| 2-$CF_3$ | 4-$CF_3$ | H | $CHF_2$ | 2-I | 4-Cl | 6-F | $CHF_2$ |
| 2-F | 4-CN | H | $CHF_2$ | 2-Me | 4-Cl | 6-F | $CHF_2$ |
| 2-Cl | 4-CN | H | $CHF_2$ | 2-Et | 4-Cl | 6-F | $CHF_2$ |
| 2-Br | 4-CN | H | $CHF_2$ | 2-$CF_3$ | 4-Cl | 6-F | $CHF_2$ |
| 2-I | 4-CN | H | $CHF_2$ | 2-$OCF_2H$ | 4-Cl | 6-F | $CHF_2$ |
| 2-Me | 4-CN | H | $CHF_2$ | 2-F | 4-Br | 6-Cl | $CHF_2$ |
| 2-Et | 4-CN | H | $CHF_2$ | 2-Cl | 4-Br | 6-Cl | $CHF_2$ |
| 2-$CF_3$ | 4-CN | H | $CHF_2$ | 2-Br | 4-Br | 6-Cl | $CHF_2$ |
| 2-F | H | 6-Cl | $CHF_2$ | 2-I | 4-Br | 6-Cl | $CHF_2$ |
| 2-Cl | H | 6-Cl | $CHF_2$ | 2-Me | 4-Br | 6-Cl | $CHF_2$ |
| 2-Br | H | 6-Cl | $CHF_2$ | 2-Et | 4-Br | 6-Cl | $CHF_2$ |
| 2-I | H | 6-Cl | $CHF_2$ | 2-$CF_3$ | 4-Br | 6-Cl | $CHF_2$ |
| 2-Me | H | 6-Cl | $CHF_2$ | 2-$OCF_2H$ | 4-Br | 6-Cl | $CHF_2$ |
| 2-Et | H | 6-Cl | $CHF_2$ | 2-F | 4-Br | 6-Br | $CHF_2$ |
| 2-$CF_3$ | H | 6-Cl | $CHF_2$ | 2-Cl | 4-Br | 6-Br | $CHF_2$ |
| 2-$OCF_2H$ | H | 6-Cl | $CHF_2$ | 2-Br | 4-Br | 6-Br | $CHF_2$ |
| 2-F | H | 6-Br | $CHF_2$ | 2-I | 4-Br | 6-Br | $CHF_2$ |
| 2-Cl | H | 6-Br | $CHF_2$ | 2-Me | 4-Br | 6-Br | $CHF_2$ |
| 2-Br | H | 6-Br | $CHF_2$ | 2-Et | 4-Br | 6-Br | $CHF_2$ |
| 2-I | H | 6-Br | $CHF_2$ | 2-$CF_3$ | 4-Br | 6-Br | $CHF_2$ |
| 2-Me | H | 6-Br | $CHF_2$ | 2-$OCF_2H$ | 4-Br | 6-Br | $CHF_2$ |
| 2-Et | H | 6-Br | $CHF_2$ | 2-F | 4-Br | 6-F | $CHF_2$ |
| 2-$CF_3$ | H | 6-Br | $CHF_2$ | 2-Cl | 4-Br | 6-F | $CHF_2$ |
| 2-$OCF_2H$ | H | 6-Br | $CHF_2$ | 2-Br | 4-Br | 6-F | $CHF_2$ |
| 2-F | H | 6-F | $CHF_2$ | 2-I | 4-Br | 6-F | $CHF_2$ |
| 2-Cl | H | 6-F | $CHF_2$ | 2-Me | 4-Br | 6-F | $CHF_2$ |
| 2-Br | H | 6-P | $CHF_2$ | 2-Et | 4-Br | 6-F | $CHF_2$ |
| 2-I | H | 6-F | $CHF_2$ | 2-$CF_3$ | 4-Br | 6-F | $CHF_2$ |
| 2-Me | H | 6-F | $CHF_2$ | 2-$OCF_2H$ | 4-Br | 6-F | $CHF_2$ |
| 2-Et | H | 6-F | $CHF_2$ | | | | |

TABLE 3

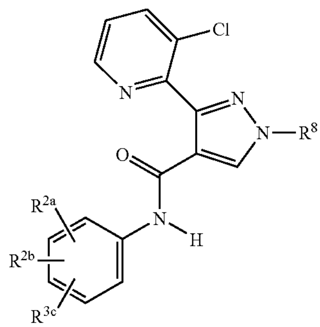

| $R^{2a}$ | $R^{2b}$ | $R^{2c}$ | $R^7$ | $R^{2a}$ | $R^{2b}$ | $R^{2c}$ | $R^7$ |
|---|---|---|---|---|---|---|---|
| H | H | H | Me | H | H | H | $OCH_2CF_3$ |
| 2-F | H | H | Me | 2-F | H | H | $OCH_2CF_3$ |
| 2-Cl | H | H | Me | 2-Cl | H | H | $OCH_2CF_3$ |
| 2-Br | H | H | Me | 2-Br | H | H | $OCH_2CF_3$ |
| 2-I | H | H | Me | 2-I | H | H | $OCH_2CF_3$ |
| 2-Me | H | H | Me | 2-Me | H | H | $OCH_2CF_3$ |
| 2-Et | H | H | Me | 2-Et | H | H | $OCH_2CF_3$ |
| 2-$CF_3$ | H | H | Me | 2-$CF_3$ | H | H | $OCH_2CF_3$ |
| 2-$OCF_2H$ | H | H | Me | 2-$OCF_2H$ | H | H | $OCH_2CF_3$ |
| 2-F | 4-F | H | Me | 2-F | 4-F | H | $OCH_2CF_3$ |
| 2-Cl | 4-F | H | Me | 2-Cl | 4-F | H | $OCH_2CF_3$ |
| 2-Br | 4-F | H | Me | 2-Br | 4-F | H | $OCH_2CF_3$ |
| 2-I | 4-F | H | Me | 2-I | 4-F | H | $OCH_2CF_3$ |
| 2-Me | 4-F | H | Me | 2-Me | 4-F | H | $OCH_2CF_3$ |
| 2-Et | 4-F | H | Me | 2-Et | 4-F | H | $OCH_2CF_3$ |
| 2-$CF_3$ | 4-F | H | Me | 2-$CF_3$ | 4-F | H | $OCH_2CF_3$ |
| 2-$OCF_2H$ | 4-F | H | Me | 2-$OCF_2H$ | 4-F | H | $OCH_2CF_3$ |
| 2-F | 4-Cl | H | Me | 2-F | 4-Cl | H | $OCH_2CF_3$ |
| 2-Cl | 4-Cl | H | Me | 2-Cl | 4-Cl | H | $OCH_2CF_3$ |
| 2-Br | 4-Cl | H | Me | 2-Br | 4-Cl | H | $OCH_2CF_3$ |
| 2-I | 4-Cl | H | Me | 2-I | 4-Cl | H | $OCH_2CF_3$ |
| 2-Me | 4-Cl | H | Me | 2-Me | 4-Cl | H | $OCH_2CF_3$ |
| 2-Et | 4-Cl | H | Me | 2-Et | 4-Cl | H | $OCH_2CF_3$ |
| 2-$CF_3$ | 4-Cl | H | Me | 2-$CF_3$ | 4-Cl | H | $OCH_2CF_3$ |
| 2-$OCF_2H$ | 4-Cl | H | Me | 2-$OCF_2H$ | 4-Cl | H | $OCH_2CF_3$ |
| 2-F | 4-Br | H | Me | 2-F | 4-Br | H | $OCH_2CF_3$ |
| 2-Cl | 4-Br | H | Me | 2-Cl | 4-Br | H | $OCH_2CF_3$ |
| 2-Br | 4-Br | H | Me | 2-Br | 4-Br | H | $OCH_2CF_3$ |
| 2-I | 4-Br | H | Me | 2-I | 4-Br | H | $OCH_2CF_3$ |
| 2-Me | 4-Br | H | Me | 2-Me | 4-Br | H | $OCH_2CF_3$ |
| 2-Et | 4-Br | H | Me | 2-Et | 4-Br | H | $OCH_2CF_3$ |
| 2-$CF_3$ | 4-Br | H | Me | 2-$CF_3$ | 4-Br | H | $OCH_2CF_3$ |
| 2-$OCF_2H$ | 4-Br | H | Me | 2-$OCF_2H$ | 4-Br | H | $OCH_2CF_3$ |
| 2-F | 4-I | H | Me | 2-F | 4-I | H | $OCH_2CF_3$ |
| 2-Cl | 4-I | H | Me | 2-Cl | 4-I | H | $OCH_2CF_3$ |
| 2-Br | 4-I | H | Me | 2-Br | 4-I | H | $OCH_2CF_3$ |
| 2-I | 4-I | H | Me | 2-I | 4-I | H | $OCH_2CF_3$ |
| 2-Me | 4-I | H | Me | 2-Me | 4-I | H | $OCH_2CF_3$ |
| 2-Et | 4-I | H | Me | 2-Et | 4-I | H | $OCH_2CF_3$ |
| 2-$CF_3$ | 4-I | H | Me | 2-$CF_3$ | 4-I | H | $OCH_2CF_3$ |
| 2-F | 4-$CF_3$ | H | Me | 2-F | 4-$CF_3$ | H | $OCH_2CF_3$ |
| 2-Cl | 4-$CF_3$ | H | Me | 2-Cl | 4-$CF_3$ | H | $OCH_2CF_3$ |
| 2-Br | 4-$CF_3$ | H | Me | 2-Br | 4-$CF_3$ | H | $OCH_2CF_3$ |
| 2-I | 4-$CF_3$ | H | Me | 2-I | 4-$CF_3$ | H | $OCH_2CF_3$ |
| 2-Me | 4-$CF_3$ | H | Me | 2-Me | 4-$CF_3$ | H | $OCH_2CF_3$ |
| 2-Et | 4-$CF_3$ | H | Me | 2-Et | 4-$CF_3$ | H | $OCH_2CF_3$ |
| 2-$CF_3$ | 4-$CF_3$ | H | Me | 2-$CF_3$ | 4-$CF_3$ | H | $OCH_2CF_3$ |
| 2-F | 4-CN | H | Me | 2-F | 4-CN | H | $OCH_2CF_3$ |
| 2-Cl | 4-CN | H | Me | 2-Cl | 4-CN | H | $OCH_2CF_3$ |
| 2-Br | 4-CN | H | Me | 2-Br | 4-CN | H | $OCH_2CF_3$ |
| 2-I | 4-CN | H | Me | 2-I | 4-CN | H | $OCH_2CF_3$ |
| 2-Me | 4-CN | H | Me | 2-Me | 4-CN | H | $OCH_2CF_3$ |
| 2-Et | 4-CN | H | Me | 2-Et | 4-CN | H | $OCH_2CF_3$ |
| 2-$CF_3$ | 4-CN | H | Me | 2-$CF_3$ | 4-CN | H | $OCH_2CF_3$ |
| 2-F | H | 6-Cl | Me | 2-F | H | 6-Cl | $OCH_2CF_3$ |
| 2-Cl | H | 6-Cl | Me | 2-Cl | H | 6-Cl | $OCH_2CF_3$ |
| 2-Br | H | 6-Cl | Me | 2-Br | H | 6-Cl | $OCH_2CF_3$ |
| 2-I | H | 6-Cl | Me | 2-I | H | 6-Cl | $OCH_2CF_3$ |

TABLE 3-continued

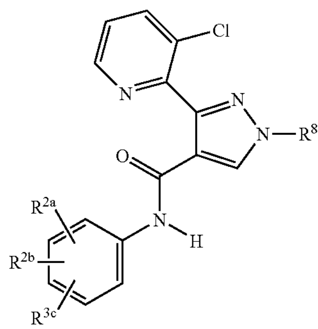

| $R^{2a}$ | $R^{2b}$ | $R^{2c}$ | $R^7$ | $R^{2a}$ | $R^{2b}$ | $R^{2c}$ | $R^7$ |
|---|---|---|---|---|---|---|---|
| 2-Me | H | 6-Cl | Me | 2-Me | H | 6-Cl | $OCH_2CF_3$ |
| 2-Et | H | 6-Cl | Me | 2-Et | H | 6-Cl | $OCH_2CF_3$ |
| 2-$CF_3$ | H | 6-Cl | Me | 2-$CF_3$ | H | 6-Cl | $OCH_2CF_3$ |
| 2-$OCF_2H$ | H | 6-Cl | Me | 2-$OCF_2H$ | H | 6-Cl | $OCH_2CF_3$ |
| 2-F | H | 6-Br | Me | 2-F | H | 6-Br | $OCH_2CF_3$ |
| 2-Cl | H | 6-Br | Me | 2-Cl | H | 6-Br | $OCH_2CF_3$ |
| 2-Br | H | 6-Br | Me | 2-Br | H | 6-Br | $OCH_2CF_3$ |
| 2-I | H | 6-Br | Me | 2-I | H | 6-Br | $OCH_2CF_3$ |
| 2-Me | H | 6-Br | Me | 2-Me | H | 6-Br | $OCH_2CF_3$ |
| 2-Et | H | 6-Br | Me | 2-Et | H | 6-Br | $OCH_2CF_3$ |
| 2-$CF_3$ | H | 6-Br | Me | 2-$CF_3$ | H | 6-Br | $OCH_2CF_3$ |
| 2-$OCF_2H$ | H | 6-Br | Me | 2-$OCF_2H$ | H | 6-Br | $OCH_2CF_3$ |
| 2-F | H | 6-F | Me | 2-F | H | 6-F | $OCH_2CF_3$ |
| 2-Cl | H | 6-F | Me | 2-Cl | H | 6-F | $OCH_2CF_3$ |
| 2-Br | H | 6-F | Me | 2-Br | H | 6-F | $OCH_2CF_3$ |
| 2-I | H | 6-F | Me | 2-I | H | 6-F | $OCH_2CF_3$ |
| 2-Me | H | 6-F | Me | 2-Me | H | 6-F | $OCH_2CF_3$ |
| 2-Et | H | 6-F | Me | 2-Et | H | 6-F | $OCH_2CF_3$ |
| 2-$CF_3$ | H | 6-F | Me | 2-$CF_3$ | H | 6-F | $OCH_2CF_3$ |
| 2-$OCF_2H$ | H | 6-F | Me | 2-$OCF_2H$ | H | 6-F | $OCH_2CF_3$ |
| 2-F | 4-F | 6-Cl | Me | 2-F | 4-F | 6-Cl | $OCH_2CF_3$ |
| 2-Cl | 4-F | 6-Cl | Me | 2-Cl | 4-F | 6-Cl | $OCH_2CF_3$ |
| 2-Br | 4-F | 6-Cl | Me | 2-Br | 4-F | 6-Cl | $OCH_2CF_3$ |
| 2-I | 4-F | 6-Cl | Me | 2-I | 4-F | 6-Cl | $OCH_2CF_3$ |
| 2-Me | 4-F | 6-Cl | Me | 2-Me | 4-F | 6-Cl | $OCH_2CF_3$ |
| 2-Et | 4-F | 6-Cl | Me | 2-Et | 4-F | 6-Cl | $OCH_2CF_3$ |
| 2-$CF_3$ | 4-F | 6-Cl | Me | 2-$CF_3$ | 4-F | 6-Cl | $OCH_2CF_3$ |
| 2-$OCF_2H$ | 4-F | 6-Cl | Me | 2-$OCF_2H$ | 4-F | 6-Cl | $OCH_2CF_3$ |
| 2-F | 4-F | 6-Br | Me | 2-F | 4-F | 6-Br | $OCH_2CF_3$ |
| 2-Cl | 4-F | 6-Br | Me | 2-Cl | 4-F | 6-Br | $OCH_2CF_3$ |
| 2-Br | 4-F | 6-Br | Me | 2-Br | 4-F | 6-Br | $OCH_2CF_3$ |
| 2-I | 4-F | 6-Br | Me | 2-I | 4-F | 6-Br | $OCH_2CF_3$ |
| 2-Me | 4-F | 6-Br | Me | 2-Me | 4-F | 6-Br | $OCH_2CF_3$ |
| 2-Et | 4-F | 6-Br | Me | 2-Et | 4-F | 6-Br | $OCH_2CF_3$ |
| 2-$CF_3$ | 4-F | 6-Br | Me | 2-$CF_3$ | 4-F | 6-Br | $OCH_2CF_3$ |
| 2-$OCF_2H$ | 4-F | 6-Br | Me | 2-$OCF_2H$ | 4-F | 6-Br | $OCH_2CF_3$ |
| 2-F | 4-F | 6-F | Me | 2-F | 4-F | 6-F | $OCH_2CF_3$ |
| 2-Cl | 4-F | 6-F | Me | 2-Cl | 4-F | 6-F | $OCH_2CF_3$ |
| 2-Br | 4-F | 6-F | Me | 2-Br | 4-F | 6-F | $OCH_2CF_3$ |
| 2-I | 4-F | 6-F | Me | 2-I | 4-F | 6-F | $OCH_2CF_3$ |
| 2-Me | 4-F | 6-F | Me | 2-Me | 4-F | 6-F | $OCH_2CF_3$ |
| 2-Et | 4-F | 6-F | Me | 2-Et | 4-F | 6-F | $OCH_2CF_3$ |
| 2-$CF_3$ | 4-F | 6-F | Me | 2-$CF_3$ | 4-F | 6-F | $OCH_2CF_3$ |
| 2-$OCF_2H$ | 4-F | 6-F | Me | 2-$OCF_2H$ | 4-F | 6-F | $OCH_2CF_3$ |
| 2-F | 4-Cl | 6-Cl | Me | 2-F | 4-Cl | 6-Cl | $OCH_2CF_3$ |
| 2-Cl | 4-Cl | 6-Cl | Me | 2-Cl | 4-Cl | 6-Cl | $OCH_2CF_3$ |
| 2-Br | 4-Cl | 6-Cl | Me | 2-Br | 4-Cl | 6-Cl | $OCH_2CF_3$ |
| 2-I | 4-Cl | 6-Cl | Me | 2-I | 4-Cl | 6-Cl | $OCH_2CF_3$ |
| 2-Me | 4-Cl | 6-Cl | Me | 2-Me | 4-Cl | 6-Cl | $OCH_2CF_3$ |
| 2-Et | 4-Cl | 6-Cl | Me | 2-Et | 4-Cl | 6-Cl | $OCH_2CF_3$ |
| 2-$CF_3$ | 4-Cl | 6-Cl | Me | 2-$CF_3$ | 4-Cl | 6-Cl | $OCH_2CF_3$ |
| 2-$OCF_2H$ | 4-Cl | 6-Cl | Me | 2-$OCF_2H$ | 4-Cl | 6-Cl | $OCH_2CF_3$ |
| 2-F | 4-Cl | 6-Br | Me | 2-F | 4-Cl | 6-Br | $OCH_2CF_3$ |
| 2-Cl | 4-Cl | 6-Br | Me | 2-Cl | 4-Cl | 6-Br | $OCH_2CF_3$ |
| 2-Br | 4-Cl | 6-Br | Me | 2-Br | 4-Cl | 6-Br | $OCH_2CF_3$ |
| 2-I | 4-Cl | 6-Br | Me | 2-I | 4-Cl | 6-Br | $OCH_2CF_3$ |
| 2-Me | 4-Cl | 6-Br | Me | 2-Me | 4-Cl | 6-Br | $OCH_2CF_3$ |

TABLE 3-continued

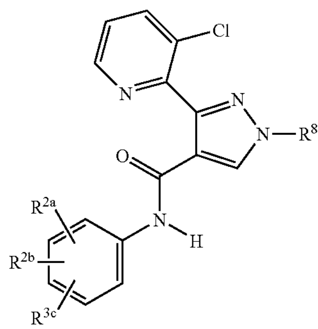

| $R^{2a}$ | $R^{2b}$ | $R^{2c}$ | $R^7$ | $R^{2a}$ | $R^{2b}$ | $R^{2c}$ | $R^7$ |
|---|---|---|---|---|---|---|---|
| 2-Et | 4-Cl | 6-Br | Me | 2-Et | 4-Cl | 6-Br | $OCH_2CF_3$ |
| 2-$CF_3$ | 4-Cl | 6-Br | Me | 2-$CF_3$ | 4-Cl | 6-Br | $OCH_2CF_3$ |
| 2-$OCF_2H$ | 4-Cl | 6-Br | Me | 2-$OCF_2H$ | 4-Cl | 6-Br | $OCH_2CF_3$ |
| 2-F | 4-Cl | 6-F | Me | 2-F | 4-Cl | 6-F | $OCH_2CF_3$ |
| 2-Cl | 4-Cl | 6-F | Me | 2-Cl | 4-Cl | 6-F | $OCH_2CF_3$ |
| 2-Br | 4-Cl | 6-F | Me | 2-Br | 4-Cl | 6-F | $OCH_2CF_3$ |
| 2-I | 4-Cl | 6-F | Me | 2-I | 4-Cl | 6-F | $OCH_2CF_3$ |
| 2-Me | 4-Cl | 6-F | Me | 2-Me | 4-Cl | 6-F | $OCH_2CF_3$ |
| 2-Et | 4-Cl | 6-F | Me | 2-Et | 4-Cl | 6-F | $OCH_2CF_3$ |
| 2-$CF_3$ | 4-Cl | 6-F | Me | 2-$CF_3$ | 4-Cl | 6-F | $OCH_2CF_3$ |
| 2-$OCF_2H$ | 4-Cl | 6-F | Me | 2-$OCF_2H$ | 4-Cl | 6-F | $OCH_2CF_3$ |
| 2-F | 4-Br | 6-Cl | Me | 2-F | 4-Br | 6-Cl | $OCH_2CF_3$ |
| 2-Cl | 4-Br | 6-Cl | Me | 2-Cl | 4-Br | 6-Cl | $OCH_2CF_3$ |
| 2-Br | 4-Br | 6-Cl | Me | 2-Br | 4-Br | 6-Cl | $OCH_2CF_3$ |
| 2-I | 4-Br | 6-Cl | Me | 2-I | 4-Br | 6-Cl | $OCH_2CF_3$ |
| 2-Me | 4-Br | 6-Cl | Me | 2-Me | 4-Br | 6-Cl | $OCH_2CF_3$ |
| 2-Et | 4-Br | 6-Cl | Me | 2-Et | 4-Br | 6-Cl | $OCH_2CF_3$ |
| 2-$CF_3$ | 4-Br | 6-Cl | Me | 2-$CF_3$ | 4-Br | 6-Cl | $OCH_2CF_3$ |
| 2-$OCF_2H$ | 4-Br | 6-Cl | Me | 2-$OCF_2H$ | 4-Br | 6-Cl | $OCH_2CF_3$ |
| 2-F | 4-Br | 6-Br | Me | 2-F | 4-Br | 6-Br | $OCH_2CF_3$ |
| 2-Cl | 4-Br | 6-Br | Me | 2-Cl | 4-Br | 6-Br | $OCH_2CF_3$ |
| 2-Br | 4-Br | 6-Br | Me | 2-Br | 4-Br | 6-Br | $OCH_2CF_3$ |
| 2-I | 4-Br | 6-Br | Me | 2-I | 4-Br | 6-Br | $OCH_2CF_3$ |
| 2-Me | 4-Br | 6-Br | Me | 2-Me | 4-Br | 6-Br | $OCH_2CF_3$ |
| 2-Et | 4-Br | 6-Br | Me | 2-Et | 4-Br | 6-Br | $OCH_2CF_3$ |
| 2-$CF_3$ | 4-Br | 6-Br | Me | 2-$CF_3$ | 4-Br | 6-Br | $OCH_2CF_3$ |
| 2-$OCF_2H$ | 4-Br | 6-Br | Me | 2-$OCF_2H$ | 4-Br | 6-Br | $OCH_2CF_3$ |
| 2-F | 4-Br | 6-F | Me | 2-F | 4-Br | 6-F | $OCH_2CF_3$ |
| 2-Cl | 4-Br | 6-F | Me | 2-Cl | 4-Br | 6-F | $OCH_2CF_3$ |
| 2-Br | 4-Br | 6-F | Me | 2-Br | 4-Br | 6-F | $OCH_2CF_3$ |
| 2-I | 4-Br | 6-F | Me | 2-I | 4-Br | 6-F | $OCH_2CF_3$ |
| 2-Me | 4-Br | 6-F | Me | 2-Me | 4-Br | 6-F | $OCH_2CF_3$ |
| 2-Et | 4-Br | 6-F | Me | 2-Et | 4-Br | 6-F | $OCH_2CF_3$ |
| 2-$CF_3$ | 4-Br | 6-F | Me | 2-$CF_3$ | 4-Br | 6-F | $OCH_2CF_3$ |
| 2-$OCF_2H$ | 4-Br | 6-F | Me | 2-$OCF_2H$ | 4-Br | 6-F | $OCH_2CF_3$ |
| 2-F | H | H | $CHF_2$ | 2-$CF_3$ | H | 6-F | $CHF_2$ |
| 2-Cl | H | H | $CHF_2$ | 2-$OCF_2H$ | H | 6-F | $CHF_2$ |
| 2-Br | H | H | $CHF_2$ | 2-F | 4-F | 6-Cl | $CHF_2$ |
| 2-I | H | H | $CHF_2$ | 2-Cl | 4-F | 6-Cl | $CHF_2$ |
| 2-Me | H | H | $CHF_2$ | 2-Br | 4-F | 6-Cl | $CHF_2$ |
| 2-Et | H | H | $CHF_2$ | 2-I | 4-F | 6-Cl | $CHF_2$ |
| 2-$CF_3$ | H | H | $CHF_2$ | 2-Me | 4-F | 6-Cl | $CHF_2$ |
| 2-$OCF_2H$ | H | $CHF_2$ | 2-Et | 4-F | 6-Cl | $CHF_2$ | |
| 2-F | 4-F | H | $CHF_2$ | 2-$CF_3$ | 4-F | 6-Cl | $CHF_2$ |
| 2-Cl | 4-F | H | $CHF_2$ | 2-$OCF_2H$ | 4-F | 6-Cl | $CHF_2$ |
| 2-Br | 4-F | H | $CHF_2$ | 2-F | 4-F | 6-Br | $CHF_2$ |
| 2-I | 4-F | H | $CHF_2$ | 2-Cl | 4-F | 6-Br | $CHF_2$ |
| 2-Me | 4-F | H | $CHF_2$ | 2-Br | 4-F | 6-Br | $CHF_2$ |
| 2-Et | 4-F | H | $CHF_2$ | 2-I | 4-F | 6-Br | $CHF_2$ |
| 2-$CF_3$ | 4-F | H | $CHF_2$ | 2-Me | 4-F | 6-Br | $CHF_2$ |
| 2-$OCF_2H$ | 4-F | H | $CHF_2$ | 2-Et | 4-F | 6-Br | $CHF_2$ |
| 2-F | 4-Cl | H | $CHF_2$ | 2-$CF_3$ | 4-F | 6-Br | $CHF_2$ |
| 2-Cl | 4-Cl | H | $CHF_2$ | 2-$OCF_2H$ | 4-F | 6-Br | $CHF_2$ |
| 2-Br | 4-Cl | H | $CHF_2$ | 2-F | 4-F | 6-F | $CHF_2$ |
| 2-I | 4-Cl | H | $CHF_2$ | 2-Cl | 4-F | 6-F | $CHF_2$ |
| 2-Me | 4-Cl | H | $CHF_2$ | 2-Br | 4-F | 6-F | $CHF_2$ |
| 2-Et | 4-Cl | H | $CHF_2$ | 2-I | 4-F | 6-F | $CHF_2$ |

TABLE 3-continued

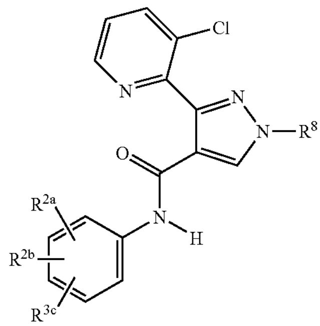

| $R^{2a}$ | $R^{2b}$ | $R^{2c}$ | $R^7$ | $R^{2a}$ | $R^{2b}$ | $R^{2c}$ | $R^7$ |
|---|---|---|---|---|---|---|---|
| 2-$CF_3$ | 4-Cl | H | $CHF_2$ | 2-Me | 4-F | 6-F | $CHF_2$ |
| 2-$OCF_2H$ | 4-Cl | H | $CHF_2$ | 2-Et | 4-F | 6-F | $CHF_2$ |
| 2-F | 4-Br | H | $CHF_2$ | 2-$CF_3$ | 4-F | 6-F | $CHF_2$ |
| 2-Cl | 4-Br | H | $CHF_2$ | 2-$OCF_2H$ | 4-F | 6-F | $CHF_2$ |
| 2-Br | 4-Br | H | $CHF_2$ | 2-F | 4-Cl | 6-Cl | $CHF_2$ |
| 2-I | 4-Br | H | $CHF_2$ | 2-Cl | 4-Cl | 6-Cl | $CHF_2$ |
| 2-Me | 4-Br | H | $CHF_2$ | 2-Br | 4-Cl | 6-Cl | $CHF_2$ |
| 2-Et | 4-Br | H | $CHF_2$ | 2-I | 4-Cl | 6-Cl | $CHF_2$ |
| 2-$CF_3$ | 4-Br | H | $CHF_2$ | 2-Me | 4-Cl | 6-Cl | $CHF_2$ |
| 2-$OCF_2H$ | 4-Br | H | $CHF_2$ | 2-Et | 4-Cl | 6-Cl | $CHF_2$ |
| 2-F | 4-I | H | $CHF_2$ | 2-$CF_3$ | 4-Cl | 6-Cl | $CHF_2$ |
| 2-Cl | 4-I | H | $CHF_2$ | 2-$OCF_2H$ | 4-Cl | 6-Cl | $CHF_2$ |
| 2-Br | 4-I | H | $CHF_2$ | 2-F | 4-Cl | 6-Br | $CHF_2$ |
| 2-I | 4-I | H | $CHF_2$ | 2-Cl | 4-Cl | 6-Br | $CHF_2$ |
| 2-Me | 4-I | H | $CHF_2$ | 2-Br | 4-Cl | 6-Br | $CHF_2$ |
| 2-Et | 4-I | H | $CHF_2$ | 2-I | 4-Cl | 6-Br | $CHF_2$ |
| 2-$CF_3$ | 4-I | H | $CHF_2$ | 2-Me | 4-Cl | 6-Br | $CHF_2$ |
| 2-F | 4-$CF_3$ | H | $CHF_2$ | 2-Et | 4-Cl | 6-Br | $CHF_2$ |
| 2-Cl | 4-$CF_3$ | H | $CHF_2$ | 2-$CF_3$ | 4-Cl | 6-Br | $CHF_2$ |
| 2-Br | 4-$CF_3$ | H | $CHF_2$ | 2-$OCF_2H$ | 4-Cl | 6-Br | $CHF_2$ |
| 2-I | 4-$CF_3$ | H | $CHF_2$ | 2-F | 4-Cl | 6-F | $CHF_2$ |
| 2-Me | 4-$CF_3$ | H | $CHF_2$ | 2-Cl | 4-Cl | 6-F | $CHF_2$ |
| 2-Et | 4-$CF_3$ | H | $CHF_2$ | 2-Br | 4-Cl | 6-F | $CHF_2$ |
| 2-$CF_3$ | 4-$CF_3$ | H | $CHF_2$ | 2-I | 4-Cl | 6-F | $CHF_2$ |
| 2-F | 4-CN | H | $CHF_2$ | 2-Me | 4-Cl | 6-F | $CHF_2$ |
| 2-Cl | 4-CN | H | $CHF_2$ | 2-Et | 4-Cl | 6-F | $CHF_2$ |
| 2-Br | 4-CN | H | $CHF_2$ | 2-$CF_3$ | 4-Cl | 6-F | $CHF_2$ |
| 2-I | 4-CN | H | $CHF_2$ | 2-$OCF_2H$ | 4-Cl | 6-F | $CHF_2$ |
| 2-Me | 4-CN | H | $CHF_2$ | 2-F | 4-Br | 6-Cl | $CHF_2$ |
| 2-Et | 4-CN | H | $CHF_2$ | 2-Cl | 4-Br | 6-Cl | $CHF_2$ |
| 2-$CF_3$ | 4-CN | H | $CHF_2$ | 2-Br | 4-Br | 6-Cl | $CHF_2$ |
| 2-F | H | 6-Cl | $CHF_2$ | 2-I | 4-Br | 6-Cl | $CHF_2$ |
| 2-Cl | H | 6-Cl | $CHF_2$ | 2-Me | 4-Br | 6-Cl | $CHF_2$ |
| 2-Br | H | 6-Cl | $CHF_2$ | 2-Et | 4-Br | 6-Cl | $CHF_2$ |
| 2-I | H | 6-Cl | $CHF_2$ | 2-$CF_3$ | 4-Br | 6-Cl | $CHF_2$ |
| 2-Me | H | 6-Cl | $CHF_2$ | 2-$OCF_2H$ | 4-Br | 6-Cl | $CHF_2$ |
| 2-Et | H | 6-Cl | $CHF_2$ | 2-F | 4-Br | 6-Br | $CHF_2$ |
| 2-$CF_3$ | H | 6-Cl | $CHF_2$ | 2-Cl | 4-Br | 6-Br | $CHF_2$ |
| 2-$OCF_2H$ | H | 6-Cl | $CHF_2$ | 2-Br | 4-Br | 6-Br | $CHF_2$ |
| 2-F | H | 6-Br | $CHF_2$ | 2-I | 4-Br | 6-Br | $CHF_2$ |
| 2-Cl | H | 6-Br | $CHF_2$ | 2-Me | 4-Br | 6-Br | $CHF_2$ |
| 2-Br | H | 6-Br | $CHF_2$ | 2-Et | 4-Br | 6-Br | $CHF_2$ |
| 2-I | H | 6-Br | $CHF_2$ | 2-$CF_3$ | 4-Br | 6-Br | $CHF_2$ |
| 2-Me | H | 6-Br | $CHF_2$ | 2-$OCF_2H$ | 4-Br | 6-Br | $CHF_2$ |
| 2-Et | H | 6-Br | $CHF_2$ | 2-F | 4-Br | 6-F | $CHF_2$ |
| 2-$CF_3$ | H | 6-Br | $CHF_2$ | 2-Cl | 4-Br | 6-F | $CHF_2$ |
| 2-$OCF_2H$ | H | 6-Br | $CHF_2$ | 2-Br | 4-Br | 6-F | $CHF_2$ |
| 2-F | H | 6-F | $CHF_2$ | 2-I | 4-Br | 6-F | $CHF_2$ |
| 2-Cl | H | 6-F | $CHF_2$ | 2-Me | 4-Br | 6-F | $CHF_2$ |
| 2-Br | H | 6-F | $CHF_2$ | 2-Et | 4-Br | 6-F | $CHF_2$ |
| 2-I | H | 6-F | $CHF_2$ | 2-$CF_3$ | 4-Br | 6-F | $CHF_2$ |
| 2-Me | H | 6-F | $CHF_2$ | 2-$OCF_2H$ | 4-Br | 6-F | $CHF_2$ |
| 2-Et | H | 6-F | $CHF_2$ | | | | |

TABLE 4

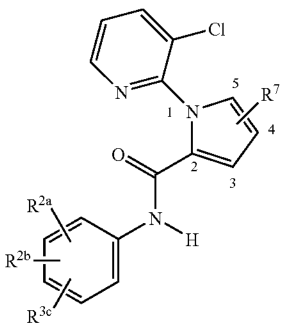

| R⁷ is attached to the 5 position | | | | R⁷ is attached to the 4 position | | | |
|---|---|---|---|---|---|---|---|
| $R^{2a}$ | $R^{2b}$ | $R^{2c}$ | $R^7$ | $R^{2a}$ | $R^{2b}$ | $R^{2c}$ | $R^7$ |
| H | H | H | Cl | H | H | H | Cl |
| 2-F | H | H | Cl | 2-F | H | H | Cl |
| 2-Cl | H | H | Cl | 2-Cl | H | H | Cl |
| 2-Br | H | H | Cl | 2-Br | H | H | Cl |
| 2-I | H | H | Cl | 2-I | H | H | Cl |
| 2-Me | H | H | Cl | 2-Me | H | H | Cl |
| 2-Et | H | H | Cl | 2-Et | H | H | Cl |
| 2-$CF_3$ | H | H | Cl | 2-$CF_3$ | H | H | Cl |
| 2-$OCF_2H$ | H | H | Cl | 2-$OCF_2H$ | H | H | Cl |
| 2-F | 4-F | H | Cl | 2-F | 4-F | H | Cl |
| 2-Cl | 4-F | H | Cl | 2-Cl | 4-F | H | Cl |
| 2-Br | 4-F | H | Cl | 2-Br | 4-F | H | Cl |
| 2-I | 4-F | H | Cl | 2-I | 4-F | H | Cl |
| 2-Me | 4-F | H | Cl | 2-Me | 4-F | H | Cl |
| 2-Et | 4-F | H | Cl | 2-Et | 4-F | H | Cl |
| 2-$CF_3$ | 4-F | H | Cl | 2-$CF_3$ | 4-F | H | Cl |
| 2-$OCF_2H$ | 4-F | H | Cl | 2-$OCF_2H$ | 4-F | H | Cl |
| 2-F | 4-Cl | H | Cl | 2-F | 4-Cl | H | Cl |
| 2-Cl | 4-Cl | H | Cl | 2-Cl | 4-Cl | H | Cl |
| 2-Br | 4-Cl | H | Cl | 2-Br | 4-Cl | H | Cl |
| 2-I | 4-Cl | H | Cl | 2-I | 4-Cl | H | Cl |
| 2-Me | 4-Cl | H | Cl | 2-Me | 4-Cl | H | Cl |
| 2-Et | 4-Cl | H | Cl | 2-Et | 4-Cl | H | Cl |
| 2-$CF_3$ | 4-Cl | H | Cl | 2-$CF_3$ | 4-Cl | H | Cl |
| 2-$OCF_2H$ | 4-Cl | H | Cl | 2-$OCF_2H$ | 4-Cl | H | Cl |
| 2-F | 4-Br | H | Cl | 2-F | 4-Br | H | Cl |
| 2-Cl | 4-Br | H | Cl | 2-Cl | 4-Br | H | Cl |
| 2-Br | 4-Br | H | Cl | 2-Br | 4-Br | H | Cl |
| 2-I | 4-Br | H | Cl | 2-I | 4-Br | H | Cl |
| 2-Me | 4-Br | H | Cl | 2-Me | 4-Br | H | Cl |
| 2-Et | 4-Br | H | Cl | 2-Et | 4-Br | H | Cl |
| 2-$CF_3$ | 4-Br | H | Cl | 2-$CF_3$ | 4-Br | H | Cl |
| 2-$OCF_2H$ | 4-Br | H | Cl | 2-$OCF_2H$ | 4-Br | H | Cl |
| 2-F | 4-I | H | Cl | 2-F | 4-I | H | Cl |
| 2-Cl | 4-I | H | Cl | 2-Cl | 4-I | H | Cl |
| 2-Br | 4-I | H | Cl | 2-Br | 4-I | H | Cl |
| 2-I | 4-I | H | Cl | 2-I | 4-I | H | Cl |
| 2-Me | 4-I | H | Cl | 2-Me | 4-I | H | Cl |
| 2-Et | 4-I | H | Cl | 2-Et | 4-I | H | Cl |
| 2-$CF_3$ | 4-I | H | Cl | 2-$CF_3$ | 4-I | H | Cl |
| 2-F 4-$CF_3$ | H | Cl | 2-F | 4-$CF_3$ | H | Cl | |
| 2-Cl | 4-$CF_3$ | H | Cl | 2-Cl | 4-$CF_3$ | H | Cl |
| 2-Br | 4-$CF_3$ | H | Cl | 2-Br | 4-$CF_3$ | H | Cl |
| 2-I | 4-$CF_3$ | H | Cl | 2-I | 4-$CF_3$ | H | Cl |
| 2-Me | 4-$CF_3$ | H | Cl | 2-Me | 4-$CF_3$ | H | Cl |
| 2-Et | 4-$CF_3$ | H | Cl | 2-Et | 4-$CF_3$ | H | Cl |
| 2-$CF_3$ | 4-$CF_3$ | H | Cl | 2-$CF_3$ | 4-$CF_3$ | H | Cl |
| 2-F | 4-CN | H | Cl | 2-F | 4-CN | H | Cl |
| 2-Cl | 4-CN | H | Cl | 2-Cl | 4-CN | H | Cl |
| 2-Br | 4-CN | H | Cl | 2-Br | 4-CN | H | Cl |
| 2-I | 4-CN | H | Cl | 2-I | 4-CN | H | Cl |
| 2-Me | 4-CN | H | Cl | 2-Me | 4-CN | H | Cl |
| 2-Et | 4-CN | H | Cl | 2-Et | 4-CN | H | Cl |
| 2-$CF_3$ | 4-CN | H | Cl | 2-$CF_3$ | 4-CN | H | Cl |
| 2-F | H | 6-Cl | Cl | 2-F | H | 6-Cl | Cl |
| 2-Cl | H | 6-Cl | Cl | 2-Cl | H | 6-Cl | Cl |
| 2-Br | H | 6-Cl | Cl | 2-Br | H | 6-Cl | Cl |
| 2-I | H | 6-Cl | Cl | 2-I | H | 6-Cl | Cl |
| 2-Me | H | 6-Cl | Cl | 2-Me | H | 6-Cl | Cl |

TABLE 4-continued

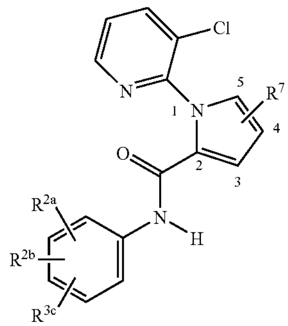

| $R^7$ is attached to the 5 position | | | | $R^7$ is attached to the 4 position | | | |
|---|---|---|---|---|---|---|---|
| $R^{2a}$ | $R^{2b}$ | $R^{2c}$ | $R^7$ | $R^{2a}$ | $R^{2b}$ | $R^{2c}$ | $R^7$ |
| 2-Et | H | 6-Cl | Cl | 2-Et | H | 6-Cl | Cl |
| 2-$CF_3$ | H | 6-Cl | Cl | 2-$CF_3$ | H | 6-Cl | Cl |
| 2-$OCF_2H$ | H | 6-Cl | Cl | 2-$OCF_2H$ H | 6-Cl | Cl | |
| 2-F | H | 6-Br | Cl | 2-F | H | 6-Br | Cl |
| 2-Cl | H | 6-Br | Cl | 2-Cl | H | 6-Br | Cl |
| 2-Br | H | 6-Br | Cl | 2-Br | H | 6-Br | Cl |
| 2-I | H | 6-Br | Cl | 2-I | H | 6-Br | Cl |
| 2-Me | H | 6-Br | Cl | 2-Me | H | 6-Br | Cl |
| 2-Et | H | 6-Br | Cl | 2-Et | H | 6-Br | Cl |
| 2-$CF_3$ | H | 6-Br | Cl | 2-$CF_3$ | H | 6-Br | Cl |
| 2-$OCF_2H$ | H | 6-Br | Cl | 2-$OCF_2H$ H | 6-Br | Cl | |
| 2-F | H | 6-F | Cl | 2-F | H | 6-F | Cl |
| 2-Cl | H | 6-F | Cl | 2-Cl | H | 6-F | Cl |
| 2-Br | H | 6-F | Cl | 2-Br | H | 6-F | Cl |
| 2-I | H | 6-F | Cl | 2-I | H | 6-F | Cl |
| 2-Me | H | 6-F | Cl | 2-Me | H | 6-F | Cl |
| 2-Et | H | 6-F | Cl | 2-Et | H | 6-F | Cl |
| 2-$CF_3$ | H | 6-F | Cl | 2-$CF_3$ | H | 6-F | Cl |
| 2-$OCF_2H$ | H | 6-F | Cl | 2-$OCF_2H$ | H | 6-F | Cl |
| 2-F | 4-F | 6-Cl | Cl | 2-F | 4-F | 6-Cl | Cl |
| 2-Cl | 4-F | 6-Cl | Cl | 2-Cl | 4-F | 6-Cl | Cl |
| 2-Br | 4-F | 6-Cl | Cl | 2-Br | 4-F | 6-Cl | Cl |
| 2-I | 4-F | 6-Cl | Cl | 2-I | 4-F | 6-Cl | Cl |
| 2-Me | 4-F | 6-Cl | Cl | 2-Me | 4-F | 6-Cl | Cl |
| 2-Et | 4-F | 6-Cl | Cl | 2-Et | 4-F | 6-Cl | Cl |
| 2-$CF_3$ | 4-F | 6-Cl | Cl | 2-$CF_3$ | 4-F | 6-Cl | Cl |
| 2-$OCF_2H$ | 4-F | 6-Cl | Cl | 2-$OCF_2H$ | 4-F | 6-Cl | Cl |
| 2-F | 4-F | 6-Br | Cl | 2-F | 4-F | 6-Br | Cl |
| 2-Cl | 4-F | 6-Br | Cl | 2-Cl | 4-F | 6-Br | Cl |
| 2-Br | 4-F | 6-Br | Cl | 2-Br | 4-F | 6-Br | Cl |
| 2-I | 4-F | 6-Br | Cl | 2-I | 4-F | 6-Br | Cl |
| 2-Me | 4-F | 6-Br | Cl | 2-Me | 4-F | 6-Br | Cl |
| 2-Et | 4-F | 6-Br | Cl | 2-Et | 4-F | 6-Br | Cl |
| 2-$CF_3$ | 4-F | 6-Br | Cl | 2-$CF_3$ | 4-F | 6-Br | Cl |
| 2-$OCF_2H$ | 4-F | 6-Br | Cl | 2-$OCF_2H$ | 4-F | 6-Br | Cl |
| 2-F | 4-F | 6-F | Cl | 2-F | 4-F | 6-F | Cl |
| 2-Cl | 4-F | 6-F | Cl | 2-Cl | 4-F | 6-F | Cl |
| 2-Br | 4-F | 6-F | Cl | 2-Br | 4-F | 6-F | Cl |
| 2-I | 4-F | 6-F | Cl | 2-I | 4-F | 6-F | Cl |
| 2-Me | 4-F | 6-F | Cl | 2-Me | 4-F | 6-F | Cl |
| 2-Et | 4-F | 6-F | Cl | 2-Et | 4-F | 6-F | Cl |
| 2-$CF_3$ | 4-F | 6-F | Cl | 2-$CF_3$ | 4-F | 6-F | Cl |
| 2-$OCF_2H$ | 4-F | 6-F | Cl | 2-$OCF_2H$ | 4-F | 6-F | Cl |
| 2-F | 4-Cl | 6-Cl | Cl | 2-F | 4-Cl | 6-Cl | Cl |
| 2-Cl | 4-Cl | 6-Cl | Cl | 2-Cl | 4-Cl | 6-Cl | Cl |
| 2-Br | 4-Cl | 6-Cl | Cl | 2-Br | 4-Cl | 6-Cl | Cl |
| 2-I | 4-Cl | 6-Cl | Cl | 2-I | 4-Cl | 6-Cl | Cl |
| 2-Me | 4-Cl | 6-Cl | Cl | 2-Me | 4-Cl | 6-Cl | Cl |
| 2-Et | 4-Cl | 6-Cl | Cl | 2-Et | 4-Cl | 6-Cl | Cl |
| 2-$CF_3$ | 4-Cl | 6-Cl | Cl | 2-$CF_3$ | 4-Cl | 6-Cl | Cl |
| 2-$OCF_2H$ | 4-Cl | 6-Cl | Cl | 2-$OCF_2H$ | 4-Cl | 6-Cl | Cl |
| 2-F | 4-Cl | 6-Br | Cl | 2-F | 4-Cl | 6-Br | Cl |
| 2-Cl | 4-Cl | 6-Br | Cl | 2-Cl | 4-Cl | 6-Br | Cl |
| 2-Br | 4-Cl | 6-Br | Cl | 2-Br | 4-Cl | 6-Br | Cl |
| 2-I | 4-Cl | 6-Br | Cl | 2-I | 4-Cl | 6-Br | Cl |
| 2-Me | 4-Cl | 6-Br | Cl | 2-Me | 4-Cl | 6-Br | Cl |
| 2-Et | 4-Cl | 6-Br | Cl | 2-Et | 4-Cl | 6-Br | Cl |
| 2-$CF_3$ | 4-Cl | 6-Br | Cl | 2-$CF_3$ | 4-Cl | 6-Br | Cl |
| 2-$OCF_2H$ | 4-Cl | 6-Br | Cl | 2-$OCF_2H$ | 4-Cl | 6-Br | Cl |

TABLE 4-continued

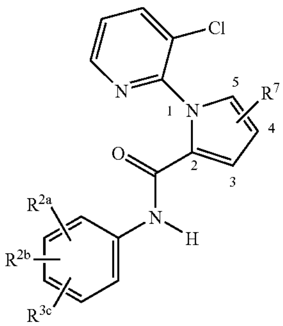

| R⁷ is attached to the 5 position | | | | R⁷ is attached to the 4 position | | | |
|---|---|---|---|---|---|---|---|
| $R^{2a}$ | $R^{2b}$ | $R^{2c}$ | $R^7$ | $R^{2a}$ | $R^{2b}$ | $R^{2c}$ | $R^7$ |
| 2-F | 4-Cl | 6-F | Cl | 2-F | 4-Cl | 6-F | Cl |
| 2-Cl | 4-Cl | 6-F | Cl | 2-Cl | 4-Cl | 6-F | Cl |
| 2-Br | 4-Cl | 6-F | Cl | 2-Br | 4-Cl | 6-F | Cl |
| 2-I | 4-Cl | 6-F | Cl | 2-I | 4-Cl | 6-F | Cl |
| 2-Me | 4-Cl | 6-F | Cl | 2-Me | 4-Cl | 6-F | Cl |
| 2-Et | 4-Cl | 6-F | Cl | 2-Et | 4-Cl | 6-F | Cl |
| 2-$CF_3$ | 4-Cl | 6-F | Cl | 2-$CF_3$ | 4-Cl | 6-F | Cl |
| 2-$OCF_2H$ | 4-Cl | 6-F | Cl | 2-$OCF_2H$ | 4-Cl | 6-F | Cl |
| 2-F | 4-Br | 6-Cl | Cl | 2-F | 4-Br | 6-Cl | Cl |
| 2-Cl | 4-Br | 6-Cl | Cl | 2-Cl | 4-Br | 6-Cl | Cl |
| 2-Br | 4-Br | 6-Cl | Cl | 2-Br | 4-Br | 6-Cl | Cl |
| 2-I | 4-Br | 6-Cl | Cl | 2-I | 4-Br | 6-Cl | Cl |
| 2-Me | 4-Br | 6-Cl | Cl | 2-Me | 4-Br | 6-Cl | Cl |
| 2-Et | 4-Br | 6-Cl | Cl | 2-Et | 4-Br | 6-Cl | Cl |
| 2-$CF_3$ | 4-Br | 6-Cl | Cl | 2-$CF_3$ | 4-Br | 6-Cl | Cl |
| 2-$OCF_2H$ | 4-Br | 6-Cl | Cl | 2-$OCF_2H$ | 4-Br | 6-Cl | Cl |
| 2-F | 4-Br | 6-Br | Cl | 2-F | 4-Br | 6-Br | Cl |
| 2-Cl | 4-Br | 6-Br | Cl | 2-Cl | 4-Br | 6-Br | Cl |
| 2-Br | 4-Br | 6-Br | Cl | 2-Br | 4-Br | 6-Br | Cl |
| 2-I | 4-Br | 6-Br | Cl | 2-I | 4-Br | 6-Br | Cl |
| 2-Me | 4-Br | 6-Br | Cl | 2-Me | 4-Br | 6-Br | Cl |
| 2-Et | 4-Br | 6-Br | Cl | 2-Et | 4-Br | 6-Br | Cl |
| 2-$CF_3$ | 4-Br | 6-Br | Cl | 2-$CF_3$ | 4-Br | 6-Br | Cl |
| 2-$OCF_2H$ | 4-Br | 6-Br | Cl | 2-$OCF_2H$ | 4-Br | 6-Br | Cl |
| 2-F | 4-Br | 6-F | Cl | 2-F | 4-Br | 6-F | Cl |
| 2-Cl | 4-Br | 6-F | Cl | 2-Cl | 4-Br | 6-F | Cl |
| 2-Br | 4-Br | 6-F | Cl | 2-Br | 4-Br | 6-F | Cl |
| 2-I | 4-Br | 6-F | Cl | 2-I | 4-Br | 6-F | Cl |
| 2-Me | 4-Br | 6-F | Cl | 2-Me | 4-Br | 6-F | Cl |
| 2-Et | 4-Br | 6-F | Cl | 2-Et | 4-Br | 6-F | Cl |
| 2-$CF_3$ | 4-Br | 6-F | Cl | 2-$CF_3$ | 4-Br | 6-F | Cl |
| 2-$OCF_2H$ | 4-Br | 6-F | Cl | 2-$OCF_2H$ | 4-Br | 6-F | Cl |
| 2-F | H | H | Br | 2-F | H | H | Br |
| 2-Cl | H | H | Br | 2-Cl | H | H | Br |
| 2-Br | H | H | Br | 2-Br | H | H | Br |
| 2-I | H | H | Br | 2-I | H | H | Br |
| 2-Me | H | H | Br | 2-Me | H | H | Br |
| 2-Et | H | H | Br | 2-Et | H | H | Br |
| 2-$CF_3$ | H | H | Br | 2-$CF_3$ | H | H | Br |
| 2-$OCF_2H$ | H | H | Br | 2-$OCF_2H$ | H | H | Br |
| 2-F | 4-F | H | Br | 2-F | 4-F | H | Br |
| 2-Cl | 4-F | H | Br | 2-Cl | 4-F | H | Br |
| 2-Br | 4-F | H | Br | 2-Br | 4-F | H | Br |
| 2-I | 4-F | H | Br | 2-I | 4-F | H | Br |
| 2-Me | 4-F | H | Br | 2-Me | 4-F | H | Br |
| 2-Et | 4-F | H | Br | 2-Et | 4-F | H | Br |
| 2-$CF_3$ | 4-F | H | Br | 2-$CF_3$ | 4-F | H | Br |
| 2-$OCF_2H$ | 4-F | H | Br | 2-$OCF_2H$ | 4-F | H | Br |
| 2-F | 4-Cl | H | Br | 2-F | 4-Cl | H | Br |
| 2-Cl | 4-Cl | H | Br | 2-Cl | 4-Cl | H | Br |
| 2-Br | 4-Cl | H | Br | 2-Br | 4-Cl | H | Br |
| 2-I | 4-Cl | H | Br | 2-I | 4-Cl | H | Br |
| 2-Me | 4-Cl | H | Br | 2-Me | 4-Cl | H | Br |
| 2-Et | 4-Cl | H | Br | 2-Et | 4-Cl | H | Br |
| 2-$CF_3$ | 4-Cl | H | Br | 2-$CF_3$ | 4-Cl | H | Br |
| 2-$OCF_2H$ | 4-Cl | H | Br | 2-$OCF_2H$ | 4-Cl | H | Br |
| 2-F | 4-Br | H | Br | 2-F | 4-Br | H | Br |
| 2-Cl | 4-Br | H | Br | 2-Cl | 4-Br | H | Br |
| 2-Br | 4-Br | H | Br | 2-Br | 4-Br | H | Br |

TABLE 4-continued

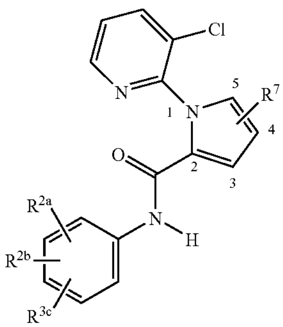

| R⁷ is attached to the 5 position | | | | R⁷ is attached to the 4 position | | | |
|---|---|---|---|---|---|---|---|
| $R^{2a}$ | $R^{2b}$ | $R^{2c}$ | $R^7$ | $R^{2a}$ | $R^{2b}$ | $R^{2c}$ | $R^7$ |
| 2-I | 4-Br | H | Br | 2-I | 4-Br | H | Br |
| 2-Me | 4-Br | H | Br | 2-Me | 4-Br | H | Br |
| 2-Et | 4-Br | H | Br | 2-Et | 4-Br | H | Br |
| 2-$CF_3$ | 4-Br | H | Br | 2-$CF_3$ | 4-Br | H | Br |
| 2-$OCF_2H$ | 4-Br | H | Br | 2-$OCF_2H$ | 4-Br | H | Br |
| 2-F | 4-I | H | Br | 2-F | 4-I | H | Br |
| 2-Cl | 4-I | H | Br | 2-Cl | 4-I | H | Br |
| 2-Br | 4-I | H | Br | 2-Br | 4-I | H | Br |
| 2-I | 4-I | H | Br | 2-I | 4-I | H | Br |
| 2-Me | 4-I | H | Br | 2-Me | 4-I | H | Br |
| 2-Et | 4-I | H | Br | 2-Et | 4-I | H | Br |
| 2-$CF_3$ | 4-I | H | Br | 2-$CF_3$ | 4-I | H | Br |
| 2-F | 4-$CF_3$ | H | Br | 2-F | 4-$CF_3$ | H | Br |
| 2-Cl | 4-$CF_3$ | H | Br | 2-Cl | 4-$CF_3$ | H | Br |
| 2-Br | 4-$CF_3$ | H | Br | 2-Br | 4-$CF_3$ | H | Br |
| 2-I | 4-$CF_3$ | H | Br | 2-I | 4-$CF_3$ | H | Br |
| 2-Me | 4-$CF_3$ | H | Br | 2-Me | 4-$CF_3$ | H | Br |
| 2-Et | 4-$CF_3$ | H | Br | 2-Et | 4-$CF_3$ | H | Br |
| 2-$CF_3$ | 4-$CF_3$ | H | Br | 2-$CF_3$ | 4-$CF_3$ | H | Br |
| 2-F | 4-CN | H | Br | 2-F | 4-CN | H | Br |
| 2-Cl | 4-CN | H | Br | 2-Cl | 4-CN | H | Br |
| 2-Br | 4-CN | H | Br | 2-Br | 4-CN | H | Br |
| 2-I | 4-CN | H | Br | 2-I | 4-CN | H | Br |
| 2-Me | 4-CN | H | Br | 2-Me | 4-CN | H | Br |
| 2-Et | 4-CN | H | Br | 2-Et | 4-CN | H | Br |
| 2-$CF_3$ | 4-CN | H | Br | 2-$CF_3$ | 4-CN | H | Br |
| 2-F | H | 6-Cl | Br | 2-F | H | 6-Cl | Br |
| 2-Cl | H | 6-Cl | Br | 2-Cl | H | 6-Cl | Br |
| 2-Br | H | 6-Cl | Br | 2-Br | H | 6-Cl | Br |
| 2-I | H | 6-Cl | Br | 2-I | H | 6-Cl | Br |
| 2-Me | H | 6-Cl | Br | 2-Me | H | 6-Cl | Br |
| 2-Et | H | 6-Cl | Br | 2-Et | H | 6-Cl | Br |
| 2-$CF_3$ | H | 6-Cl | Br | 2-$CF_3$ | H | 6-Cl | Br |
| 2-$OCF_2H$ | H | 6-Cl | Br | 2-$OCF_2H$ | H | 6-Cl | Br |
| 2-F | H | 6-Br | Br | 2-F | H | 6-Br | Br |
| 2-Cl | H | 6-Br | Br | 2-Cl | H | 6-Br | Br |
| 2-Br | H | 6-Br | Br | 2-Br | H | 6-Br | Br |
| 2-I | H | 6-Br | Br | 2-I | H | 6-Br | Br |
| 2-Me | H | 6-Br | Br | 2-Me | H | 6-Br | Br |
| 2-Et | H | 6-Br | Br | 2-Et | H | 6-Br | Br |
| 2-$CF_3$ | H | 6-Br | Br | 2-$CF_3$ | H | 6-Br | Br |
| 2-$OCF_2H$ | H | 6-Br | Br | 2-$OCF_2H$ | H | 6-Br | Br |
| 2-F | H | 6-F | Br | 2-F | H | 6-F | Br |
| 2-Cl | H | 6-F | Br | 2-Cl | H | 6-F | Br |
| 2-Br | H | 6-F | Br | 2-Br | H | 6-F | Br |
| 2-I | H | 6-F | Br | 2-I | H | 6-F | Br |
| 2-Me | H | 6-F | Br | 2-Me | H | 6-F | Br |
| 2-Et | H | 6-F | Br | 2-Et | H | 6-F | Br |
| 2-$CF_3$ | H | 6-F | Br | 2-$CF_3$ | H | 6-F | Br |
| 2-$OCF_2H$ | H | 6-F | Br | 2-$OCF_2H$ | H | 6-F | Br |
| 2-F | 4-F | 6-Cl | Br | 2-F | 4-F | 6-Cl | Br |
| 2-Cl | 4-F | 6-Cl | Br | 2-Cl | 4-F | 6-Cl | Br |
| 2-Br | 4-F | 6-Cl | Br | 2-Br | 4-F | 6-Cl | Br |
| 2-I | 4-F | 6-Cl | Br | 2-I | 4-F | 6-Cl | Br |
| 2-Me | 4-F | 6-Cl | Br | 2-Me | 4-F | 6-Cl | Br |
| 2-Et | 4-F | 6-Cl | Br | 2-Et | 4-F | 6-Cl | Br |
| 2-$CF_3$ | 4-F | 6-Cl | Br | 2-$CF_3$ | 4-F | 6-Cl | Br |
| 2-$OCF_2H$ | 4-F | 6-Cl | Br | 2-$OCF_2H$ | 4-F | 6-Cl | Br |
| 2-F | 4-F | 6-Br | Br | 2-F | 4-F | 6-Br | Br |

TABLE 4-continued

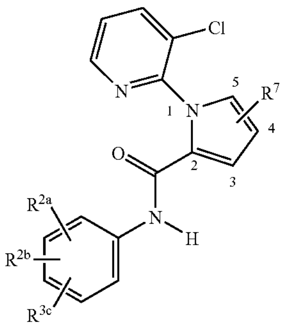

| R⁷ is attached to the 5 position | | | | R⁷ is attached to the 4 position | | | |
|---|---|---|---|---|---|---|---|
| $R^{2a}$ | $R^{2b}$ | $R^{2c}$ | $R^7$ | $R^{2a}$ | $R^{2b}$ | $R^{2c}$ | $R^7$ |
| 2-Cl | 4-F | 6-Br | Br | 2-Cl | 4-F | 6-Br | Br |
| 2-Br | 4-F | 6-Br | Br | 2-Br | 4-F | 6-Br | Br |
| 2-I | 4-F | 6-Br | Br | 2-I | 4-F | 6-Br | Br |
| 2-Me | 4-F | 6-Br | Br | 2-Me | 4-F | 6-Br | Br |
| 2-Et | 4-F | 6-Br | Br | 2-Et | 4-F | 6-Br | Br |
| 2-$CF_3$ | 4-F | 6-Br | Br | 2-$CF_3$ | 4-F | 6-Br | Br |
| 2-$OCF_2H$ | 4-F | 6-Br | Br | 2-$OCF_2H$ | 4-F | 6-Br | Br |
| 2-F | 4-F | 6-F | Br | 2-F | 4-F | 6-F | Br |
| 2-Cl | 4-F | 6-F | Br | 2-Cl | 4-F | 6-F | Br |
| 2-Br | 4-F | 6-F | Br | 2-Br | 4-F | 6-F | Br |
| 2-I | 4-F | 6-F | Br | 2-I | 4-F | 6-F | Br |
| 2-Me | 4-F | 6-F | Br | 2-Me | 4-F | 6-F | Br |
| 2-Et | 4-F | 6-F | Br | 2-Et | 4-F | 6-F | Br |
| 2-$CF_3$ | 4-F | 6-F | Br | 2-$CF_3$ | 4-F | 6-F | Br |
| 2-$OCF_2H$ | 4-F | 6-F | Br | 2-$OCF_2H$ | 4-F | 6-F | Br |
| 2-F | 4-Cl | 6-Cl | Br | 2-F | 4-Cl | 6-Cl | Br |
| 2-Cl | 4-Cl | 6-Cl | Br | 2-Cl | 4-Cl | 6-Cl | Br |
| 2-Br | 4-Cl | 6-Cl | Br | 2-Br | 4-Cl | 6-Cl | Br |
| 2-I | 4-Cl | 6-Cl | Br | 2-I | 4-Cl | 6-Cl | Br |
| 2-Me | 4-Cl | 6-Cl | Br | 2-Me | 4-Cl | 6-Cl | Br |
| 2-Et | 4-Cl | 6-Cl | Br | 2-Et | 4-Cl | 6-Cl | Br |
| 2-$CF_3$ | 4-Cl | 6-Cl | Br | 2-$CF_3$ | 4-Cl | 6-Cl | Br |
| 2-$OCF_2H$ | 4-Cl | 6-Cl | Br | 2-$OCF_2H$ | 4-Cl | 6-Cl | Br |
| 2-F | 4-Cl | 6-Br | Br | 2-F | 4-Cl | 6-Br | Br |
| 2-Cl | 4-Cl | 6-Br | Br | 2-Cl | 4-Cl | 6-Br | Br |
| 2-Br | 4-Cl | 6-Br | Br | 2-Br | 4-Cl | 6-Br | Br |
| 2-I | 4-Cl | 6-Br | Br | 2-I | 4-Cl | 6-Br | Br |
| 2-Me | 4-Cl | 6-Br | Br | 2-Me | 4-Cl | 6-Br | Br |
| 2-Et | 4-Cl | 6-Br | Br | 2-Et | 4-Cl | 6-Br | Br |
| 2-$CF_3$ | 4-Cl | 6-Br | Br | 2-$CF_3$ | 4-Cl | 6-Br | Br |
| 2-$OCF_2H$ | 4-Cl | 6-Br | Br | 2-$OCF_2H$ | 4-Cl | 6-Br | Br |
| 2-F | 4-Cl | 6-F | Br | 2-F | 4-Cl | 6-F | Br |
| 2-Cl | 4-Cl | 6-F | Br | 2-Cl | 4-Cl | 6-F | Br |
| 2-Br | 4-Cl | 6-F | Br | 2-Br | 4-Cl | 6-F | Br |
| 2-I | 4-Cl | 6-F | Br | 2-I | 4-Cl | 6-F | Br |
| 2-Me | 4-Cl | 6-F | Br | 2-Me | 4-Cl | 6-F | Br |
| 2-Et | 4-Cl | 6-F | Br | 2-Et | 4-Cl | 6-F | Br |
| 2-$CF_3$ | 4-Cl | 6-F | Br | 2-$CF_3$ | 4-Cl | 6-F | Br |
| 2-$OCF_2H$ | 4-Cl | 6-F | Br | 2-$OCF_2H$ | 4-Cl | 6-F | Br |
| 2-F | 4-Br | 6-Cl | Br | 2-F | 4-Br | 6-Cl | Br |
| 2-Cl | 4-Br | 6-Cl | Br | 2-Cl | 4-Br | 6-Cl | Br |
| 2-Br | 4-Br | 6-Cl | Br | 2-Br | 4-Br | 6-Cl | Br |
| 2-I | 4-Br | 6-Cl | Br | 2-I | 4-Br | 6-Cl | Br |
| 2-Me | 4-Br | 6-Cl | Br | 2-Me | 4-Br | 6-Cl | Br |
| 2-Et | 4-Br | 6-Cl | Br | 2-Et | 4-Br | 6-Cl | Br |
| 2-$CF_3$ | 4-Br | 6-Cl | Br | 2-$CF_3$ | 4-Br | 6-Cl | Br |
| 2-$OCF_2H$ | 4-Br | 6-Cl | Br | 2-$OCF_2H$ | 4-Br | 6-Cl | Br |
| 2-F | 4-Br | 6-Br | Br | 2-F | 4-Br | 6-Br | Br |
| 2-Cl | 4-Br | 6-Br | Br | 2-Cl | 4-Br | 6-Br | Br |
| 2-Br | 4-Br | 6-Br | Br | 2-Br | 4-Br | 6-Br | Br |
| 2-I | 4-Br | 6-Br | Br | 2-I | 4-Br | 6-Br | Br |
| 2-Me | 4-Br | 6-Br | Br | 2-Me | 4-Br | 6-Br | Br |
| 2-Et | 4-Br | 6-Br | Br | 2-Et | 4-Br | 6-Br | Br |
| 2-$CF_3$ | 4-Br | 6-Br | Br | 2-$CF_3$ | 4-Br | 6-Br | Br |
| 2-$OCF_2H$ | 4-Br | 6-Br | Br | 2-$OCF_2H$ | 4-Br | 6-Br | Br |
| 2-F | 4-Br | 6-F | Br | 2-F | 4-Br | 6-F | Br |
| 2-Cl | 4-Br | 6-F | Br | 2-Cl | 4-Br | 6-F | Br |
| 2-Br | 4-Br | 6-F | Br | 2-Br | 4-Br | 6-F | Br |
| 2-I | 4-Br | 6-F | Br | 2-I | 4-Br | 6-F | Br |

TABLE 4-continued

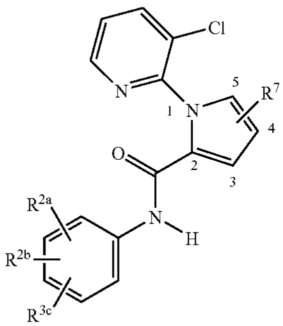

| $R^7$ is attached to the 5 position | | | | $R^7$ is attached to the 4 position | | | |
|---|---|---|---|---|---|---|---|
| $R^{2a}$ | $R^{2b}$ | $R^{2c}$ | $R^7$ | $R^{2a}$ | $R^{2b}$ | $R^{2c}$ | $R^7$ |
| 2-Me | 4-Br | 6-F | Br | 2-Me | 4-Br | 6-F | Br |
| 2-Et | 4-Br | 6-F | Br | 2-Et | 4-Br | 6-F | Br |
| 2-$CF_3$ | 4-Br | 6-F | Br | 2-$CF_3$ | 4-Br | 6-F | Br |
| 2-$OCF_2H$ | 4-Br | 6-F | Br | 2-$OCF_2H$ | 4-Br | 6-F | Br |

TABLE 5

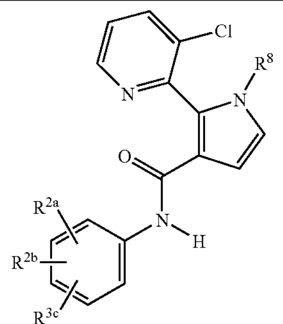

| $R^{2a}$ | $R^{2b}$ | $R^{2c}$ | $R^8$ | $R^{2a}$ | $R^{2b}$ | $R^{2c}$ | $R^8$ |
|---|---|---|---|---|---|---|---|
| H | H | H | Me | H | H | H | $OCH_2CF_3$ |
| 2-F | H | H | Me | 2-F | H | H | $OCH_2CF_3$ |
| 2-Cl | H | H | Me | 2-Cl | H | H | $OCH_2CF_3$ |
| 2-Br | H | H | Me | 2-Br | H | H | $OCH_2CF_3$ |
| 2-I | H | H | Me | 2-I | H | H | $OCH_2CF_3$ |
| 2-Me | H | H | Me | 2-Me | H | H | $OCH_2CF_3$ |
| 2-Et | H | H | Me | 2-Et | H | H | $OCH_2CF_3$ |
| 2-$CF_3$ | H | H | Me | 2-$CF_3$ | H | H | $OCH_2CF_3$ |
| 2-$OCF_2H$ | H | H | Me | 2-$OCF_2H$ | H | H | $OCH_2CF_3$ |
| 2-F | 4-F | H | Me | 2-F | 4-F | H | $OCH_2CF_3$ |
| 2-Cl | 4-F | H | Me | 2-Cl | 4-F | H | $OCH_2CF_3$ |
| 2-Br | 4-F | H | Me | 2-Br | 4-F | H | $OCH_2CF_3$ |
| 2-I | 4-F | H | Me | 2-I | 4-F | H | $OCH_2CF_3$ |
| 2-Me | 4-F | H | Me | 2-Me | 4-F | H | $OCH_2CF_3$ |
| 2-Et | 4-F | H | Me | 2-Et | 4-F | H | $OCH_2CF_3$ |
| 2-$CF_3$ | 4-F | H | Me | 2-$CF_3$ | 4-F | H | $OCH_2CF_3$ |
| 2-$OCF_2H$ | 4-F | H | Me | 2-$OCF_2H$ | 4-F | H | $OCH_2CF_3$ |
| 2-F | 4-Cl | H | Me | 2-F | 4-Cl | H | $OCH_2CF_3$ |
| 2-Cl | 4-Cl | H | Me | 2-Cl | 4-Cl | H | $OCH_2CF_3$ |
| 2-Br | 4-Cl | H | Me | 2-Br | 4-Cl | H | $OCH_2CF_3$ |
| 2-I | 4-Cl | H | Me | 2-I | 4-Cl | H | $OCH_2CF_3$ |
| 2-Me | 4-Cl | H | Me | 2-Me | 4-Cl | H | $OCH_2CF_3$ |
| 2-Et | 4-Cl | H | Me | 2-Et | 4-Cl | H | $OCH_2CF_3$ |
| 2-$CF_3$ | 4-Cl | H | Me | 2-$CF_3$ | 4-Cl | H | $OCH_2CF_3$ |
| 2-$OCF_2H$ | 4-Cl | H | Me | 2-$OCF_2H$ | 4-Cl | H | $OCH_2CF_3$ |
| 2-F | 4-Br | H | Me | 2-F | 4-Br | H | $OCH_2CF_3$ |
| 2-Cl | 4-Br | H | Me | 2-Cl | 4-Br | H | $OCH_2CF_3$ |
| 2-Br | 4-Br | H | Me | 2-Br | 4-Br | H | $OCH_2CF_3$ |
| 2-I | 4-Br | H | Me | 2-I | 4-Br | H | $OCH_2CF_3$ |
| 2-Me | 4-Br | H | Me | 2-Me | 4-Br | H | $OCH_2CF_3$ |
| 2-Et | 4-Br | H | Me | 2-Et | 4-Br | H | $OCH_2CF_3$ |

TABLE 5-continued

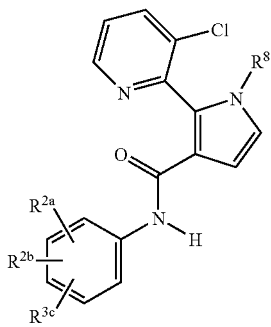

| $R^{2a}$ | $R^{2b}$ | $R^{2c}$ | $R^8$ | $R^{2a}$ | $R^{2b}$ | $R^{2c}$ | $R^8$ |
|---|---|---|---|---|---|---|---|
| 2-$CF_3$ | 4-Br | H | Me | 2-$CF_3$ | 4-Br | H | $OCH_2CF_3$ |
| 2-$OCF_2H$ | 4-Br | H | Me | 2-$OCF_2H$ | 4-Br | H | $OCH_2CF_3$ |
| 2-F | 4-I | H | Me | 2-F | 4-I | H | $OCH_2CF_3$ |
| 2-Cl | 4-I | H | Me | 2-Cl | 4-I | H | $OCH_2CF_3$ |
| 2-Br | 4-I | H | Me | 2-Br | 4-I | H | $OCH_2CF_3$ |
| 2-I | 4-I | H | Me | 2-I | 4-I | H | $OCH_2CF_3$ |
| 2-Me | 4-I | H | Me | 2-Me | 4-I | H | $OCH_2CF_3$ |
| 2-Et | 4-I | H | Me | 2-Et | 4-I | H | $OCH_2CF_3$ |
| 2-$CF_3$ | 4-I | H | Me | 2-$CF_3$ | 4-I | H | $OCH_2CF_3$ |
| 2-F | 4-$CF_3$ | H | Me | 2-F | 4-$CF_3$ | H | $OCH_2CF_3$ |
| 2-Cl | 4-$CF_3$ | H | Me | 2-Cl | 4-$CF_3$ | H | $OCH_2CF_3$ |
| 2-Br | 4-$CF_3$ | H | Me | 2-Br | 4-$CF_3$ | H | $OCH_2CF_3$ |
| 2-I | 4-$CF_3$ | H | Me | 2-I | 4-$CF_3$ | H | $OCH_2CF_3$ |
| 2-Me | 4-$CF_3$ | H | Me | 2-Me | 4-$CF_3$ | H | $OCH_2CF_3$ |
| 2-Et | 4-$CF_3$ | H | Me | 2-Et | 4-$CF_3$ | H | $OCH_2CF_3$ |
| 2-$CF_3$ | 4-$CF_3$ | H | Me | 2-$CF_3$ | 4-$CF_3$ | H | $OCH_2CF_3$ |
| 2-F | 4-CN | H | Me | 2-F | 4-CN | H | $OCH_2CF_3$ |
| 2-Cl | 4-CN | H | Me | 2-Cl | 4-CN | H | $OCH_2CF_3$ |
| 2-Br | 4-CN | H | Me | 2-Br | 4-CN | H | $OCH_2CF_3$ |
| 2-I | 4-CN | H | Me | 2-I | 4-CN | H | $OCH_2CF_3$ |
| 2-Me | 4-CN | H | Me | 2-Me | 4-CN | H | $OCH_2CF_3$ |
| 2-Et | 4-CN | H | Me | 2-Et | 4-CN | H | $OCH_2CF_3$ |
| 2-$CF_3$ | 4-CN | H | Me | 2-$CF_3$ | 4-CN | H | $OCH_2CF_3$ |
| 2-F | H | 6-Cl | Me | 2-F | H | 6-Cl | $OCH_2CF_3$ |
| 2-Cl | H | 6-Cl | Me | 2-Cl | H | 6-Cl | $OCH_2CF_3$ |
| 2-Br | H | 6-Cl | Me | 2-Br | H | 6-Cl | $OCH_2CF_3$ |
| 2-I | H | 6-Cl | Me | 2-I | H | 6-Cl | $OCH_2CF_3$ |
| 2-Me | H | 6-Cl | Me | 2-Me | H | 6-Cl | $OCH_2CF_3$ |
| 2-Et | H | 6-Cl | Me | 2-Et | H | 6-Cl | $OCH_2CF_3$ |
| 2-$CF_3$ | H | 6-Cl | Me | 2-$CF_3$ | H | 6-Cl | $OCH_2CF_3$ |
| 2-$OCF_2H$ | H | 6-Cl | Me | 2-$OCF_2H$ | H | 6-Cl | $OCH_2CF_3$ |
| 2-F | H | 6-Br | Me | 2-F | H | 6-Br | $OCH_2CF_3$ |
| 2-Cl | H | 6-Br | Me | 2-Cl | H | 6-Br | $OCH_2CF_3$ |
| 2-Br | H | 6-Br | Me | 2-Br | H | 6-Br | $OCH_2CF_3$ |
| 2-I | H | 6-Br | Me | 2-I | H | 6-Br | $OCH_2CF_3$ |
| 2-Me | H | 6-Br | Me | 2-Me | H | 6-Br | $OCH_2CF_3$ |
| 2-Et | H | 6-Br | Me | 2-Et | H | 6-Br | $OCH_2CF_3$ |
| 2-$CF_3$ | H | 6-Br | Me | 2-$CF_3$ | H | 6-Br | $OCH_2CF_3$ |
| 2-$OCF_2H$ | H | 6-Br | Me | 2-$OCF_2H$ | H | 6-Br | $OCH_2CF_3$ |
| 2-F | H | 6-F | Me | 2-F | H | 6-F | $OCH_2CF_3$ |
| 2-Cl | H | 6-F | Me | 2-Cl | H | 6-F | $OCH_2CF_3$ |
| 2-Br | H | 6-F | Me | 2-Br | H | 6-F | $OCH_2CF_3$ |
| 2-I | H | 6-F | Me | 2-I | H | 6-F | $OCH_2CF_3$ |
| 2-Me | H | 6-F | Me | 2-Me | H | 6-F | $OCH_2CF_3$ |
| 2-Et | H | 6-F | Me | 2-Et | H | 6-F | $OCH_2CF_3$ |
| 2-$CF_3$ | H | 6-F | Me | 2-$CF_3$ | H | 6-F | $OCH_2CF_3$ |
| 2-$OCF_2H$ | H | 6-F | Me | 2-$OCF_2H$ | H | 6-F | $OCH_2CF_3$ |
| 2-F | 4-F | 6-Cl | Me | 2-F | 4-F | 6-Cl | $OCH_2CF_3$ |
| 2-Cl | 4-F | 6-Cl | Me | 2-Cl | 4-F | 6-Cl | $OCH_2CF_3$ |
| 2-Br | 4-F | 6-Cl | Me | 2-Br | 4-F | 6-Cl | $OCH_2CF_3$ |
| 2-I | 4-F | 6-Cl | Me | 2-I | 4-F | 6-Cl | $OCH_2CF_3$ |
| 2-Me | 4-F | 6-Cl | Me | 2-Me | 4-F | 6-Cl | $OCH_2CF_3$ |
| 2-Et | 4-F | 6-Cl | Me | 2-Et | 4-F | 6-Cl | $OCH_2CF_3$ |
| 2-$CF_3$ | 4-F | 6-Cl | Me | 2-$CF_3$ | 4-F | 6-Cl | $OCH_2CF_3$ |
| 2-$OCF_2H$ | 4-F | 6-Cl | Me | 2-$OCF_2H$ | 4-F | 6-Cl | $OCH_2CF_3$ |
| 2-F | 4-F | 6-Br | Me | 2-F | 4-F | 6-Br | $OCH_2CF_3$ |
| 2-Cl | 4-F | 6-Br | Me | 2-Cl | 4-F | 6-Br | $OCH_2CF_3$ |
| 2-Br | 4-F | 6-Br | Me | 2-Br | 4-F | 6-Br | $OCH_2CF_3$ |
| 2-I | 4-F | 6-Br | Me | 2-I | 4-F | 6-Br | $OCH_2CF_3$ |
| 2-Me | 4-F | 6-Br | Me | 2-Me | 4-F | 6-Br | $OCH_2CF_3$ |

TABLE 5-continued

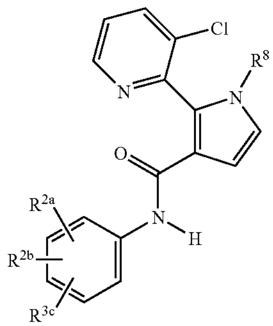

| $R^{2a}$ | $R^{2b}$ | $R^{2c}$ | $R^8$ | $R^{2a}$ | $R^{2b}$ | $R^{2c}$ | $R^8$ |
|---|---|---|---|---|---|---|---|
| 2-Et | 4-F | 6-Br | Me | 2-Et | 4-F | 6-Br | $OCH_2CF_3$ |
| 2-$CF_3$ | 4-F | 6-Br | Me | 2-$CF_3$ | 4-F | 6-Br | $OCH_2CF_3$ |
| 2-$OCF_2H$ | 4-F | 6-Br | Me | 2-$OCF_2H$ | 4-F | 6-Br | $OCH_2CF_3$ |
| 2-F | 4-F | 6-F | Me | 2-F | 4-F | 6-F | $OCH_2CF_3$ |
| 2-Cl | 4-F | 6-F | Me | 2-Cl | 4-F | 6-F | $OCH_2CF_3$ |
| 2-Br | 4-F | 6-F | Me | 2-Br | 4-F | 6-F | $OCH_2CF_3$ |
| 2-I | 4-F | 6-F | Me | 2-I | 4-F | 6-F | $OCH_2CF_3$ |
| 2-Me | 4-F | 6-F | Me | 2-Me | 4-F | 6-F | $OCH_2CF_3$ |
| 2-Et | 4-F | 6-F | Me | 2-Et | 4-F | 6-F | $OCH_2CF_3$ |
| 2-$CF_3$ | 4-F | 6-F | Me | 2-$CF_3$ | 4-F | 6-F | $OCH_2CF_3$ |
| 2-$OCF_2H$ | 4-F | 6-F | Me | 2-$OCF_2H$ | 4-F | 6-F | $OCH_2CF_3$ |
| 2-F | 4-Cl | 6-Cl | Me | 2-F | 4-Cl | 6-Cl | $OCH_2CF_3$ |
| 2-Cl | 4-Cl | 6-Cl | Me | 2-Cl | 4-Cl | 6-Cl | $OCH_2CF_3$ |
| 2-Br | 4-Cl | 6-Cl | Me | 2-Br | 4-Cl | 6-Cl | $OCH_2CF_3$ |
| 2-I | 4-Cl | 6-Cl | Me | 2-I | 4-Cl | 6-Cl | $OCH_2CF_3$ |
| 2-Me | 4-Cl | 6-Cl | Me | 2-Me | 4-Cl | 6-Cl | $OCH_2CF_3$ |
| 2-Et | 4-Cl | 6-Cl | Me | 2-Et | 4-Cl | 6-Cl | $OCH_2CF_3$ |
| 2-$CF_3$ | 4-Cl | 6-Cl | Me | 2-$CF_3$ | 4-Cl | 6-Cl | $OCH_2CF_3$ |
| 2-$OCF_2H$ | 4-Cl | 6-Cl | Me | 2-$OCF_2H$ | 4-Cl | 6-Cl | $OCH_2CF_3$ |
| 2-F | 4-Cl | 6-Br | Me | 2-F | 4-Cl | 6-Br | $OCH_2CF_3$ |
| 2-Cl | 4-Cl | 6-Br | Me | 2-Cl | 4-Cl | 6-Br | $OCH_2CF_3$ |
| 2-Br | 4-Cl | 6-Br | Me | 2-Br | 4-Cl | 6-Br | $OCH_2CF_3$ |
| 2-I | 4-Cl | 6-Br | Me | 2-I | 4-Cl | 6-Br | $OCH_2CF_3$ |
| 2-Me | 4-Cl | 6-Br | Me | 2-Me | 4-Cl | 6-Br | $OCH_2CF_3$ |
| 2-Et | 4-Cl | 6-Br | Me | 2-Et | 4-Cl | 6-Br | $OCH_2CF_3$ |
| 2-$CF_3$ | 4-Cl | 6-Br | Me | 2-$CF_3$ | 4-Cl | 6-Br | $OCH_2CF_3$ |
| 2-$OCF_2H$ | 4-Cl | 6-Br | Me | 2-$OCF_2H$ | 4-Cl | 6-Br | $OCH_2CF_3$ |
| 2-F | 4-Cl | 6-F | Me | 2-F | 4-Cl | 6-F | $OCH_2CF_3$ |
| 2-Cl | 4-Cl | 6-F | Me | 2-Cl | 4-Cl | 6-F | $OCH_2CF_3$ |
| 2-Br | 4-Cl | 6-F | Me | 2-Br | 4-Cl | 6-F | $OCH_2CF_3$ |
| 2-I | 4-Cl | 6-F | Me | 2-I | 4-Cl | 6-F | $OCH_2CF_3$ |
| 2-Me | 4-Cl | 6-F | Me | 2-Me | 4-Cl | 6-F | $OCH_2CF_3$ |
| 2-Et | 4-Cl | 6-F | Me | 2-Et | 4-Cl | 6-F | $OCH_2CF_3$ |
| 2-$CF_3$ | 4-Cl | 6-F | Me | 2-$CF_3$ | 4-Cl | 6-F | $OCH_2CF_3$ |
| 2-$OCF_2H$ | 4-Cl | 6-F | Me | 2-$OCF_2H$ | 4-Cl | 6-F | $OCH_2CF_3$ |
| 2-F | 4-Br | 6-Cl | Me | 2-F | 4-Br | 6-Cl | $OCH_2CF_3$ |
| 2-Cl | 4-Br | 6-Cl | Me | 2-Cl | 4-Br | 6-Cl | $OCH_2CF_3$ |
| 2-Br | 4-Br | 6-Cl | Me | 2-Br | 4-Br | 6-Cl | $OCH_2CF_3$ |
| 2-I | 4-Br | 6-Cl | Me | 2-I | 4-Br | 6-Cl | $OCH_2CF_3$ |
| 2-Me | 4-Br | 6-Cl | Me | 2-Me | 4-Br | 6-Cl | $OCH_2CF_3$ |
| 2-Et | 4-Br | 6-Cl | Me | 2-Et | 4-Br | 6-Cl | $OCH_2CF_3$ |
| 2-$CF_3$ | 4-Br | 6-Cl | Me | 2-$CF_3$ | 4-Br | 6-Cl | $OCH_2CF_3$ |
| 2-$OCF_2H$ | 4-Br | 6-Cl | Me | 2-$OCF_2H$ | 4-Br | 6-Cl | $OCH_2CF_3$ |
| 2-F | 4-Br | 6-Br | Me | 2-F | 4-Br | 6-Br | $OCH_2CF_3$ |
| 2-Cl | 4-Br | 6-Br | Me | 2-Cl | 4-Br | 6-Br | $OCH_2CF_3$ |
| 2-Br | 4-Br | 6-Br | Me | 2-Br | 4-Br | 6-Br | $OCH_2CF_3$ |
| 2-I | 4-Br | 6-Br | Me | 2-I | 4-Br | 6-Br | $OCH_2CF_3$ |
| 2-Me | 4-Br | 6-Br | Me | 2-Me | 4-Br | 6-Br | $OCH_2CF_3$ |
| 2-Et | 4-Br | 6-Br | Me | 2-Et | 4-Br | 6-Br | $OCH_2CF_3$ |
| 2-$CF_3$ | 4-Br | 6-Br | Me | 2-$CF_3$ | 4-Br | 6-Br | $OCH_2CF_3$ |
| 2-$OCF_2H$ | 4-Br | 6-Br | Me | 2-$OCF_2H$ | 4-Br | 6-Br | $OCH_2CF_3$ |
| 2-F | 4-Br | 6-F | Me | 2-F | 4-Br | 6-F | $OCH_2CF_3$ |
| 2-Cl | 4-Br | 6-F | Me | 2-Cl | 4-Br | 6-F | $OCH_2CF_3$ |
| 2-Br | 4-Br | 6-F | Me | 2-Br | 4-Br | 6-F | $OCH_2CF_3$ |
| 2-I | 4-Br | 6-F | Me | 2-I | 4-Br | 6-F | $OCH_2CF_3$ |
| 2-Me | 4-Br | 6-F | Me | 2-Me | 4-Br | 6-F | $OCH_2CF_3$ |
| 2-Et | 4-Br | 6-F | Me | 2-Et | 4-Br | 6-F | $OCH_2CF_3$ |
| 2-$CF_3$ | 4-Br | 6-F | Me | 2-$CF_3$ | 4-Br | 6-F | $OCH_2CF_3$ |
| 2-$OCF_2H$ | 4-Br | 6-F | Me | 2-$OCF_2H$ | 4-Br | 6-F | $OCH_2CF_3$ |
| 2-F | H | H | $CHF_2$ | 2-$CF_3$ | H | 6-F | $CHF_2$ |

TABLE 5-continued

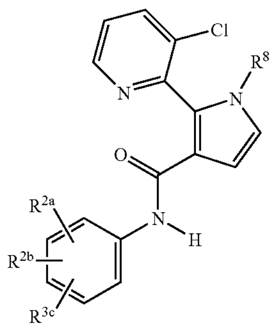

| $R^{2a}$ | $R^{2b}$ | $R^{2c}$ | $R^8$ | $R^{2a}$ | $R^{2b}$ | $R^{2c}$ | $R^8$ |
|---|---|---|---|---|---|---|---|
| 2-Cl | H | H | $CHF_2$ | 2-$OCF_2H$ | H | 6-F | $CHF_2$ |
| 2-Br | H | H | $CHF_2$ | 2-F | 4-F | 6-Cl | $CHF_2$ |
| 2-I | H | H | $CHF_2$ | 2-Cl | 4-F | 6-Cl | $CHF_2$ |
| 2-Me | H | H | $CHF_2$ | 2-Br | 4-F | 6-Cl | $CHF_2$ |
| 2-Et | H | H | $CHF_2$ | 2-I | 4-F | 6-Cl | $CHF_2$ |
| 2-$CF_3$ | H | H | $CHF_2$ | 2-Me | 4-F | 6-Cl | $CHF_2$ |
| 2-$OCF_2H$ | H | H | $CHF_2$ | 2-Et | 4-F | 6-Cl | $CHF_2$ |
| 2-F | 4-F | H | $CHF_2$ | 2-$CF_3$ | 4-F | 6-Cl | $CHF_2$ |
| 2-Cl | 4-F | H | $CHF_2$ | 2-$OCF_2H$ | 4-F | 6-Cl | $CHF_2$ |
| 2-Br | 4-F | H | $CHF_2$ | 2-F | 4-F | 6-Br | $CHF_2$ |
| 2-I | 4-F | H | $CHF_2$ | 2-Cl | 4-F | 6-Br | $CHF_2$ |
| 2-Me | 4-F | H | $CHF_2$ | 2-Br | 4-F | 6-Br | $CHF_2$ |
| 2-Et | 4-F | H | $CHF_2$ | 2-I | 4-F | 6-Br | $CHF_2$ |
| 2-$CF_3$ | 4-F | H | $CHF_2$ | 2-Me | 4-F | 6-Br | $CHF_2$ |
| 2-$OCF_2H$ | 4-F | H | $CHF_2$ | 2-Et | 4-F | 6-Br | $CHF_2$ |
| 2-F | 4-Cl | H | $CHF_2$ | 2-$CF_3$ | 4-F | 6-Br | $CHF_2$ |
| 2-Cl | 4-Cl | H | $CHF_2$ | 2-$OCF_2H$ | 4-F | 6-Br | $CHF_2$ |
| 2-Br | 4-Cl | H | $CHF_2$ | 2-F | 4-F | 6-F | $CHF_2$ |
| 2-I | 4-Cl | H | $CHF_2$ | 2-Cl | 4-F | 6-F | $CHF_2$ |
| 2-Me | 4-Cl | H | $CHF_2$ | 2-Br | 4-F | 6-F | $CHF_2$ |
| 2-Et | 4-Cl | H | $CHF_2$ | 2-I | 4-F | 6-F | $CHF_2$ |
| 2-$CF_3$ | 4-Cl | H | $CHF_2$ | 2-Me | 4-F | 6-F | $CHF_2$ |
| 2-$OCF_2H$ | 4-Cl | H | $CHF_2$ | 2-Et | 4-F | 6-F | $CHF_2$ |
| 2-F | 4-Br | H | $CHF_2$ | 2-$CF_3$ | 4-F | 6-F | $CHF_2$ |
| 2-Cl | 4-Br | H | $CHF_2$ | 2-$OCF_2H$ | 4-F | 6-F | $CHF_2$ |
| 2-Br | 4-Br | H | $CHF_2$ | 2-F | 4-Cl | 6-Cl | $CHF_2$ |
| 2-I | 4-Br | H | $CHF_2$ | 2-Cl | 4-Cl | 6-Cl | $CHF_2$ |
| 2-Me | 4-Br | H | $CHF_2$ | 2-Br | 4-Cl | 6-Cl | $CHF_2$ |
| 2-Et | 4-Br | H | $CHF_2$ | 2-I | 4-Cl | 6-Cl | $CHF_2$ |
| 2-$CF_3$ | 4-Br | H | $CHF_2$ | 2-Me | 4-Cl | 6-Cl | $CHF_2$ |
| 2-$OCF_2H$ | 4-Br | H | $CHF_2$ | 2-Et | 4-Cl | 6-Cl | $CHF_2$ |
| 2-F | 4-I | H | $CHF_2$ | 2-$CF_3$ | 4-Cl | 6-Cl | $CHF_2$ |
| 2-Cl | 4-I | H | $CHF_2$ | 2-$OCF_2H$ | 4-Cl | 6-Cl | $CHF_2$ |
| 2-Br | 4-I | H | $CHF_2$ | 2-F | 4-Cl | 6-Br | $CHF_2$ |
| 2-I | 4-I | H | $CHF_2$ | 2-Cl | 4-Cl | 6-Br | $CHF_2$ |
| 2-Me | 4-I | H | $CHF_2$ | 2-Br | 4-Cl | 6-Br | $CHF_2$ |
| 2-Et | 4-I | H | $CHF_2$ | 2-I | 4-Cl | 6-Br | $CHF_2$ |
| 2-$CF_3$ | 4-I | H | $CHF_2$ | 2-Me | 4-Cl | 6-Br | $CHF_2$ |
| 2-F | 4-$CF_3$ | H | $CHF_2$ | 2-Et | 4-Cl | 6-Br | $CHF_2$ |
| 2-Cl | 4-$CF_3$ | H | $CHF_2$ | 2-$CF_3$ | 4-Cl | 6-Br | $CHF_2$ |
| 2-Br | 4-$CF_3$ | H | $CHF_2$ | 2-$OCF_2H$ | 4-Cl | 6-Br | $CHF_2$ |
| 2-I | 4-$CF_3$ | H | $CHF_2$ | 2-F | 4-Cl | 6-F | $CHF_2$ |
| 2-Me | 4-$CF_3$ | H | $CHF_2$ | 2-Cl | 4-Cl | 6-F | $CHF_2$ |
| 2-Et | 4-$CF_3$ | H | $CHF_2$ | 2-Br | 4-Cl | 6-F | $CHF_2$ |
| 2-$CF_3$ | 4-$CF_3$ | H | $CHF_2$ | 2-L | 4-Cl | 6-F | $CHF_2$ |
| 2-F | 4-CN | H | $CHF_2$ | 2-Me | 4-Cl | 6-F | $CHF_2$ |
| 2-Cl | 4-CN | H | $CHF_2$ | 2-Et | 4-Cl | 6-F | $CHF_2$ |
| 2-Br | 4-CN | H | $CHF_2$ | 2-$CF_3$ | 4-Cl | 6-F | $CHF_2$ |
| 2-I | 4-CN | H | $CHF_2$ | 2-$OCF_2H$ | 4-Cl | 6-F | $CHF_2$ |
| 2-Me | 4-CN | H | $CHF_2$ | 2-F | 4-Br | 6-Cl | $CHF_2$ |
| 2-Et | 4-CN | H | 4-$CF_3$ | 2-Cl | 4-Br | 6-Cl | $CHF_2$ |
| 2-$CF_3$ | 4-CN | H | $CHF_2$ | 2-Br | 4-Br | 6-Cl | $CHF_2$ |
| 2-F | H | 6-Cl | $CHF_2$ | 2-I | 4-Br | 6-Cl | $CHF_2$ |
| 2-Cl | H | 6-Cl | $CHF_2$ | 2-Me | 4-Br | 6-Cl | $CHF_2$ |
| 2-Br | H | 6-Cl | $CHF_2$ | 2-Et | 4-Br | 6-Cl | $CHF_2$ |
| 2-I | H | 6-Cl | $CHF_2$ | 2-$CF_3$ | 4-Br | 6-Cl | $CHF_2$ |
| 2-Me | H | 6-Cl | $CHF_2$ | 2-$OCF_2H$ | 4-Br | 6-Cl | $CHF_2$ |
| 2-Et | H | 6-Cl | $CHF_2$ | 2-F | 4-Br | 6-Br | $CHF_2$ |
| 2-$CF_3$ | H | 6-Cl | $CHF_2$ | 2-Cl | 4-Br | 6-Br | $CHF_2$ |
| 2-$OCF_2H$ | H | 6-Cl | $CHF_2$ | 2-Br | 4-Br | 6-Br | $CHF_2$ |

TABLE 5-continued

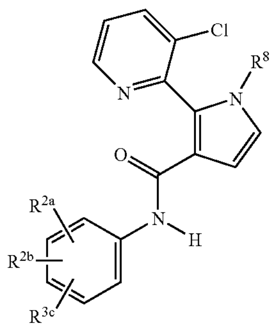

| $R^{2a}$ | $R^{2b}$ | $R^{2c}$ | $R^8$ | $R^{2a}$ | $R^{2b}$ | $R^{2c}$ | $R^8$ |
|---|---|---|---|---|---|---|---|
| 2-F | H | 6-Br | $CHF_2$ | 2-I | 4-Br | 6-Br | $CHF_2$ |
| 2-Cl | H | 6-Br | $CHF_2$ | 2-Me | 4-Br | 6-Br | $CHF_2$ |
| 2-Br | H | 6-Br | $CHF_2$ | 2-Et | 4-Br | 6-Br | $CHF_2$ |
| 2-I | H | 6-Br | $CHF_2$ | 2-$CF_3$ | 4-Br | 6-Br | $CHF_2$ |
| 2-Me | H | 6-Br | $CHF_2$ | 2-$OCF_2H$ | 4-Br | 6-Br | $CHF_2$ |
| 2-Et | H | 6-Br | $CHF_2$ | 2-F | 4-Br | 6-F | $CHF_2$ |
| 2-$CF_3$ | H | 6-Br | $CHF_2$ | 2-Cl | 4-Br | 6-F | $CHF_2$ |
| 2-$OCF_2H$ | H | 6-Br | $CHF_2$ | 2-Br | 4-Br | 6-F | $CHF_2$ |
| 2-F | H | 6-F | $CHF_2$ | 2-I | 4-Br | 6-F | $CHF_2$ |
| 2-Cl | H | 6-F | $CHF_2$ | 2-Me | 4-Br | 6-F | $CHF_2$ |
| 2-Br | H | 6-F | $CHF_2$ | 2-Et | 4-Br | 6-F | $CHF_2$ |
| 2-I | H | 6-F | $CHF_2$ | 2-$CF_3$ | 4-Br | 6-F | $CHF_2$ |
| 2-Me | H | 6-F | $CHF_2$ | 2-$OCF_2H$ | 4-Br | 6-F | $CHF_2$ |
| 2-Et | H | 6-F | $CHF_2$ | | | | |

TABLE 6

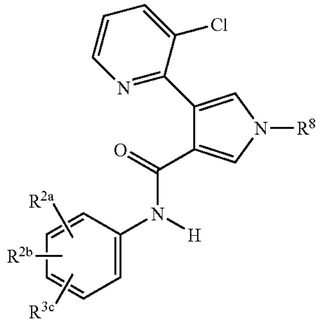

| $R^{2a}$ | $R^{2b}$ | $R^{2c}$ | $R^8$ | $R^{2a}$ | $R^{2b}$ | $R^{2c}$ | $R^8$ |
|---|---|---|---|---|---|---|---|
| H | H | H | Me | H | H | H | $OCH_2CF_3$ |
| 2-F | H | H | Me | 2-F | H | H | $OCH_2CF_3$ |
| 2-Cl | H | H | Me | 2-Cl | H | H | $OCH_2CF_3$ |
| 2-Br | H | H | Me | 2-Br | H | H | $OCH_2CF_3$ |
| 2-I | H | H | Me | 2-I | H | H | $OCH_2CF_3$ |
| 2-Me | H | H | Me | 2-Me | H | H | $OCH_2CF_3$ |
| 2-Et | H | H | Me | 2-Et | H | H | $OCH_2CF_3$ |
| 2-$CF_3$ | H | H | Me | 2-$CF_3$ | H | H | $OCH_2CF_3$ |
| 2-$OCF_2H$ | H | H | Me | 2-$OCF_2H$ | H | H | $OCH_2CF_3$ |
| 2-F | 4-F | H | Me | 2-F | 4-F | H | $OCH_2CF_3$ |
| 2-Cl | 4-F | H | Me | 2-Cl | 4-F | H | $OCH_2CF_3$ |
| 2-Br | 4-F | H | Me | 2-Br | 4-F | H | $OCH_2CF_3$ |
| 2-I | 4-F | H | Me | 2-I | 4-F | H | $OCH_2CF_3$ |
| 2-Me | 4-F | H | Me | 2-Me | 4-F | H | $OCH_2CF_3$ |
| 2-Et | 4-F | H | Me | 2-Et | 4-F | H | $OCH_2CF_3$ |
| 2-$CF_3$ | 4-F | H | Me | 2-$CF_3$ | 4-F | H | $OCH_2CF_3$ |
| 2-$OCF_2H$ | 4-F | H | Me | 2-$OCF_2H$ | 4-F | H | $OCH_2CF_3$ |
| 2-F | 4-Cl | H | Me | 2-F | 4-Cl | H | $OCH_2CF_3$ |
| 2-Cl | 4-Cl | H | Me | 2-Cl | 4-Cl | H | $OCH_2CF_3$ |
| 2-Br | 4-Cl | H | Me | 2-Br | 4-Cl | H | $OCH_2CF_3$ |
| 2-I | 4-Cl | H | Me | 2-I | 4-Cl | H | $OCH_2CF_3$ |
| 2-Me | 4-Cl | H | Me | 2-Me | 4-Cl | H | $OCH_2CF_3$ |
| 2-Et | 4-Cl | H | Me | 2-Et | 4-Cl | H | $OCH_2CF_3$ |

TABLE 6-continued

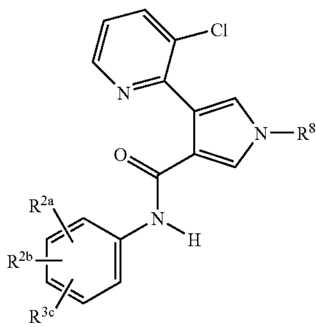

| $R^{2a}$ | $R^{2b}$ | $R^{2c}$ | $R^8$ | $R^{2a}$ | $R^{2b}$ | $R^{2c}$ | $R^8$ |
|---|---|---|---|---|---|---|---|
| 2-$CF_3$ | 4-Cl | H | Me | 2-$CF_3$ | 4-Cl | H | $OCH_2CF_3$ |
| 2-$OCF_2H$ | 4-Cl | H | Me | 2-$OCF_2H$ | 4-Cl | H | $OCH_2CF_3$ |
| 2-F | 4-Br | H | Me | 2-F | 4-Br | H | $OCH_2CF_3$ |
| 2-Cl | 4-Br | H | Me | 2-Cl | 4-Br | H | $OCH_2CF_3$ |
| 2-Br | 4-Br | H | Me | 2-Br | 4-Br | H | $OCH_2CF_3$ |
| 2-I | 4-Br | H | Me | 2-I | 4-Br | H | $OCH_2CF_3$ |
| 2-Me | 4-Br | H | Me | 2-Me | 4-Br | H | $OCH_2CF_3$ |
| 2-Et | 4-Br | H | Me | 2-Et | 4-Br | H | $OCH_2CF_3$ |
| 2-$CF_3$ | 4-Br | H | Me | 2-$CF_3$ | 4-Br | H | $OCH_2CF_3$ |
| 2-$OCF_2H$ | 4-Br | H | Me | 2-$OCF_2H$ | 4-Br | H | $OCH_2CF_3$ |
| 2-F | 4-I | H | Me | 2-F | 4-I | H | $OCH_2CF_3$ |
| 2-Cl | 4-I | H | Me | 2-Cl | 4-I | H | $OCH_2CF_3$ |
| 2-Br | 4-I | H | Me | 2-Br | 4-I | H | $OCH_2CF_3$ |
| 2-I | 4-I | H | Me | 2-I | 4-I | H | $OCH_2CF_3$ |
| 2-Me | 4-I | H | Me | 2-Me | 4-I | H | $OCH_2CF_3$ |
| 2-Et | 4-I | H | Me | 2-Et | 4-I | H | $OCH_2CF_3$ |
| 2-$CF_3$ | 4-I | H | Me | 2-$CF_3$ | 4-I | H | $OCH_2CF_3$ |
| 2-F | 4-$CF_3$ | H | Me | 2-F | 4-$CF_3$ | H | $OCH_2CF_3$ |
| 2-Cl | 4-$CF_3$ | H | Me | 2-Cl | 4-$CF_3$ | H | $OCH_2CF_3$ |
| 2-Br | 4-$CF_3$ | H | Me | 2-Br | 4-$CF_3$ | H | $OCH_2CF_3$ |
| 2-I | 4-$CF_3$ | H | Me | 2-I | 4-$CF_3$ | H | $OCH_2CF_3$ |
| 2-Me | 4-$CF_3$ | H | Me | 2-Me | 4-$CF_3$ | H | $OCH_2CF_3$ |
| 2-Et | 4-$CF_3$ | H | Me | 2-Et | 4-$CF_3$ | H | $OCH_2CF_3$ |
| 2-$CF_3$ | 4-$CF_3$ | H | Me | 2-$CF_3$ | 4-$CF_3$ | H | $OCH_2CF_3$ |
| 2-F | 4-CN | H | Me | 2-F | 4-CN | H | $OCH_2CF_3$ |
| 2-Cl | 4-CN | H | Me | 2-Cl | 4-CN | H | $OCH_2CF_3$ |
| 2-Br | 4-CN | H | Me | 2-Br | 4-CN | H | $OCH_2CF_3$ |
| 2-I | 4-CN | H | Me | 2-I | 4-CN | H | $OCH_2CF_3$ |
| 2-Me | 4-CN | H | Me | 2-Me | 4-CN | H | $OCH_2CF_3$ |
| 2-Et | 4-CN | H | Me | 2-Et | 4-CN | H | $OCH_2CF_3$ |
| 2-$CF_3$ | 4-CN | H | Me | 2-$CF_3$ | 4-CN | H | $OCH_2CF_3$ |
| 2-F | H | 6-Cl | Me | 2-F | H | 6-Cl | $OCH_2CF_3$ |
| 2-Cl | H | 6-Cl | Me | 2-Cl | H | 6-Cl | $OCH_2CF_3$ |
| 2-Br | H | 6-Cl | Me | 2-Br | H | 6-Cl | $OCH_2CF_3$ |
| 2-I | H | 6-Cl | Me | 2-I | H | 6-Cl | $OCH_2CF_3$ |
| 2-Me | H | 6-Cl | Me | 2-Me | H | 6-Cl | $OCH_2CF_3$ |
| 2-Et | H | 6-Cl | Me | 2-Et | H | 6-Cl | $OCH_2CF_3$ |
| 2-$CF_3$ | H | 6-Cl | Me | 2-$CF_3$ | H | 6-Cl | $OCH_2CF_3$ |
| 2-$OCF_2H$ | H | 6-Cl | Me | 2-$OCF_2H$ | H | 6-Cl | $OCH_2CF_3$ |
| 2-F | H | 6-Br | Me | 2-F | H | 6-Br | $OCH_2CF_3$ |
| 2-Cl | H | 6-Br | Me | 2-Cl | H | 6-Br | $OCH_2CF_3$ |
| 2-Br | H | 6-Br | Me | 2-Br | H | 6-Br | $OCH_2CF_3$ |
| 2-I | H | 6-Br | Me | 2-I | H | 6-Br | $OCH_2CF_3$ |
| 2-Me | H | 6-Br | Me | 2-Me | H | 6-Br | $OCH_2CF_3$ |
| 2-Et | H | 6-Br | Me | 2-Et | H | 6-Br | $OCH_2CF_3$ |
| 2-$CF_3$ | H | 6-Br | Me | 2-$CF_3$ | H | 6-Br | $OCH_2CF_3$ |
| 2-$OCF_2H$ | H | 6-Br | Me | 2-$OCF_2H$ | H | 6-Br | $OCH_2CF_3$ |
| 2-F | H | 6-F | Me | 2-F | H | 6-F | $OCH_2CF_3$ |
| 2-Cl | H | 6-F | Me | 2-Cl | H | 6-F | $OCH_2CF_3$ |
| 2-Br | H | 6-F | Me | 2-Br | H | 6-F | $OCH_2CF_3$ |
| 2-I | H | 6-F | Me | 2-I | H | 6-F | $OCH_2CF_3$ |
| 2-Me | H | 6-F | Me | 2-Me | H | 6-F | $OCH_2CF_3$ |
| 2-Et | H | 6-F | Me | 2-Et | H | 6-F | $OCH_2CF_3$ |
| 2-$CF_3$ | H | 6-F | Me | 2-$CF_3$ | H | 6-F | $OCH_2CF_3$ |
| 2-$OCF_2H$ | H | 6-F | Me | 2-$OCF_2H$ | H | 6-F | $OCH_2CF_3$ |
| 2-F | 4-F | 6-Cl | Me | 2-F | 4-F | 6-Cl | $OCH_2CF_3$ |
| 2-Cl | 4-F | 6-Cl | Me | 2-Cl | 4-F | 6-Cl | $OCH_2CF_3$ |
| 2-Br | 4-F | 6-Cl | Me | 2-Br | 4-F | 6-Cl | $OCH_2CF_3$ |
| 2-I | 4-F | 6-Cl | Me | 2-I | 4-F | 6-Cl | $OCH_2CF_3$ |
| 2-Me | 4-F | 6-Cl | Me | 2-Me | 4-F | 6-Cl | $OCH_2CF_3$ |

TABLE 6-continued

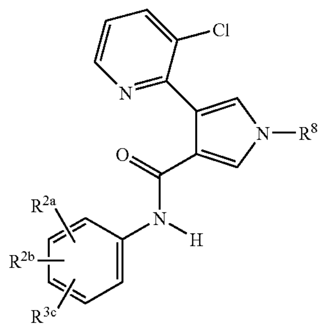

| $R^{2a}$ | $R^{2b}$ | $R^{2c}$ | $R^8$ | $R^{2a}$ | $R^{2b}$ | $R^{2c}$ | $R^8$ |
|---|---|---|---|---|---|---|---|
| 2-Et | 4-F | 6-Cl | Me | 2-Et | 4-F | 6-Cl | $OCH_2CF_3$ |
| 2-$CF_3$ | 4-F | 6-Cl | Me | 2-$CF_3$ | 4-F | 6-Cl | $OCH_2CF_3$ |
| 2-$OCF_2H$ | 4-F | 6-Cl | Me | 2-$OCF_2H$ | 4-F | 6-Cl | $OCH_2CF_3$ |
| 2-F | 4-F | 6-Br | Me | 2-F | 4-F | 6-Br | $OCH_2CF_3$ |
| 2-Cl | 4-F | 6-Br | Me | 2-Cl | 4-F | 6-Br | $OCH_2CF_3$ |
| 2-Br | 4-F | 6-Br | Me | 2-Br | 4-F | 6-Br | $OCH_2CF_3$ |
| 2-I | 4-F | 6-Br | Me | 2-I | 4-F | 6-Br | $OCH_2CF_3$ |
| 2-Me | 4-F | 6-Br | Me | 2-Me | 4-F | 6-Br | $OCH_2CF_3$ |
| 2-Et | 4-F | 6-Br | Me | 2-Et | 4-F | 6-Br | $OCH_2CF_3$ |
| 2-$CF_3$ | 4-F | 6-Br | Me | 2-$CF_3$ | 4-F | 6-Br | $OCH_2CF_3$ |
| 2-$OCF_2H$ | 4-F | 6-Br | Me | 2-$OCF_2H$ | 4-F | 6-Br | $OCH_2CF_3$ |
| 2-F | 4-F | 6-F | Me | 2-F | 4-F | 6-F | $OCH_2CF_3$ |
| 2-Cl | 4-F | 6-F | Me | 2-Cl | 4-F | 6-F | $OCH_2CF_3$ |
| 2-Br | 4-F | 6-F | Me | 2-Br | 4-F | 6-F | $OCH_2CF_3$ |
| 2-I | 4-F | 6-F | Me | 2-I | 4-F | 6-F | $OCH_2CF_3$ |
| 2-Me | 4-F | 6-F | Me | 2-Me | 4-F | 6-F | $OCH_2CF_3$ |
| 2-Et | 4-F | 6-F | Me | 2-Et | 4-F | 6-F | $OCH_2CF_3$ |
| 2-$CF_3$ | 4-F | 6-F | Me | 2-$CF_3$ | 4-F | 6-F | $OCH_2CF_3$ |
| 2-$OCF_2H$ | 4-F | 6-F | Me | 2-$OCF_2H$ | 4-F | 6-F | $OCH_2CF_3$ |
| 2-F | 4-Cl | 6-Cl | Me | 2-F | 4-Cl | 6-Cl | $OCH_2CF_3$ |
| 2-Cl | 4-Cl | 6-Cl | Me | 2-Cl | 4-Cl | 6-Cl | $OCH_2CF_3$ |
| 2-Br | 4-Cl | 6-Cl | Me | 2-Br | 4-Cl | 6-Cl | $OCH_2CF_3$ |
| 2-I | 4-Cl | 6-Cl | Me | 2-I | 4-Cl | 6-Cl | $OCH_2CF_3$ |
| 2-Me | 4-Cl | 6-Cl | Me | 2-Me | 4-Cl | 6-Cl | $OCH_2CF_3$ |
| 2-Et | 4-Cl | 6-Cl | Me | 2-Et | 4-Cl | 6-Cl | $OCH_2CF_3$ |
| 2-$CF_3$ | 4-Cl | 6-Cl | Me | 2-$CF_3$ | 4-Cl | 6-Cl | $OCH_2CF_3$ |
| 2-$OCF_2H$ | 4-Cl | 6-Cl | Me | 2-$OCF_2H$ | 4-Cl | 6-Cl | $OCH_2CF_3$ |
| 2-F | 4-Cl | 6-Br | Me | 2-F | 4-Cl | 6-Br | $OCH_2CF_3$ |
| 2-Cl | 4-Cl | 6-Br | Me | 2-Cl | 4-Cl | 6-Br | $OCH_2CF_3$ |
| 2-Br | 4-Cl | 6-Br | Me | 2-Br | 4-Cl | 6-Br | $OCH_2CF_3$ |
| 2-I | 4-Cl | 6-Br | Me | 2-I | 4-Cl | 6-Br | $OCH_2CF_3$ |
| 2-Me | 4-Cl | 6-Br | Me | 2-Me | 4-Cl | 6-Br | $OCH_2CF_3$ |
| 2-Et | 4-Cl | 6-Br | Me | 2-Et | 4-Cl | 6-Br | $OCH_2CF_3$ |
| 2-$CF_3$ | 4-Cl | 6-Br | Me | 2-$CF_3$ | 4-Cl | 6-Br | $OCH_2CF_3$ |
| 2-$OCF_2H$ | 4-Cl | 6-Br | Me | 2-$OCF_2H$ | 4-Cl | 6-Br | $OCH_2CF_3$ |
| 2-F | 4-Cl | 6-F | Me | 2-F | 4-Cl | 6-F | $OCH_2CF_3$ |
| 2-Cl | 4-Cl | 6-F | Me | 2-Cl | 4-Cl | 6-F | $OCH_2CF_3$ |
| 2-Br | 4-Cl | 6-F | Me | 2-Br | 4-Cl | 6-F | $OCH_2CF_3$ |
| 2-I | 4-Cl | 6-F | Me | 2-I | 4-Cl | 6-F | $OCH_2CF_3$ |
| 2-Me | 4-Cl | 6-F | Me | 2-Me | 4-Cl | 6-F | $OCH_2CF_3$ |
| 2-Et | 4-Cl | 6-F | Me | 2-Et | 4-Cl | 6-F | $OCH_2CF_3$ |
| 2-$CF_3$ | 4-Cl | 6-F | Me | 2-$CF_3$ | 4-Cl | 6-F | $OCH_2CF_3$ |
| 2-$OCF_2H$ | 4-Cl | 6-F | Me | 2-$OCF_2H$ | 4-Cl | 6-F | $OCH_2CF_3$ |
| 2-F | 4-Br | 6-Cl | Me | 2-F | 4-Br | 6-Cl | $OCH_2CF_3$ |
| 2-Cl | 4-Br | 6-Cl | Me | 2-Cl | 4-Br | 6-Cl | $OCH_2CF_3$ |
| 2-Br | 4-Br | 6-Cl | Me | 2-Br | 4-Br | 6-Cl | $OCH_2CF_3$ |
| 2-I | 4-Br | 6-Cl | Me | 2-I | 4-Br | 6-Cl | $OCH_2CF_3$ |
| 2-Me | 4-Br | 6-Cl | Me | 2-Me | 4-Br | 6-Cl | $OCH_2CF_3$ |
| 2-Et | 4-Br | 6-Cl | Me | 2-Et | 4-Br | 6-Cl | $OCH_2CF_3$ |
| 2-$CF_3$ | 4-Br | 6-Cl | Me | 2-$CF_3$ | 4-Br | 6-Cl | $OCH_2CF_3$ |
| 2-$OCF_2H$ | 4-Br | 6-Cl | Me | 2-$OCF_2H$ | 4-Br | 6-Cl | $OCH_2CF_3$ |
| 2-F | 4-Br | 6-Br | Me | 2-F | 4-Br | 6-Br | $OCH_2CF_3$ |
| 2-Cl | 4-Br | 6-Br | Me | 2-Cl | 4-Br | 6-Br | $OCH_2CF_3$ |
| 2-Br | 4-Br | 6-Br | Me | 2-Br | 4-Br | 6-Br | $OCH_2CF_3$ |
| 2-I | 4-Br | 6-Br | Me | 2-I | 4-Br | 6-Br | $OCH_2CF_3$ |
| 2-Me | 4-Br | 6-Br | Me | 2-Me | 4-Br | 6-Br | $OCH_2CF_3$ |
| 2-Et | 4-Br | 6-Br | Me | 2-Et | 4-Br | 6-Br | $OCH_2CF_3$ |
| 2-$CF_3$ | 4-Br | 6-Br | Me | 2-$CF_3$ | 4-Br | 6-Br | $OCH_2CF_3$ |
| 2-$OCF_2H$ | 4-Br | 6-Br | Me | 2-$OCF_2H$ | 4-Br | 6-Br | $OCH_2CF_3$ |
| 2-F | 4-Br | 6-F | Me | 2-F | 4-Br | 6-F | $OCH_2CF_3$ |

TABLE 6-continued

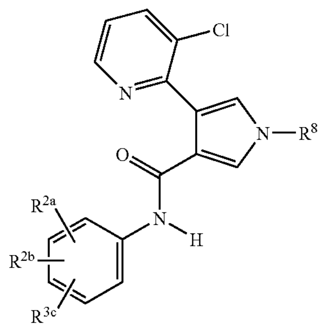

| $R^{2a}$ | $R^{2b}$ | $R^{2c}$ | $R^8$ | $R^{2a}$ | $R^{2b}$ | $R^{2c}$ | $R^8$ |
|---|---|---|---|---|---|---|---|
| 2-Cl | 4-Br | 6-F | Me | 2-Cl | 4-Br | 6-F | $OCH_2CF_3$ |
| 2-Br | 4-Br | 6-F | Me | 2-Br | 4-Br | 6-F | $OCH_2CF_3$ |
| 2-I | 4-Br | 6-F | Me | 2-I | 4-Br | 6-F | $OCH_2CF_3$ |
| 2-Me | 4-Br | 6-F | Me | 2-Me | 4-Br | 6-F | $OCH_2CF_3$ |
| 2-Et | 4-Br | 6-F | Me | 2-Et | 4-Br | 6-F | $OCH_2CF_3$ |
| 2-$CF_3$ | 4-Br | 6-F | Me | 2-$CF_3$ | 4-Br | 6-F | $OCH_2CF_3$ |
| 2-$OCF_2H$ | 4-Br | 6-F | Me | 2-$OCF_2H$ | 4-Br | 6-F | $OCH_2CF_3$ |
| 2-F | H | H | $CHF_2$ | 2-$CF_3$ | H | 6-F | $CHF_2$ |
| 2-Cl | H | H | $CHF_2$ | 2-$OCF_2H$ | H | 6-F | $CHF_2$ |
| 2-Br | H | H | $CHF_2$ | 2-F | 4-F | 6-Cl | $CHF_2$ |
| 2-I | H | H | $CHF_2$ | 2-Cl | 4-F | 6-Cl | $CHF_2$ |
| 2-Me | H | H | $CHF_2$ | 2-Br | 4-F | 6-Cl | $CHF_2$ |
| 2-Et | H | H | $CHF_2$ | 2-I | 4-F | 6-Cl | $CHF_2$ |
| 2-$CF_3$ | H | H | $CHF_2$ | 2-Me | 4-F | 6-Cl | $CHF_2$ |
| 2-$OCF_2H$ | H | H | $CHF_2$ | 2-Et | 4-F | 6-Cl | $CHF_2$ |
| 2-F | 4-F | H | $CHF_2$ | 2-$CF_3$ | 4-F | 6-Cl | $CHF_2$ |
| 2-Cl | 4-F | H | $CHF_2$ | 2-$OCF_2H$ | 4-F | 6-Cl | $CHF_2$ |
| 2-Br | 4-F | H | $CHF_2$ | 2-F | 4-F | 6-Br | $CHF_2$ |
| 2-I | 4-F | H | $CHF_2$ | 2-Cl | 4-F | 6-Br | $CHF_2$ |
| 2-Me | 4-F | H | $CHF_2$ | 2-Br | 4-F | 6-Br | $CHF_2$ |
| 2-Et | 4-F | H | $CHF_2$ | 2-I | 4-F | 6-Br | $CHF_2$ |
| 2-$CF_3$ | 4-F | H | $CHF_2$ | 2-Me | 4-F | 6-Br | $CHF_2$ |
| 2-$OCF_2H$ | 4-F | H | $CHF_2$ | 2-Et | 4-F | 6-Br | $CHF_2$ |
| 2-F | 4-Cl | H | $CHF_2$ | 2-$CF_3$ | 4-F | 6-Br | $CHF_2$ |
| 2-Cl | 4-Cl | H | $CHF_2$ | 2-$OCF_2H$ | 4-F | 6-Br | $CHF_2$ |
| 2-Br | 4-Cl | H | $CHF_2$ | 2-F | 4-F | 6-F | $CHF_2$ |
| 2-I | 4-Cl | H | $CHF_2$ | 2-Cl | 4-F | 6-F | $CHF_2$ |
| 2-Me | 4-Cl | H | $CHF_2$ | 2-Br | 4-F | 6-F | $CHF_2$ |
| 2-Et | 4-Cl | H | $CHF_2$ | 2-I | 4-F | 6-F | $CHF_2$ |
| 2-$CF_3$ | 4-Cl | H | $CHF_2$ | 2-Me | 4-F | 6-F | $CHF_2$ |
| 2-$OCF_2H$ | 4-Cl | H | $CHF_2$ | 2-Et | 4-F | 6-F | $CHF_2$ |
| 2-F | 4-Br | H | $CHF_2$ | 2-$CF_3$ | 4-F | 6-F | $CHF_2$ |
| 2-Cl | 4-Br | H | $CHF_2$ | 2-$OCF_2H$ | 4-F | 6-F | $CHF_2$ |
| 2-Br | 4-Br | H | $CHF_2$ | 2-F | 4-Cl | 6-Cl | $CHF_2$ |
| 2-I | 4-Br | H | $CHF_2$ | 2-Cl | 4-Cl | 6-Cl | $CHF_2$ |
| 2-Me | 4-Br | H | $CHF_2$ | 2-Br | 4-Cl | 6-Cl | $CHF_2$ |
| 2-Et | 4-Br | H | $CHF_2$ | 2-I | 4-Cl | 6-Cl | $CHF_2$ |
| 2-$CF_3$ | 4-Br | H | $CHF_2$ | 2-Me | 4-Cl | 6-Cl | $CHF_2$ |
| 2-$OCF_2H$ | 4-Br | H | $CHF_2$ | 2-Et | 4-Cl | 6-Cl | $CHF_2$ |
| 2-F | 4-I | H | $CHF_2$ | 2-$CF_3$ | 4-Cl | 6-Cl | $CHF_2$ |
| 2-Cl | 4-I | H | $CHF_2$ | 2-$OCF_2H$ | 4-Cl | 6-Cl | $CHF_2$ |
| 2-Br | 4-I | H | $CHF_2$ | 2-F | 4-Cl | 6-Br | $CHF_2$ |
| 2-I | 4-I | H | $CHF_2$ | 2-Cl | 4-Cl | 6-Br | $CHF_2$ |
| 2-Me | 4-I | H | $CHF_2$ | 2-Br | 4-Cl | 6-Br | $CHF_2$ |
| 2-Et | 4-I | H | $CHF_2$ | 2-I | 4-Cl | 6-Br | $CHF_2$ |
| 2-$CF_3$ | 4-I | H | $CHF_2$ | 2-Me | 4-Cl | 6-Br | $CHF_2$ |
| 2-F | 4-$CF_3$ | H | $CHF_2$ | 2-Et | 4-Cl | 6-Br | $CHF_2$ |
| 2-Cl | 4-$CF_3$ | H | $CHF_2$ | 2-$CF_3$ | 4-Cl | 6-Br | $CHF_2$ |
| 2-Br | 4-$CF_3$ | H | $CHF_2$ | 2-$OCF_2H$ | 4-Cl | 6-Br | $CHF_2$ |
| 2-I | 4-$CF_3$ | H | $CHF_2$ | 2-F | 4-Cl | 6-F | $CHF_2$ |
| 2-Me | 4-$CF_3$ | H | $CHF_2$ | 2-Cl | 4-Cl | 6-F | $CHF_2$ |
| 2-Et | 4-$CF_3$ | H | $CHF_2$ | 2-Br | 4-Cl | 6-F | $CHF_2$ |
| 2-$CF_3$ | 4-$CF_3$ | H | $CHF_2$ | 2-I | 4-Cl | 6-F | $CHF_2$ |
| 2-F | 4-CN | H | $CHF_2$ | 2-Me | 4-Cl | 6-F | $CHF_2$ |
| 2-Cl | 4-CN | H | $CHF_2$ | 2-Et | 4-Cl | 6-F | $CHF_2$ |
| 2-Br | 4-CN | H | $CHF_2$ | 2-$CF_3$ | 4-Cl | 6-F | $CHF_2$ |
| 2-I | 4-CN | H | $CHF_2$ | 2-$OCF_2H$ | 4-Cl | 6-F | $CHF_2$ |
| 2-Me | 4-CN | H | $CHF_2$ | 2-F | 4-Br | 6-Cl | $CHF_2$ |
| 2-Et | 4-CN | H | $CHF_2$ | 2-Cl | 4-Br | 6-Cl | $CHF_2$ |
| 2-$CF_3$ | 4-CN | H | $CHF_2$ | 2-Br | 4-Br | 6-Cl | $CHF_2$ |

TABLE 6-continued

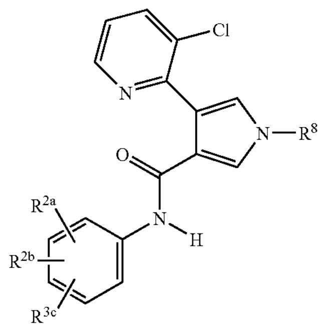

| $R^{2a}$ | $R^{2b}$ | $R^{2c}$ | $R^8$ | $R^{2a}$ | $R^{2b}$ | $R^{2c}$ | $R^8$ |
|---|---|---|---|---|---|---|---|
| 2-F | H | 6-Cl | $CHF_2$ | 2-I | 4-Br | 6-Cl | $CHF_2$ |
| 2-Cl | H | 6-Cl | $CHF_2$ | 2-Me | 4-Br | 6-Cl | $CHF_2$ |
| 2-Br | H | 6-Cl | $CHF_2$ | 2-Et | 4-Br | 6-Cl | $CHF_2$ |
| 2-I | H | 6-Cl | $CHF_2$ | 2-$CF_3$ | 4-Br | 6-Cl | $CHF_2$ |
| 2-Me | H | 6-Cl | $CHF_2$ | 2-$OCF_2H$ | 4-Br | 6-Cl | $CHF_2$ |
| 2-Et | H | 6-Cl | $CHF_2$ | 2-F | 4-Br | 6-Br | $CHF_2$ |
| 2-$CF_3$ | H | 6-Cl | $CHF_2$ | 2-Cl | 4-Br | 6-Br | $CHF_2$ |
| 2-$OCF_2H$ | H | 6-Cl | $CHF_2$ | 2-Br | 4-Br | 6-Br | $CHF_2$ |
| 2-F | H | 6-Br | $CHF_2$ | 2-I | 4-Br | 6-Br | $CHF_2$ |
| 2-Cl | H | 6-Br | $CHF_2$ | 2-Me | 4-Br | 6-Br | $CHF_2$ |
| 2-Br | H | 6-Br | $CHF_2$ | 2-Et | 4-Br | 6-Br | $CHF_2$ |
| 2-I | H | 6-Br | $CHF_2$ | 2-$CF_3$ | 4-Br | 6-Br | $CHF_2$ |
| 2-Me | H | 6-Br | $CHF_2$ | 2-$OCF_2H$ | 4-Br | 6-Br | $CHF_2$ |
| 2-Et | H | 6-Br | $CHF_2$ | 2-F | 4-Br | 6-F | $CUF_2$ |
| 2-$CF_3$ | H | 6-Br | $CHF_2$ | 2-Cl | 4-Br | 6-F | $CHF_2$ |
| 2-$OCF_2H$ | H | 6-Br | $CHF_2$ | 2-Br | 4-Br | 6-F | $CHF_2$ |
| 2-F | H | 6-F | $CHF_2$ | 2-I | 4-Br | 6-F | $CHF_2$ |
| 2-Cl | H | 6-F | $CHF_2$ | 2-Me | 4-Br | 6-F | $CHF_2$ |
| 2-Br | H | 6-F | $CHF_2$ | 2-Et | 4-Br | 6-F | $CHF_2$ |
| 2-I | H | 6-F | $CHF_2$ | 2-$CF_3$ | 4-Br | 6-F | $CHF_2$ |
| 2-Me | H | 6-F | $CHF_2$ | 2-$OCF_2H$ | 4-Br | 6-F | $CHF_2$ |
| 2-Et | H | 6-F | $CHF_2$ | | | | |

TABLE 7

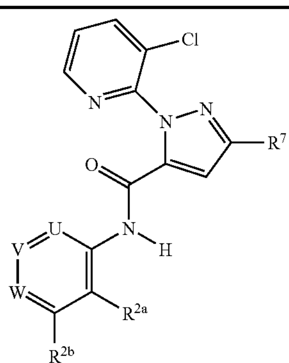

| U | V | W | $R^{2a}$ | $R^{2b}$ | $R^7$ |
|---|---|---|---|---|---|
| N | CH | CH | H | H | Cl |
| N | CH | CH | F | H | Cl |
| N | CH | CH | Cl | H | Cl |
| N | CH | CH | Br | H | Cl |
| N | CH | CH | Me | H | Cl |
| N | CH | CH | $CF_3$ | H | Cl |
| N | CH | C—Cl | Cl | H | Cl |
| N | CH | C—$CF_3$ | Cl | H | Cl |
| N | CH | CH | H | H | Br |
| N | CH | CH | F | H | Br |
| N | CH | CH | Cl | H | Br |
| N | CH | CH | Br | H | Br |
| N | CH | CH | Me | H | Br |

TABLE 7-continued

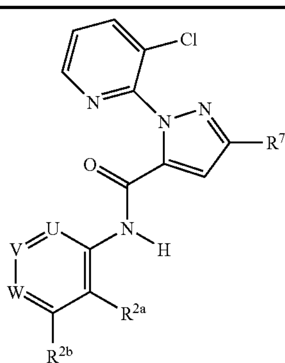

| U | V | W | $R^{2a}$ | $R^{2b}$ | $R^7$ |
|---|---|---|---|---|---|
| N | CH | CH | $CF_3$ | H | Br |
| N | CH | C—Cl | Cl | H | Br |
| N | CH | C—$CF_3$ | Cl | H | Br |
| N | CH | CH | H | H | $CF_3$ |
| N | CH | CH | F | H | $CF_3$ |
| N | CH | CH | Cl | H | $CF_3$ |
| N | CH | CH | Br | H | $CF_3$ |
| N | CH | CH | Me | H | $CF_3$ |
| N | CH | CH | CE3 | H | $CF_3$ |
| N | CH | C—Cl | Cl | H | $CF_3$ |
| N | CH | C—$CF_3$ | Cl | H | $CF_3$ |
| N | CH | CH | H | H | $OCH_2CF_3$ |
| N | CH | CH | F | H | $OCH_2CF_3$ |

TABLE 7-continued

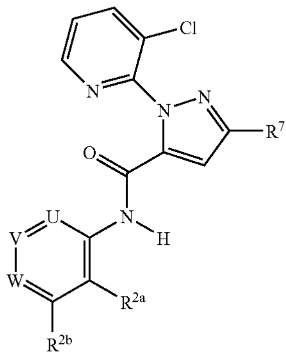

| U | V | W | $R^{2a}$ | $R^{2b}$ | $R^7$ |
|---|---|---|---|---|---|
| N | CH | CH | Cl | H | $OCH_2CF_3$ |
| N | CH | CH | Br | H | $OCH_2CF_3$ |
| N | CH | CH | Me | H | $OCH_2CF_3$ |
| N | CH | CH | $CF_3$ | H | $OCH_2CF_3$ |
| N | CH | C—Cl | Cl | H | $OCH_2CF_3$ |
| N | CH | C—$CF_3$ | Cl | H | $OCH_2CF_3$ |
| C—Cl | N | CH | H | H | Cl |
| C—Cl | N | C—Cl | H | H | Cl |
| C-Me | N | CH | H | H | Cl |
| CH | N | CH | Me | H | Cl |
| CH | N | CH | Cl | H | Cl |
| C—Cl | N | CH | H | H | Br |
| C—Cl | N | C—Cl | H | H | Br |
| C-Me | N | CH | H | H | Br |
| CH | N | CH | Me | H | Br |
| CH | N | CH | Cl | H | Br |
| C—Cl | N | CH | H | H | $CF_3$ |
| C—Cl | N | C—Cl | H | H | $CF_3$ |
| C-Me | N | CH | H | H | $CF_3$ |
| CH | N | CH | Me | H | $CF_3$ |
| CH | N | CH | Cl | H | $CF_3$ |
| C—Cl | N | CH | H | H | $OCH_2CF_3$ |
| C—Cl | N | C—Cl | H | H | $OCH_2CF_3$ |
| C-Me | N | CH | H | H | $OCH_2CF_3$ |
| CH | N | CH | Me | H | $OCH_2CF_3$ |
| CH | N | CH | Cl | H | $0OH_2CF_3$ |
| C—Cl | CH | N | H | H | Cl |
| C—Cl | CH | N | Cl | H | Cl |
| C-Me | CH | N | H | H | Cl |
| CH | C—Cl | N | Cl | H | Cl |
| CH | C—$CF_3$ | N | $CF_3$ | H | Cl |
| C—F | C—F | N | F | F | Cl |
| CH | CH | N | H | H | Cl |
| C—Cl | CH | N | H | H | Br |
| C—Cl | CH | N | Cl | H | Br |
| C-Me | CH | N | H | H | Br |
| CH | C—Cl | N | Cl | H | Br |
| CH | C—$CF_3$ | N | $CF_3$ | H | Br |
| C—F | C—F | N | F | F | Br |
| CH | CH | N | H | H | Br |
| C—Cl | CH | N | H | H | $CF_3$ |
| C—Cl | CH | N | Cl | H | $CF_3$ |
| C-Me | CH | N | H | H | $CF_3$ |
| CH | C—Cl | N | Cl | H | $CF_3$ |
| CH | C—$CF_3$ | N | $CF_3$ | H | $CF_3$ |
| C—F | C—F | N | F | F | $CF_3$ |
| CH | CH | N | H | H | $CF_3$ |
| C—Cl | CH | N | H | H | $OCH_2CF_3$ |
| C—Cl | CH | N | Cl | H | $OCH_2CF_3$ |
| C-Me | CH | N | H | H | $OCH_2CF_3$ |
| CH | C—Cl | N | Cl | H | $OCH_2CF_3$ |
| CH | C—$CF_3$ | N | $CF_3$ | H | $OCH_2CF_3$ |
| C—F | C—F | N | F | F | $OCH_2CF_3$ |
| CH | CH | N | H | H | $OCH_2CF_3$ |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges that add up to 100 percent by weight.

| | Weight Percent | | |
|---|---|---|---|
| | Active Ingredient | Diluent | Surfactant |
| Water-Dispersible and Water-soluble Granules, Tablets and Powders. | 5-90 | 0-94 | 1-15 |
| Suspensions, Emulsions, Solutions (including Emulsifiable Concentrates) | 5-50 | 40-95 | 0-15 |
| Dusts | 1-25 | 70-99 | 0-5 |
| Granules and Pellets | 0.01-99 | 5-99.99 | 0-15 |
| High Strength Compositions | 90-99 | 0-10 | 0-2 |

Typical solid diluents are described in Watkins, et al., *Handbook of Insecticide Dust Diluents and Carriers,* 2nd Ed., Dorland Books, Caldwell, N.J. Typical liquid diluents are described in Marsden, *Solvents Guide,* 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylenelpolyoxypropylene block copolymers. Solid diluents include, for example, clays such as bentonite, montnorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook,* 4th Ed., McGraw-Hill, New York, 1963, pages 8-57 and following, and PCT Publication WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 14; Klingman, *Weed Control as a Science*, John Wiley and Sons, Inc., New York, 1961, pp 81-96; and Hance et al., *Weed Control Handbook,* 8th Ed., Blackwell Scientific Publications, Oxford, 1989.

In the following Examples, all percentages are by weight and all formulations are prepared in conventional ways. Compound numbers refer to compounds in Index Table A.

Example A

| Wettable Powder | |
|---|---|
| Compound 1 | 65.0% |
| dodecylphenol polyethylene-glycol ether | 2.0% |
| sodium ligninsulfonate | 4.0% |
| sodium silicoaluminate | 6.0% |
| montmorillonite (calcined) | 23.0%. |

Example B

| Granule | |
|---|---|
| Compound 1 | 10.0% |
| attapulgite granules (low volatile matter, 0.71/0.30 mm; U.S.S. No. 25-50 sieves) | 90.0%. |

Example C

| Extruded Pellet | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example D

| Emulsifiable Concentrate | |
|---|---|
| Compound 1 | 20.0% |
| blend of oil soluble sulfonates and polyoxyethylene ethers | 10.0% |
| isophorone | 70.0%. |

Example E

| Granule | |
|---|---|
| Compound 1 | 0.5% |
| cellulose | 2.5% |
| lactose | 4.0% |
| cornmeal | 93.0%. |

Compounds of this invention are characterized by favorable metabolic and/or soil residual patterns and exhibit activity controlling a spectrum of agronomic and non-agronomic invertebrate pests. (In the context of this disclosure "invertebrate pest control" means inhibition of invertebrate pest development (including mortality) that causes significant reduction in feeding or other injury or damage caused by the pest; related expressions are defined analogously.) As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" includes all of the helminths, such as: roundworms, heartworms, and phytophagous nematodes (Nematoda), flukes (Tematoda), Acanthocephala, and tapeworms (Cestoda). Those skilled in the art will recognize that not all compounds are equally effective against all pests. Compounds of this invention display activity against economically important agronomic and nonagronomic pests. The term "agronomic" refers to the production of field crops such as for food and fiber and includes the growth of cereal crops (e.g., wheat, oats, barley, rye, rice, maize), soybeans, vegetable crops (e.g., lettuce, cabbage, tomatoes, beans), potatoes, sweet potatoes, grapes, cotton, and tree fruits (e.g., pome fruits, stone fruits and citrus fruits). The term "nonagronomic" refers to other horticultural (e.g., forest, greenhouse, nursery or ornamental plants not grown in a field), public (human) and animal health, domestic and commercial structure, household, and stored product applications or pests. For reason of invertebrate pest control spectrum and economic importance, protection (from damage or injury caused by invertebrate pests) of agronomic crops of cotton, maize, soybeans, rice, vegetable crops, potato, sweet potato, grapes and tree fruit by controlling invertebrate pests are preferred embodiments of the invention. Agronomic or nonagronomic pests include larvae of the order Lepidoptera, such as armyworms, cutworms, loopers, and heliothines in the family Noctuidae (e.g., fall armyworm (*Spodoptera fugiperda* J. E. Smith), beet armyworm (*Spodoptera exigua* Hübner), black cutworm (*Agrotis ipsilon* Hufnagel), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworm (*Herpetogramma licarsisalis* Walker)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus)); nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)); foliar feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scaribaeidae (e.g., Japanese beetle (*Popillia japonica* Newman) and European chafer (*Rhizotrogus majalis* Razoumowsky)); carpet beetles from the family Dermestidae; wireworms from the family Elateridae; bark beetles from the family Scolytidae and flour beetles from the family Tenebrionidae. In addition agronomic and nonagronomic pests include: adults and larvae of the order Dermaptera including earwigs from the family Forficulidae (e.g., European earwig (*Forficula auricularia* Linnaeus), black earwig (*Chelisoches morio* Fabricius)); adults and nymphs of the orders Hemiptera and Homoptera such as, plant bugs from the family Miridae, cicadas from the family Cicadidae, leafhoppers (e.g. *Empoasca* spp.) from the family Cicadellidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, cinch bugs (e.g., *Blissus* spp.) and other seed bugs from the family Lygaeidae, spittlebugs from the family Cercopidae squash bugs from the family Coreidae, and red bugs and cotton stainers from the family Pyrrhocoridae. Also included are adults and larvae of the order Acari (mites) such as spider mites and red mites in the family Tetranychidae (e.g., European red mite (*Panonychus ulmi* Koch), two spotted spider mite (*Teiranychus urticae* Koch), McDaniel mite (*Tetranychus mcdanieli* McGregor)), flat mites in the family Tenuipalpidae (e.g., citrus flat mite (*Brevipalpus lewisi* McGregor)), rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus) and scab and itch mites in the families Psoroptidae, Pyemotidae, and Sarcoptidae; adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* Linnaeus), house cricket (*Acheta domesticus* Linnaeus), mole crickets (*Giyllotalpa* spp.)); adults and immatures of the order Diptera including leafminers, midges, fruit flies (Tephritidae), frit flies (e.g., *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; adults and immatures of the order Thysanoptera including onion thrips (*Thrips tabaci* Lindeman) and other foliar feeding thrips; insect pests of the order Hymenoptera including ants (e.g., red carpenter ant (*Camponotus ferrugineus* Fabricius), black carpenter ant (*Camponotus pennsylvanicus* De Geer), Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster), odorous house ant (*Tapinoma sessile* Say)), bees (including carpenter bees), hornets, yellow jackets and wasps; insect pests of the order Isoptera including the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder) and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus humanus* Linnaeus), chicken body louse (*Menacanthus stramineus* Nitszch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus). Compounds of the present invention also have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Compounds of the invention show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other Archips species, *Chilo suppressalis* Walker (rice stem borer), *Cnaphalocrosis medinalis* Guenee (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)). Compounds of the invention also have commercially significant activity on members from the order Homoptera including: *Acyrthisiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosipum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phlylloxera devastatrix* Pergande (pecan phylloxera); *Bemisia tabaci* Gennadius (tobacco whitefly, sweetpotato whitefly), *Bemisia argentifoli* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stål (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), Typhlocybapomaria McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla). These compounds also have activity on members from the order Hemiptera including: *Acrosternum hilare* Say (green stink bug), *Anasa tristis* De Geer (squash bug), *Blissus leucopterus leucopterus* Say (chinch bug), *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Frankliniella occidentalis* Pergande (western flower thrip), *Scirthothrips citri* Moulton (citrus thrip), *Sericothrips variabilis* Beach (soybean thrip), and *Thrips tabaci* Lindeman (onion thrip); and the order Coleoptera (e.g., *Leptinotarsa decemlineata* Say (Colorado potato beetle), *Epilachna varivestis* Mulsant (Mexican bean beetle) and wireworms of the genera Agriotes, Athous or Limonius).

Compounds of this invention can also be mixed with one or more other biologically active compounds or agents, e.g. a compound different from a compound of Formula I, an N-oxide or a salt thereof, including insecticides, fungicides, nematocides, bactericides, acaricides, growth regulators such as rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agricultural utility. Thus, compositions of the present invention can also comprise at least one other biologically active compound or agent selected from the group consisting of an other insecticide, a fungicide, a nematocide, a bactericide, an acaricide, a growth regulator, a rooting stimulant, a chemosterilant, a semiochemical, a repellent, an attractant, a pheromone, a feeding stimulant, and an entomopathogenic bacterium, virus or fungus. Such compositions preferably further comprise at least one additional component selected from the group consisting of a surfactant, a solid diluent, and a liquid diluent.

Examples of other biologically active compounds or agents with which compounds of this invention can be formulated are: insecticides such as abamectin, acephate, acetamiprid, avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, oxamyl, parathion, parathion-methyl, permethrin, phorate, phosalone, phosmet, phosphamidon, pirimicarb, profenofos, pymetrozine, pyridalyl, pyriproxyfen, rotenone, spinosad, sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenylamino)-4H-imidazol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), fluquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metomino-strobin/fenominostrobin (SSF-126), myclobutanil, neo-asozin (ferric methanearsonate), oxadixyl, penconazole, pencycuron, probenazole, prochloraz, propamocarb, propiconazole, pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis* including ssp. *aizawai* and *kurstaki, Bacillus thuringiensis* delta endotoxin, baculovirus, and entomopathogenic bacteria, virus and fungi. Compounds of this invention and compositions thereof may be applied to plants genetically transformed to express proteins toxic to invertebrate pests (such as *Bacillus thuringiensis* toxin). The effect of the exogenous invertebrate pest control compounds and compositions may be synergistic with the expressed toxin proteins.

A general reference for these agricultural protectants is *The Pesticide Manual,* 12th Edition, C. D. S. Tomlin, Ed., British Crop Protection Council, Farnham, Surrey, U.K., 2000.

Preferred compositions of this invention include as an other biologically active compound or agent insecticides and acaricides including pyrethroids such as cypermethrin, cyhalothrin, cyfluthrin, beta-cyfluthrin, esfenvalerate, fenvalerate and tralomethrin; carbamates such as fenothicarb, methomyl, oxamyl and thiodicarb; neonicotinoids such as clothianidin, imidacloprid and thiacloprid; neuronal sodium channel blockers such as indoxacarb; insecticidal macrocyclic lactones such as spinosad, abamectin, avermectin and emamectin; γ-aminobutyric acid (GABA) antagonists such as endosulfan, ethiprole and fipronil; insecticidal ureas such as flufenoxuron and trifumuron; juvenile hormone mimics such as diofenolan and pyriproxyfen; pymetrozine; and amitraz. Preferred biological agents for mixing with compounds of this invention include *Bacillus thuringiensis* and *Bacillus thuringiensis* delta endotoxin as well as naturally occurring and genetically modified viral insecticides including members of the family Baculoviridae as well as entomophagous fungi.

Most preferred mixtures useful in the compositions and methods of this invention include a mixture of a compound of this invention with cyhalothrin; a mixture of a compound of this invention with beta-cyfluthrin; a mixture of a compound of this invention with esfenvalerate; a mixture of a compound of this invention with methomyl; a mixture of a compound of this invention with imidacloprid; a mixture of a compound of this invention with thiacloprid; a mixture of a compound of this invention with indoxacarb; a mixture of a compound of this invention with abamectin; a mixture of a compound of this invention with endosulfan; a mixture of a compound of this invention with ethiprole; a mixture of a compound of this invention with fipronil; a mixture of a compound of this invention with flufenoxuron; a mixture of a compound of this invention with pyriproxyfen; a mixture of a compound of this invention with pymetrozine; a mixture of a compound of this invention with amitraz; a mixture of a compound of this invention with *Bacillus thuringiensis* and a mixture of a compound of this invention with *Bacillus thuringiensis* delta endotoxin.

In certain instances, combinations with other invertebrate pest control compounds or agents having a similar spectrum of control but a different mode of action will be particularly advantageous for resistance management. Thus, compositions and methods of the present invention can further comprise a biologically effective amount of at least one other invertebrate pest control compound or agent having a similar spectrum of control but a different mode of action from the compounds of the invention. Contacting a plant genetically modified to express a plant protection compound (e.g., protein) or the locus of the plant with a biologically effective amount of a compound of this invention can also provide a broader spectrum of plant protection and be advantageous for resistance management.

At least one invertebrate pest is controlled in agronomic and/or nonagronomic applications by applying one or more of the compounds or compositions of this invention, in a biologically effective amount, to the environment of the pest including the agronomic and/or nonagronomic locus of infestation, to the area to be protected, or directly on the pest to be controlled. Thus, the present invention further comprises a method for the control of at least one invertebrate pest in an agronomic and/or a nonagronomic environment, comprising contacting the invertebrate pest or its environment with a biologically effective amount of one or more of the compounds of the invention; or with a biologically effective amount of a composition comprising at least one such compound; or with a biologically effective amount of composition comprising at least one such compound and a biologically effective amount of at least one other biologically active compound or agent. Examples of suitable compositions comprising at least one compound of the invention and at least one other biologically active compound or agent include granular compositions wherein the other biologically active compound is present on the same granule as the compound of the invention or on a granule separate from the granule where the compound of this invention is present.

A preferred method of contact is by spraying. Alternatively, a granular composition comprising a compound of the invention can be applied to the plant foliage or the soil. Compounds of this invention are also effectively delivered through plant uptake by contacting the plant with a composition comprising a compound of this invention applied as a soil drench of a liquid formulation, a granular formulation to the soil, a nursery box treatment or a dip of transplants. Compounds are also effective by topical application of a composition comprising a compound of this invention to the locus of infestation. Other methods of contact include application of a compound or a composition of the invention by direct and residual sprays, aerial sprays, gels, seed coatings, microencapsulations, systemic uptake, baits, eartags, boluses, foggers, fumigants, aerosols, dusts and many others. The compounds of this invention may also be impregnated into materials for fabricating invertebrate control devices (e.g. insect netting).

The compounds of this invention can be incorporated into baits that are consumed by the invertebrates or within devices such as traps and the like. Granules or baits comprising between 0.01-5% active ingredient, 0.05-10% moisture retaining agent(s) and 40-99% vegetable flour are effective in controlling soil insects at very low application rates, particularly at doses of active ingredient that are lethal by ingestion rather than by direct contact.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, spreader stickers, adjuvants, other solvents, and synergists such as piperonyl butoxide often enhance compound efficacy.

The rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.0001 kg/hectare may be sufficient or as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

The following TESTS demonstrate the control efficacy of compounds of this invention on specific pets. "Control efficacy" represents inhibition of invertebrate pest development (including mortality) that causes significantly reduced feeding. The pest control protection afforded by the compounds is not limited, however, to these species. See Index Tables A and B for compound descriptions. The following abbreviations are used in the Index Tables which follow t is tertiary, n is normal, i is iso, c is cyclo, s is secondary, Me is methyl, Et is ethyl, Pr is propyl, i-Pr is isopropyl, Bu is butyl, n-butyl is butyl, t-Bu is tertiary butyl, Hex is hexyl, c-Hex is cyclohexyl, OMe is methoxy, OEt is ethoxy, SMe is methylthio, SEt is ethylthio, CN is cyano, and $NO_2$ is nitro. The abbreviation "Ex." stands for "Example" and is followed by a number indicating in which example the compound is prepared.

INDEX TABLE A

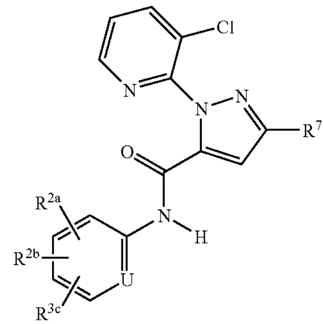

| Compound | $R^{2a}$ | $R^{2b}$ | $R^{2c}$ | $R^7$ | U | mp ° C. |
|---|---|---|---|---|---|---|
| 1 (Ex. 1) | 2-Me | 6-Cl | H | $CF_3$ | CH | 212–213 |
| 2 | 2-Et | H | 6-Et | $CF_3$ | CH | 185–195 |
| 3 | 2-Me | H | 6-OMe | $CF_3$ | CH | 150–160 |
| 4 | 2-Me | H | 6-i-Pr | $CF_3$ | CH | 145–155 |
| 5 | 2-Me | 4-Me | H | $CF_3$ | CH | 110–120 |
| 6 | 2-Me | H | H | Br | CH | 180–181 |
| 7 (Ex. 2) | 2-F | 4-F | 6-Br | Br | CH | 138–139 |
| 8 (Ex. 3) | 2-Cl | 4-Cl | H | $CF_3$ | CH | oil |
| 126 | 2-Cl | 4-CN | 6-Cl | Cl | CH | 193–194 |
| 127 | 2-F | 4-F | 6-Br | Cl | CH | 147–148 |
| 128 | 2-Me | H | H | $CF_3$ | N | 145–147 |

INDEX TABLE B (Ex. 4)

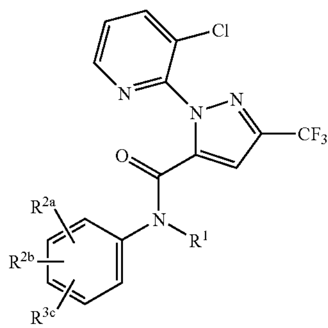

| Compound | $R^1$ | $R^{2a}$ | $R^{2b}$ | $R^{2c}$ | M + H Observed |
|---|---|---|---|---|---|
| 9 | H | 2-$NO_2$ | H | 6-$NO_2$ | 457.00 |
| 10 | H | 2-Br | 4-$NO_2$ | 6-Br | 569.96 |
| 11 | H | 2-Br | 4-Me | 6-Br | 538.95 |
| 12 | H | 2-F | 4-F | 6-F | 421.06 |
| 13 | H | 2-F | H | 6-F | 403.03 |

-continued

INDEX TABLE B (Ex. 4)

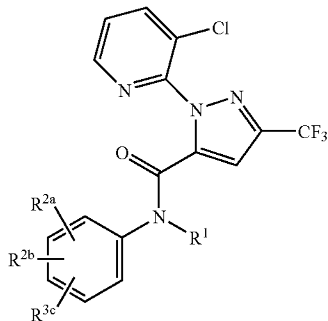

| Compound | $R^1$ | $R^{2a}$ | $R^{2b}$ | $R^{2c}$ | M + H Observed |
|---|---|---|---|---|---|
| 14 | H | 2-Cl | 4-Cl | 6-Cl | 470.98 |
| 15 | H | 2-Cl | H | 6-Cl | 437.00 |
| 16 | H | 2-Cl | 3-Me | 6-Cl | 449.02 |
| 17 | H | 2-Cl | H | 6-Me | 415.03 |
| 18 | H | 2-Me | 4-Me | 6-$NO_2$ | 440.07 |
| 19 | H | 2-Me | 4-Me | 6-Me | 409.09 |
| 20 | H | 2-Me | H | 6-$NO_2$ | 426.05 |
| 21 | H | 2-Me | H | 6-i-Pr | 423.10 |
| 22 | H | 2-Me | H | 6-Me | 395.07 |
| 23 | H | 2-Me | H | 6-Et | 409.09 |
| 24 | H | 2-Et | H | 6-Et | 423.10 |
| 26 | H | 2-Br | 4-F | 6-Br | 542.83 |
| 27 | H | 2-Cl | 4-Me | 6-Me | 429.05 |
| 28 | H | 2-$CF_3$ | H | 6-F | 453.06 |
| 29 | H | 2-OMe | H | 6-Me | 411.10 |
| 30 | H | 2-Br | 4-i-Pr | 6-Br | 566.95 |
| 31 | H | 2-Cl | 4-CN | 6-Cl | 460.01 |
| 32 | H | 2-Me | 4-CN | 6-Cl | 440.07 |
| 33 | H | 2-Cl | 4-$CF_3$ | 6-Br | 548.98 |
| 34 | H | 2-Cl | 4-Cl | 6-Me | 449.02 |
| 35 | H | 2-Br | 4-c-Hex | 6-Br | 606.98 |
| 36 | H | 2-Br | 4-$CF_3$ | 6-Br | 592.88 |
| 37 | H | 2-$NO_2$ | H | H | 412.12 |
| 38 | H | 2-OMe | H | H | 397.15 |
| 39 | H | 2-OEt | H | H | 411.16 |
| 40 | H | 2-Ph | H | H | 443.17 |
| 41 | H | 2-SMe | H | H | 413.13 |
| 42 | H | 2-$CF_3$ | H | H | 435.14 |
| 43 | H | 2-i-Pr | H | H | 409.19 |
| 44 | H | 2-Me | H | H | 381.15 |
| 45 | H | 2-Me | 4-Me | H | 395.17 |
| 46 | H | 2-Me | 5-Me | H | 395.17 |
| 47 | H | 2-$CH_2$Ph | H | H | 457.22 |
| 48 | H | 2-Et | H | H | 395.18 |
| 49 | H | 3-CN | H | H | 392.15 |
| 50 | H | 3-Br | H | H | 445.08 |
| 51 | H | 3-F | H | H | 385.15 |
| 52 | H | 3-Cl | H | H | 401.14 |
| 53 | H | 3-Cl | 4-Cl | H | 435.12 |
| 54 | H | 3-Cl | 5-Cl | H | 435.12 |
| 55 | H | 3-I | H | H | 493.13 |
| 56 | H | 3-$NO_2$ | H | H | 412.19 |
| 57 | H | 3-OMe | H | H | 397.22 |
| 58 | H | 3-OEt | H | H | 411.24 |
| 59 | H | 3-SMe | H | H | 413.20 |
| 60 | H | 3-$CF_3$ | H | H | 435.06 |
| 61 | H | 3-Me | H | H | 381.18 |
| 62 | H | 4-CN | H | H | 393.10 |
| 63 | H | 4-Br | H | H | 447.00 |
| 64 | H | 2-Me | 4-Br | H | 461.11 |
| 65 | H | 4-F | H | H | 385.07 |
| 66 | H | 4-Cl | H | H | 401.04 |
| 67 | H | 3-$CF_3$ | 4-Cl | H | 469.02 |
| 68 | H | 4-I | H | H | 492.97 |
| 69 | H | 4-$NO_2$ | H | H | 412.06 |

-continued

INDEX TABLE B (Ex. 4)

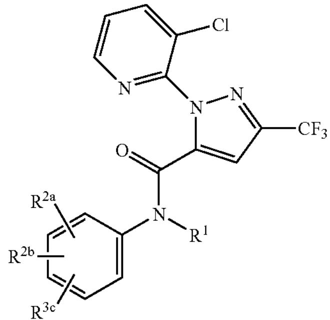

| Compound | $R^1$ | $R^{2a}$ | $R^{2b}$ | $R^{2c}$ | M + H Observed |
|---|---|---|---|---|---|
| 70 | H | 4-OPh | H | H | 459.09 |
| 71 | H | 4-OMe | H | H | 397.08 |
| 72 | H | 4-OEt | H | H | 411.08 |
| 73 | H | 4-Ph | H | H | 443.08 |
| 74 | H | 4-SMe | H | H | 413.03 |
| 75 | H | 4-t-Bu | H | H | 423.08 |
| 76 | H | 4-i-Pr | H | H | 409.07 |
| 77 | H | 4-Me | H | H | 381.04 |
| 78 | H | 4-$CH_2CN$ | H | H | 406.04 |
| 79 | H | 4-n-Pr | H | H | 409.06 |
| 80 | H | 2-OMe | 5-OMe | H | 427.03 |
| 81 | H | 2-OMe | 4-OMe | H | 427.03 |
| 82 | H | 3-OMe | 5-OMe | H | 427.04 |
| 83 | H | 3-OMe | 4-OMe | 5-OMe | 457.04 |
| 84 | H | 2-n-Pr | H | H | 409.06 |
| 86 | H | 2-OPh | H | H | 459.02 |
| 87 | H | 2-$OCF_3$ | H | H | 450.98 |
| 88 | H | 4-$OCF_3$ | H | H | 450.98 |
| 89 | H | 3-$OCF_3$ | H | H | 450.97 |
| 90 | H | 3-OPh | H | H | 459.02 |
| 91 | H | 2-Br | 4-$CF_3$ | H | 512.89 |
| 92 | H | 2-OMe | 5-$CF_3$ | H | 464.99 |
| 93 | H | 2-$CF_3$ | 4-Br | H | 512.90 |
| 94 | H | 4-$CF_3$ | H | H | 434.99 |
| 95 | H | 4-$OCF_3H$ | H | H | 433.00 |
| 96 | H | 2-$CH_2CN$ | H | H | 406.04 |
| 97 | H | 2-t-Bu | H | H | 423.08 |
| 98 | H | 2-$OCF_2H$ | H | H | 433.01 |
| 99 | H | 2-Br | 2-Cl | H | 480.92 |
| 100 | H | 2-Cl | 4-$CF_3$ | H | 469.00 |
| 101 | H | 2-N-piperidine | H | H | 450.12 |
| 102 | Me | 4-Cl | H | H | 415.05 |
| 103 | $CH_2CH_2CN$ | H | H | H | 420.09 |
| 104 | Et | 2-$NO_2$ | H | H | 440.09 |
| 105 | Me | H | H | H | 381.12 |
| 106 | Et | H | H | H | 395.11 |
| 107 | Me | 4-Me | H | H | 395.11 |
| 108 | Et | 2-Me | H | H | 409.12 |
| 109 | n-Bu | H | H | H | 423.15 |
| 111 | H | H | H | H | 367.22 |
| 112 | H | 2-CN | H | H | 392.13 |
| 113 | H | 2-Br | H | H | 447.06 |
| 114 | H | 2-Br | 4-Me | H | 461.08 |
| 115 | H | 2-Br | 5-$CF_3$ | H | 515.06 |
| 116 | H | 2-F | H | H | 385.13 |
| 117 | H | 2-F | 4-F | H | 403.12 |
| 118 | H | 2-F | 5-F | H | 403.12 |
| 119 | H | 2-Cl | H | H | 401.10 |
| 120 | H | 2-Cl | 4-Br | H | 481.02 |
| 121 | H | 2-Cl | 4-Cl | H | 437.07 |
| 122 | H | 2-Cl | 4-Me | H | 415.12 |
| 123 | H | 2-Cl | 5-Cl | H | 437.09 |
| 124 | H | 2-Cl | 5-$CF_3$ | H | 469.10 |
| 125 | H | 2-I | H | H | 493.05 |

Biological Examples Of The Invention

Test A

For evaluating control of diamondback moth (*Plutella xylostella*) the test unit consisted of a small open container with a 12-14-day-old radish plant inside. This was pre-infested with 10-15 neonate larvae on a piece of insect diet by use of a core sampler to remove a plug from a sheet of hardened insect diet having many larvae growing on it and transfer the plug containing larvae and diet to the test unit. The larvae moved onto the test plant as the diet plug dried out.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc., Greely, Colo. USA), unless otherwise indicated. The formulated compounds were applied in 1 mL of liquid through a SUJ2 atomizer nozzle with ⅛ JJ custom body (Spraying Systems Co. Wheaton, Ill., USA) positioned 1.27 cm (0.5 inches) above the top of each test unit. All experimental compounds in these tests were sprayed at 250 ppm (or lower) and replicated three times. After spraying of the formulated test compound, each test unit was allowed to dry for 1 hour and then a black, screened cap was placed on top. The test units were held for 6 days in a growth chamber at 25° C. and 70% relative humidity. Plant feeding damage was then visually assessed based on foliage consumed.

Of the compounds tested* the following provided very good to excellent levels of plant protection (ratings of 0-1, 10% or less feeding damage): 1, 7*, 8* 126*, 127* and 128*.

Test B

For evaluating control of fall armyworm (*Spodoptera frugiperda*) the test unit consisted of a small open container with a 4-5-day-old corn (maize) plant inside. This was pre-infested (using a core sampler) with 10-15 1-day-old larvae on a piece of insect diet.

Test compounds were formulated and sprayed at 250 ppm (or lower) as described for Test A. The applications were replicated three times. After spraying, the test units were maintained in a growth chamber and then visually rated as described for Test A.

Of the compounds tested*, the following provided excellent levels of plant protection (10% or less feeding damage): 1, 6*, 7*, 8* and 127***.

Test C

For evaluating control of tobacco budworm (*Heliothis virescens*) the test unit consisted of a small open container with a 6-7 day old cotton plant inside. This was pre-infested (using a core sampler) with 8 2-day-old larvae on a piece of insect diet.

Test compounds were formulated and sprayed at 250 ppm (or lower) as described for Test A. The applications were replicated three times. After spraying, the test units were maintained in a growth chamber and then visually rated as described for Test A.

Of the compounds tested*, the following provided very good to excellent levels of plant protection (20% or less feeding damage): 7* and 8*.

Test D

For evaluating control of beet armyworm (*Spodoptera exigua*) the test unit consisted of a small open container with a 4-5-day-old corn plant inside. This was pre-infested (using a core sampler) with 10-15 1-day-old larvae on a piece of insect diet.

Test compounds were formulated and sprayed at 250 ppm (or lower) as described for Test A. The applications were replicated three times. After spraying, the test units were maintained in a growth chamber and then visually rated as described for Test A.

Of the compounds tested*, the following provided very good to excellent levels of plant protection (20% or less feeding damage): 7***.

Test E

As an alternative to evaluate control of fall armyworm (*Spodoptera frugiperda*) the test unit consisted of a microtiter plate filled with 175 μL of lepidopteran soy wheat germ diet. Each well was treated with 25 μL of a 1050 μM (or lower) experimental compound, formulated in 75/25 acetone/water. Following chemical application, the plates were dried in a ventilated enclosure for 24 hours. Following the 24 hour drying period, the plates were infested with fall armyworm egg and then sealed. Test units were then stored for 6 days at 27° C. (day) 70% relative humidity. Activity was assessed based on insect kill.

Of the compounds tested, the following provided very good to excellent levels of fall armyworm control (90% or more of live insect killed): 10, 11, 12, 13, 14, 15, 17, 19, 20, 22, 26, 27, 28, 29, 31, 32, 34, 44, 64, 69, 91, 94, 99, 100, 114, 115, 120 and 121.

*Compounds 9 through 125 of Index Table B were not evaluated in this test.

** Tested at 250 ppm.

Tested at 50 ppm

What is claimed is:

1. A compound of Formula I, an N-oxide or a salt thereof

I wherein:

A is O;

B is a phenyl ring or a pyridine ring, each ring substituted with 1 to 5 $R^2$;

J is J-1;

J-1

;

$R^1$ is H or $C_1$-$C_6$ alkyl;

from 1 to 3 $R^2$ groups are other than H and are independently selected from the group consisting of $C_1$-$C_6$ alkyl, $C_1$-$C_6$ haloalkyl, $C_2$-$C_4$ cyanoalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl and $C_1$-$C_4$ haloalkylsulfonyl; and at least one $R^2$ is ortho to the $NR^1C(=A)J$ moiety and is other than H;

$R^5$ is

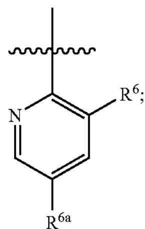

$R^6$ is selected from the group consisting of $C_1$-$C_6$ alkyl, $C_3$-$C_6$ cycloalkyl, $C_1$-$C_6$ haloalkyl, halogen, CN, $C_1$-$C_4$ alkoxy, $C_1$-$C_4$ alkylthio, $C_1$-$C_4$ haloalkoxy, and $C_1$-$C_4$ haloalkylthio; and each $R^{6a}$ and $R^7$ are independently selected from the group consisting of H, $C_1$-$C_6$ alkyl, $C_3$-$C_6$ cycloalkyl, $C_1$-$C_6$ haloalkyl, halogen, CN, $C_1$-$C_4$ alkoxy, $C_1$-$C_4$ alkylthio, $C_1$-$C_4$ haloalkoxy, and $C_1$-$C_4$ haloalkylthio.

2. The compound of claim 1 wherein two $R^2$ are ortho to the $NR^1C(=A)J$ moiety.

3. The compound of claim 1 wherein $R^6$ is $C_1$-$C_4$ alkyl, $C_1$-$C_4$ haloalkyl, halogen or CN; and $R^7$ is H, $CH_3$, $CF_3$, $CH_2CF_3$, $CHF_2$, $OCH_2CF_3$, $OCHF_2$ or halogen.

4. The compound of claim 3 wherein:

$R^6$ is Cl or Br; and $R^7$ is halogen, $OCH_2CF_3$, $OCHF_2$ or $CF_3$.

5. A composition comprising: at least one compound of claim 1; and at least one additional component selected from the group consisting of a surfactant, a solid diluent and a liquid diluent.

6. The composition of claim 5 further comprising at least one other biologically active compound or agent.

7. A method for controlling at least one invertebrate pest comprising: contacting the invertebrate pest or its environment with a biologically effective amount of at least one compound of claim 1.

8. The method of claim 7 wherein the composition further comprises a biologically effective amount of at least one other biologically active compound or agent for controlling invertebrate pests.

* * * * *

UNITED STATES PATENT AND TRADEMARK OFFICE
CERTIFICATE OF CORRECTION

PATENT NO. : 7,754,738 B2
APPLICATION NO. : 10/514183
DATED : July 13, 2010
INVENTOR(S) : George Philip Lahm et al.

It is certified that error appears in the above-identified patent and that said Letters Patent is hereby corrected as shown below:

Column 17, line 34, "61-4°C." should read --61-64°C.--

Columns 20, 21, 23, 25, 27, 29, Table 1, in the formula structure "$R^{3c}$" should read --$R^{2c}$--

Table 1

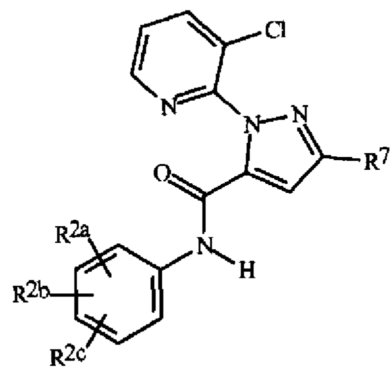

Columns 29, 31, 33, 35, 37, Table 2, in the formula structure "$R^{3c}$" should read --$R^{2c}$--

Table 2

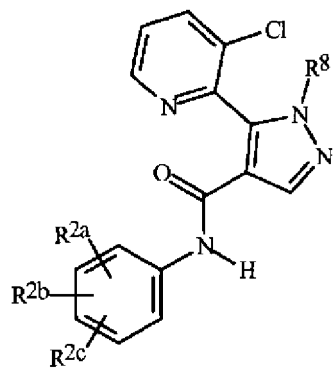

Signed and Sealed this
Seventh Day of August, 2012

David J. Kappos
*Director of the United States Patent and Trademark Office*

Columns 29, 31, 33, 35, 37, Table 2, in the headings in the 4th and 8th columns "$R^7$" should read --$R^8$--

Columns 39, 41, 43, 45, Table 3, in the formula structure "$R^{3c}$" should read --$R^{2c}$--

Table 3

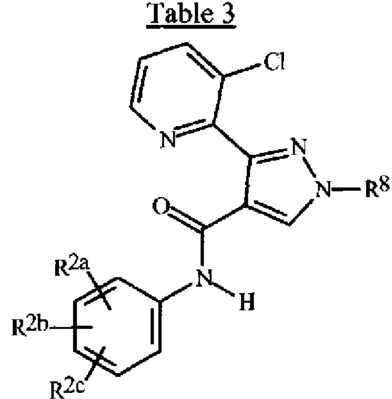

Columns 39, 41, 43, 45, Table 3, in the headings in the 4th and 8th columns "$R^7$" should read --$R^8$--

Columns 47, 49, 51, 53, 55, 57, Table 4, in the formula structure "$R^{3c}$" should read --$R^{2c}$--

Table 4

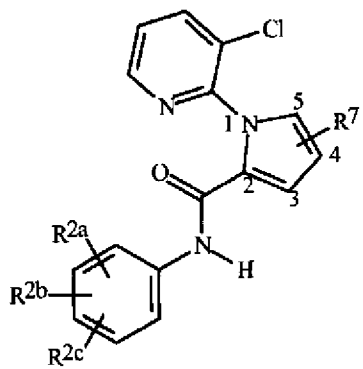

Columns 57, 59, 61, 63, 65, Table 5, in the formula structure "$R^{3c}$" should read --$R^{2c}$--

Table 5

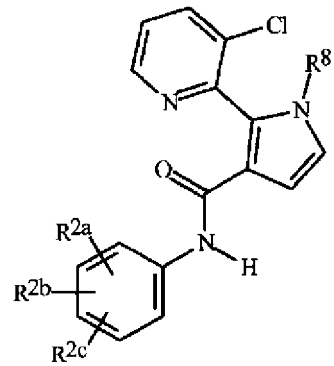

Columns 65, 67, 69, 71, 73, Table 6, in the formula structure "$R^{3c}$" should read --$R^{2c}$--
Table 6
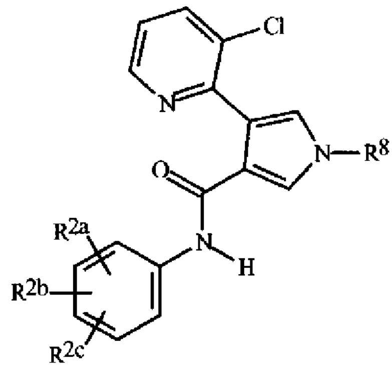
Column 86, Index Table A, in the formula structure "$R^{3c}$" should read --$R^{2c}$--
INDEX TABLE A
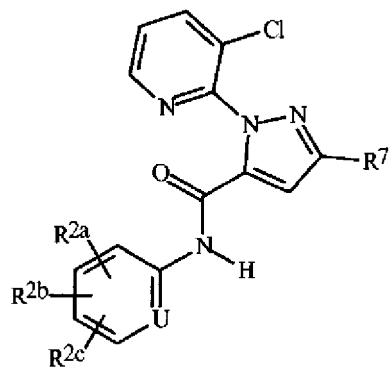
Columns 86, 87, 89, Index Table B (Ex. 4), in the formula structure "$R^{3c}$" should read --$R^{2c}$--
INDEX TABLE B (Ex. 4)
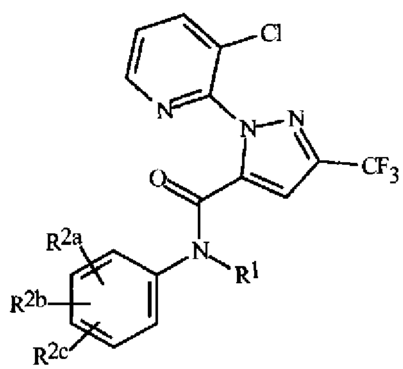
Column 92, line 37 "Tested at 50 ppm" should read --***Tested at 50 ppm--